US010023880B2

(12) United States Patent
Pauza et al.

(10) Patent No.: US 10,023,880 B2
(45) Date of Patent: *Jul. 17, 2018

(54) METHODS AND COMPOSITIONS FOR THE ACTIVATION OF GAMMA-DELTA T-CELLS

(71) Applicant: American Gene Technologies International Inc., Rockville, MD (US)

(72) Inventors: Charles David Pauza, Baltimore, MD (US); Haishan Li, North Potomac, MD (US); Tyler Lahusen, Frederick, MD (US); Mei-Ling Liou, Germantown, MD (US)

(73) Assignee: American Gene Technologies International Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/850,937

(22) Filed: Dec. 21, 2017

(65) Prior Publication Data
US 2018/0142258 A1    May 24, 2018

Related U.S. Application Data

(63) Continuation of application No. 15/652,080, filed on Jul. 17, 2017, now Pat. No. 9,914,938, which is a continuation of application No. PCT/US2017/013399, filed on Jan. 13, 2017.

(60) Provisional application No. 62/279,474, filed on Jan. 15, 2016.

(51) Int. Cl.
| C07H 21/02 | (2006.01) |
| C07H 21/04 | (2006.01) |
| C12N 15/86 | (2006.01) |
| C12N 15/113 | (2010.01) |
| C12N 5/0783 | (2010.01) |
| A61K 38/16 | (2006.01) |
| C12N 5/00 | (2006.01) |
| A61K 39/00 | (2006.01) |
| A61K 48/00 | (2006.01) |

(52) U.S. Cl.
CPC .............. *C12N 15/86* (2013.01); *A61K 38/16* (2013.01); *C12N 5/0636* (2013.01); *C12N 15/113* (2013.01); *A61K 48/00* (2013.01); *A61K 2039/5158* (2013.01); *C12N 5/00* (2013.01); *C12N 2310/14* (2013.01); *C12N 2310/141* (2013.01); *C12N 2310/531* (2013.01)

(58) Field of Classification Search
None
See application file for complete search history.

(56) References Cited

U.S. PATENT DOCUMENTS

| 5,674,703 A | 10/1997 | Woo et al. |
| 6,156,514 A | 12/2000 | Acevedo et al. |
| 6,635,472 B1 | 10/2003 | Lauermann |
| 8,124,752 B2 | 2/2012 | Bumcrot et al. |
| 9,834,790 B1 | 12/2017 | Pauza et al. |
| 9,914,938 B2 | 3/2018 | Pauza et al. |
| 2002/0168345 A1 | 11/2002 | Doug et al. |
| 2003/0013196 A1 | 1/2003 | Engelman et al. |
| 2003/0119770 A1 | 6/2003 | Lai |
| 2004/0161412 A1 | 8/2004 | Penn et al. |
| 2004/0214158 A1 | 10/2004 | Sethi et al. |
| 2006/0183230 A1 | 8/2006 | Silla et al. |
| 2006/0246520 A1 | 11/2006 | Champagne et al. |
| 2007/0026521 A1 | 2/2007 | Colosi |
| 2008/0003225 A1 | 1/2008 | Vie et al. |
| 2008/0003682 A1 | 1/2008 | Lois-Caballe et al. |
| 2008/0039413 A1 | 2/2008 | Morris et al. |
| 2008/0199961 A1 | 8/2008 | Rasko et al. |
| 2008/0293142 A1 | 11/2008 | Liu et al. |
| 2009/0148936 A1 | 6/2009 | Stout et al. |
| 2009/0304688 A1 | 12/2009 | Fournie et al. |
| 2010/0017911 A1 | 1/2010 | Dawson et al. |
| 2010/0069372 A1 | 3/2010 | Kazantsev |
| 2010/0119511 A1 | 5/2010 | Wang et al. |
| 2011/0008803 A1 | 1/2011 | Stockwell et al. |
| 2011/0207226 A1 | 8/2011 | Ni et al. |
| 2012/0053223 A1 | 1/2012 | Benkirane et al. |
| 2012/0027725 A1 | 2/2012 | Galvin et al. |
| 2012/0114607 A1 | 5/2012 | Lai et al. |
| 2012/0034197 A1 | 8/2012 | Young et al. |
| 2012/0201794 A1 | 9/2012 | Chen et al. |
| 2013/0078276 A1 | 3/2013 | Robinson et al. |
| 2013/0090371 A1 | 4/2013 | Lu et al. |
| 2013/0142766 A1 | 6/2013 | Dodo et al. |
| 2014/0162894 A1 | 6/2014 | Hatchwell et al. |
| 2014/0234958 A1 | 8/2014 | Kashara et al. |
| 2014/0248277 A1 | 9/2014 | Hoffman et al. |
| 2014/0336245 A1 | 11/2014 | Mingozzi et al. |

(Continued)

FOREIGN PATENT DOCUMENTS

| CN | 101805750 | 8/2010 |
| WO | 2002020554 | 3/2002 |

(Continued)

OTHER PUBLICATIONS

Vargas, J. Jr. et al., "Conditionally replicating lentiviral-hybrid episomal vectors for suicide gene therapy," Antiviral Res., vol. 80 No. 3, pp. 288-294, (Dec. 2008).

Thompson et al., "Alkylamines cause Vγ9Vδ2 T-cell activation and proliferation by inhibiting the mevalonate pathway," Blood, vol. 107, pp. 651-654, (Jan. 2006).

Gober et al., "Human T Cell Receptor γδ Cells Recognize Endogenous Mevalonate Metabolites in Tumor Cells," J. of Experimental Med., vol. 197, pp. 163-168, (Jan. 2003).

Goepfert, et al., "Specificity and 6-Month Durability of Immune Responses Induced by DNA and Recombinant Modified Vaccinia Ankara Vaccines Expressing HIV-2 Virus-Like Particles," J. Infectious Diseases, vol. 210, pp. 99-110, (Jul. 2014).

(Continued)

*Primary Examiner* — Sean McGarry
(74) *Attorney, Agent, or Firm* — Snell & Wilmer LLP

(57) ABSTRACT

The present invention relates generally to methods and compositions for gene therapy and immunotherapy that activate gamma delta T-cells, and in particular, can be used in the treatment of various cancers and infectious diseases.

11 Claims, 15 Drawing Sheets

(56) References Cited

U.S. PATENT DOCUMENTS

| | | | |
|---|---|---|---|
| 2015/0126580 | A1 | 5/2015 | DePinho et al. |
| 2015/0176006 | A1 | 6/2015 | Krause et al. |
| 2016/0060707 | A1 | 3/2016 | Goldenberg et al. |
| 2016/0243169 | A1 | 8/2016 | Chen et al. |
| 2017/0335344 | A1 | 11/2017 | Pauza et al. |
| 2018/0010147 | A1 | 1/2018 | Pauza |
| 2018/0142257 | A1 | 5/2018 | Pauza |

FOREIGN PATENT DOCUMENTS

| | | |
|---|---|---|
| WO | 2005033282 | 4/2005 |
| WO | 2009100928 | 8/2009 |
| WO | 2009147445 | 12/2009 |
| WO | 2010051521 | 5/2010 |
| WO | 2012061075 | 5/2012 |
| WO | 2014117050 | 7/2014 |
| WO | 2014187881 | 11/2014 |
| WO | 2015017755 | 2/2015 |
| WO | 2015042308 | 3/2015 |
| WO | 2015078999 | 6/2015 |
| WO | 2016061232 | 4/2016 |
| WO | 2016200997 | 7/2016 |
| WO | 2017007994 | 1/2017 |
| WO | 2017123918 | 7/2017 |
| WO | 2017139065 | 8/2017 |
| WO | 2017156311 | 9/2017 |
| WO | 2017213697 | 12/2017 |
| WO | 2017214327 | 12/2017 |
| WO | 2018009246 | 1/2018 |
| WO | 2018009847 | 1/2018 |
| WO | 2018017882 | 1/2018 |

OTHER PUBLICATIONS

Human papillomavirus type 16 (HPV16), complete genome; GenBank: K02718.1; Publication [online], https://www.ncbi.nlm.nih.gov/nucleotide/333031?report=genbank&log$=nucltop &blast_rank=22&RID=H3E1THFU014; pp. 1-4, (Mar. 1994).
{Long control region} [Human papillomavirus, type 16, Genomic, 860 nt]; Accession S60559. Publication [online], https://www.ncbi.nlm.nih.gov/nucleotide/237343?report=genbank&log$=nucltop &blast_rank=1&RID=H3FCKA00014; pp. 1, (May 1993).
Tebas, P. et al, "Antiviral effects of autologous CD4 T cells genetically modified with a conditionally replicating lentiviral vector expressing long antisense to HIV," Blood, vol. 121, No. 9, pp. 1524-1533, (2013).
Tebas, p. et al., "Gene Editing of CCR5 in Autologous CD4 T Cells of Persons Infected with HIV," The New England Journal of Medicine, vol. 370 (10), pp. 901-910, (Mar. 2014).
Li et al., "Reduced Expression of the Mevalonate Pathway Enzyme Farnesyl Pyrophosphate Synthase Unveils Recognition of Tumor Cells by Vγ9Vδ2 T Cells," J. of Immunology, vol. 182, pp. 8118-8124, (2009).
Wang et al., "Indirect Stimulation of Human Vγ9Vδ2 T Cells through Alterations in Isoprenoid Metabolism," J. of Immunology, vol. 187 pp. 5099-5113, (2011).
Stunkel et al., "The Chromatin Structure of the Long Control Region of Human Papillomavirus Type 16 Repress Viral Oncoprotein Expression," Journal of Virology, vol. 73, No. 3, pp. 1918-1930, (Mar. 1999).
Lu et al., "Anti-sense-Mediated Inhibition of Human Immunodeficiency Virus (HIV) Replication by Use of an HIV Type 1-Based Vector Results in Severely Attenuated Mutants Incapable of Developing Resistance," Journal of Virology, vol. 79, No. 13, pp. 7079-7088, (Jul. 2004).
Dieli et al., ""Targeting Human γδ T Cells with Zoledronate and Interleukin-2 for Immunotherapy of Hormone-Refractory Prostate Cancer,"" Europe PMC Funders Group, Cancer Res. vol. 67(15), pp. 7450-1451, (Aug. 2007).

GenBank Accession No. S60559 "(long control region) [human papillomavirus, type 16, Genomic, 860 nt]," [located online Nov. 21, 2017 at https://ncbi.nlm.nih.gov/nuccore/S60559] entire DNA sequence, (May 1993).
GenBank Accession No. JG619773, MNESC1NG-T3-001_L15_6FEB2009_054 MNESC1NG cell culture from Mahonia nervosa Berberis nervosa cDNA, mRNA sequence, (online). [Retrieved on Dec. 5, 2017]. Retrieved from the internet :< URL: https://www.ncbi.nlm.nih.gov/nucest/JG619773 > entire document, (Feb. 2014).
Moser et al., "γδ T cells: novel initiators of adaptive immunity," Immunological Reviews, vol. 215, pp. 89-102, (Feb. 2007).
PCT: International Search Report dated Nov. 7, 2016 in Application No. PCT/US2016/036519.
PCT: Written Opinion dated Nov. 7, 2016 in Application No. PCT/US2016/036519.
PCT: International Search Report dated Oct. 19, 2016 in Application No. PCT/US2016/041456.
PCT: Written Opinion dated Oct. 19, 2016 in Application No. PCT/US2016/041456.
PCT: International Search Report dated Jul. 20, 2017 in Application No. PCT/US2017/043157.
PCT: Written Opinion dated Jul. 20, 2017 in application No. PCT/US2017/043157.
PCT: International Search Report dated Jun. 9, 2017 in Application No. PCT/US2016/066185.
PCT: Written Opinion dated Jun. 9, 2017 in Application No. PCT/US2016/066185.
PCT: International Search Report dated Jul. 17, 2017 in Application No. PCT/US2017/013019.
PCT: Written Opinion dated Jul. 17, 2017 in Application No. PCT/US2017/013019.
PCT: International Search Report dated May 26, 2017 in Application No. PCT/US2017/013399.
PCT: Written Opinion dated May 26, 2017 in Application No. PCT/US2017/013399.
PCT: International Search report dated Aug. 25, 2017 in Application No. PCT/US2017/021639.
PCT: Written Opinion dated Aug. 25, 2017 Application No. PCT/US2017/021639.
PCT: International Search Report dated Nov. 8, 2017 Application No. PCT/US2017/041168.
PCT: Written Opinion dated Nov. 8, 2017 in Application No. PCT/US2017/041168.
PCT: International Search Report dated Dec. 15, 2017 in Application No. PCT/US2017/36433.
PCT: Written Opinion dated Dec. 15, 2017 in Application No. PCT/US2017/36433.
PCT: International Search Report date Jul. 14, 2017 in Application No. PCT/US2017/013024.
PCT: Written Opinion dated Jul. 14, 2017 in application No. PCT/US2017/013024.
USPTO; Notice of Allowance dated Oct. 13, 2017 in U.S. Appl. No. 14/706,481.
USPTO; Requirement for Restriction dated Oct. 23, 2017 in U.S. Appl. No. 15/668,223.
USPTO; Notice of Allowance dated Nov. 2, 2017 in U.S. Appl. No. 15/652,080.
Capietto, A. H., et al., "Stimulated gammadelta T cells increase the in vivo efficacy of trastuzumab in HER-2+ breast cancer," J Immunol 187(2): 1031-1038, (2011).
Chen, Z. and M. S. Freedman, "CD16+ in gammadelta T cells mediate antibody dependent cellular cytotoxicity: potential mechanism in the pathogenesis of multiple sclerosis," Clin Immunol 128(2): 219-227, (2008).
Couzi, L. et al., "Antibody-dependent anti-cytomegalovirus activity of human gammadelta T cells expressing CD16 (FcgammaRIIIa)," Blood 119(6): 1418-1427, (2012).
Fisher, J. P. et al., "Effective combination treatment of GD2-expressing neuroblastoma and Ewing's sarcoma using anti-GD2 ch14.18/CHO antibody with Vgamma9Vdelta2+ gammadeltaT cells," Oncoimmunology 5(1): e1025194, (2016).

(56) References Cited

OTHER PUBLICATIONS

Gertner-Dardenne, J. et al., "Bromohydrin pyrophosphate enhances antibody-dependent cell-mediated cytotoxicity induced by therapeutic antibodies," Blood 113(20): 4875-4884, (2009).

Poonia, B. and C. D. Pauza, "Gamma delta T cells from HIV+ donors can be expanded in vitro by zoledronate/interleukin-2 to become cytotoxic effectors for antibody-dependent cellular cytotoxicity," Cytotherapy 14(2): 173-181, (2012).

Schiller, C. B. et al., "CD19-specific triplebody SPM-1 engages NK and gammadelta T cells for rapid and efficient lysis of malignant B-lymphoid cells," Oncotarget 7(50): 83392-83408, (2016).

Tokuyama, H. et al., "V gamma 9 V delta 2 T cell cytotoxicity against tumor cells is enhanced by monoclonal antibody drugs—rituximab and trastuzumab," Int J Cancer 122(11): 2526-2534, (2008).

Zufferey et al., "Self-Inactivating Lentivirus Vector for Safe and Efficient In Vivo Gene Delivery," Journal of Virology, vol. 72(12), pp. 9873-9880, (1998).

USPTO; Non-Final Office Action dated Feb. 22, 2018 in U.S. Appl. No. 15/849,062.

USPTO; Non-Final Office Action dated Feb. 22, 2018 in U.S. Appl. No. 13/333,882.

USPTO; Notice of Allowance dated Mar. 26, 2018 in U.S. Appl. No. 15/668,223.

Ostertag et al., Brain Tumor Eradication and Prolonged Survival from Intratumoral Conversion of 5-Fluorocytosine to 5-fluorouracil Using a Nonlytic Retroviral Replicating Vector, Neoro-Oncology 14(2), pp. 145-159, Feb. 2012.

Twitty et al., Retroviral Replicating Vectors Deliver Cytosine Deaminase Leading to Targeted 5-Fluorouracil-Mediated Cytotoxicity in Multiple Human Cancer Types, Human Gene Therapy Methods, 27(1), pp. 17-31, Feb. 1, 2016.

PCT: International Search Report dated May 29, 2018 in Application No. PCT/US2018/012998.

PCT: Written Opinion dated May 29, 2018 in Application No. PCT/US2018/012998.

USPTO; Notice Allowance dated Apr. 26, 2018 in U.S. Appl. No. 15/849,062.

SEQUENCE LISTING

<160> NUMBER OF SEQ ID NOS: 67

<210> SEQ ID NO 1
<211> LENGTH: 53
<212> TYPE: DNA
<213> ORGANISM: Artificial Sequence
<220> FEATURE:
<223> OTHER INFORMATION: FDPS shRNA sequence #1

<400> SEQUENCE: 1
gtcctggagt acaatgccat tctcgagaat ggcattgtac tccaggactt ttt      53

<210> SEQ ID NO 2

```
<211> LENGTH: 53
<212> TYPE: DNA
<213> ORGANISM: Artificial Sequence
<220> FEATURE:
<223> OTHER INFORMATION: FDPS shRNA sequence #2

<400> SEQUENCE: 2
gcaggatttc gttcagcact tctcgagaag tgctgaacga aatcctgctt ttt            53

<210> SEQ ID NO 3
<211> LENGTH: 53
<212> TYPE: DNA
<213> ORGANISM: Artificial Sequence
<220> FEATURE:
<223> OTHER INFORMATION: FDPS shRNA sequence #3

<400> SEQUENCE: 3
gccatgtaca tggcaggaat tctcgagaat tcctgccatg tacatggctt ttt            53

<210> SEQ ID NO 4
<211> LENGTH: 53
<212> TYPE: DNA
<213> ORGANISM: Artificial Sequence
<220> FEATURE:
<223> OTHER INFORMATION: FDPS shRNA sequence #4

<400> SEQUENCE: 4
gcagaaggag gctgagaaag tctcgagact ttctcagcct ccttctgctt ttt            53

<210> SEQ ID NO 5
<211> LENGTH: 116
<212> TYPE: DNA
<213> ORGANISM: Artificial Sequence
<220> FEATURE:
<223> OTHER INFORMATION: miR30 FDPS sequence #1

<400> SEQUENCE: 5
aaggtatatt gctgttgaca gtgagcgaca ctttctcagc ctccttctgc gtgaagccac     60
agatggcaga aggaggctga gaaagtgctg cctactgcct cggacttcaa ggggct        116

<210> SEQ ID NO 6
<211> LENGTH: 114
<212> TYPE: DNA
<213> ORGANISM: Artificial Sequence
<220> FEATURE:
<223> OTHER INFORMATION: miR30 FDPS sequence #2

<400> SEQUENCE: 6
aaggtatatt gctgttgaca gtgagcgaca ctttctcagc ctccttctgc gtgaagccac     60
agatggcaga agggctgaga aagtgctgcc tactgcctcg acttcaagg ggct            114

<210> SEQ ID NO 7
<211> LENGTH: 91
<212> TYPE: DNA
<213> ORGANISM: Artificial Sequence
<220> FEATURE:
<223> OTHER INFORMATION: miR30 FDPS sequence #3

<400> SEQUENCE: 7
tgctgttgac agtgagcgac tttctcagcc tccttctgcg tgaagccaca gatggcagaa     60
ggaggctgag aaagttgcct actgcctcgg a                                    91

<210> SEQ ID NO 8
<211> LENGTH: 115
```

<212> TYPE: DNA
<213> ORGANISM: Artificial Sequence
<220> FEATURE:
<223> OTHER INFORMATION: miR155 FDPS sequence #1

<400> SEQUENCE: 8
cctggaggct tgctgaaggc tgtatgctga ctttctcagc ctccttctgc ttttggccac    60
tgactgagca gaagggctga gaaagtcagg acacaaggcc tgttactagc actca    115

<210> SEQ ID NO 9
<211> LENGTH: 114
<212> TYPE: DNA
<213> ORGANISM: Artificial Sequence
<220> FEATURE:
<223> OTHER INFORMATION: miR21 FDPS sequence #1

<400> SEQUENCE: 9
catctccatg gctgtaccac cttgtcggga ctttctcagc ctccttctgc ctgttgaatc    60
tcatggcaga aggaggcgag aaagtctgac attttggtat ctttcatctg acca    114

<210> SEQ ID NO 10
<211> LENGTH: 114
<212> TYPE: DNA
<213> ORGANISM: Artificial Sequence
<220> FEATURE:
<223> OTHER INFORMATION: miR185 FDPS sequence #1

<400> SEQUENCE: 10
gggcctggct cgagcagggg gcgagggata ctttctcagc ctccttctgc tggtcccctc    60
cccgcagaag gaggctgaga aagtccttcc ctcccaatga ccgcgtcttc gtcg    114

<210> SEQ ID NO 11
<211> LENGTH: 228
<212> TYPE: DNA
<213> ORGANISM: Artificial Sequence
<220> FEATURE:
<223> OTHER INFORMATION: Rous Sarcoma virus (RSV) promoter

<400> SEQUENCE: 11
gtagtcttat gcaatactct tgtagtcttg caacatggta acgatgagtt agcaacatgc    60
cttacaagga gagaaaaagc accgtgcatg ccgattggtg gaagtaaggt ggtacgatcg    120
tgccttatta ggaaggcaac agacgggtct gacatggatt ggacgaacca ctgaattgcc    180
gcattgcaga gatattgtat ttaagtgcct agctcgatac aataaacg    228

<210> SEQ ID NO 12
<211> LENGTH: 180
<212> TYPE: DNA
<213> ORGANISM: Artificial Sequence
<220> FEATURE:
<223> OTHER INFORMATION: 5 Long terminal repeat (LTR)

<400> SEQUENCE: 12
ggtctctctg gttagaccag atctgagcct gggagctctc tggctaacta gggaacccac    60
tgcttaagcc tcaataaagc ttgccttgag tgcttcaagt agtgtgtgcc cgtctgttgt    120
gtgactctgg taactagaga tccctcagac ccttttagtc agtgtggaaa atctctagca    180

<210> SEQ ID NO 13
<211> LENGTH: 41
<212> TYPE: DNA
<213> ORGANISM: Artificial Sequence
<220> FEATURE:

<223> OTHER INFORMATION: Psi Packaging signal

<400> SEQUENCE: 13
tacgccaaaa attttgacta gcggaggcta aaggagaga g                    41

<210> SEQ ID NO 14
<211> LENGTH: 233
<212> TYPE: DNA
<213> ORGANISM: Artificial Sequence
<220> FEATURE:
<223> OTHER INFORMATION: Rev response element (RRE)

<400> SEQUENCE: 14
aggagctttg ttccttgggt tcttgggagc agcaggaagc actatgggcg cagcctcaat     60
gacgctgacg gtacaggcca gacaattatt gtctggtata gtgcagcagc agaacaattt    120
gctgagggct attgaggcgc aacagcatct gttgcaactc acagtctggg gcatcaagca    180
gctccaggca agaatcctgg ctgtggaaag atacctaaag gatcaacagc tcc           233

<210> SEQ ID NO 15
<211> LENGTH: 118
<212> TYPE: DNA
<213> ORGANISM: Artificial Sequence
<220> FEATURE:
<223> OTHER INFORMATION: Central polypurine tract (cPPT)

<400> SEQUENCE: 15
ttttaaaaga aaggggggga ttggggggta cagtgcaggg gaaagaatag tagacataat     60
agcaacagac atacaaacta agaattaca aaaacaaatt acaaaattca aaatttta      118

<210> SEQ ID NO 16
<211> LENGTH: 217
<212> TYPE: DNA
<213> ORGANISM: Artificial Sequence
<220> FEATURE:
<223> OTHER INFORMATION: Polymerase III shRNA promoters- H1 promoter

<400> SEQUENCE: 16
gaacgctgac gtcatcaacc cgctccaagg aatcgcgggc ccagtgtcac taggcgggaa     60
cacccagcgc gcgtgcgccc tggcaggaag atggctgtga gggacagggg agtggcgccc    120
tgcaatattt gcatgtcgct atgtgttctg ggaaatcacc ataaacgtga atgtctttg    180 gatttgggaa tcttataagt tctgtatgag accactt                           217

<210> SEQ ID NO 17
<211> LENGTH: 590
<212> TYPE: DNA
<213> ORGANISM: Artificial Sequence
<220> FEATURE:
<223> OTHER INFORMATION: Long WPRE sequence

<400> SEQUENCE: 17
aatcaacctc tgattacaaa atttgtgaaa gattgactgg tattcttaac tatgttgctc     60
cttttacgct atgtggatac gctgctttaa tgcctttgta tcatgctatt gcttcccgta    120
tggctttcat tttctcctcc ttgtataaat cctggttgct gtctctttat gaggagttgt    180
ggcccgttgt caggcaacgt ggcgtggtgt gcactgtgtt tgctgacgca accccactg    240 gttggggcat tgccaccacc tgtcagctcc tttccgggac tttcgctttc ccctcccta    300 ttgccacggc ggaactcatc gccgcctgcc ttgcccgctg ctggacaggg gctcggctgt    360
tgggcactga caattccgtg gtgttgtcgg ggaaatcatc gtcctttcct ggctgctcg    420

| | |
|---|---|
| cctgtgttgc cacctggatt ctgcgcggga cgtccttctg ctacgtccct tcggccctca | 480 |
| atccagcgga ccttccttcc cgcggcctgc tgccggctct gcggcctctt ccgcgtcttc | 540 |
| gccttcgccc tcagacgagt cggatctccc tttgggccgc ctccccgcct | 590 |

<210> SEQ ID NO 18
<211> LENGTH: 250
<212> TYPE: DNA
<213> ORGANISM: Artificial Sequence
<220> FEATURE:
<223> OTHER INFORMATION: 3 delta LTR

<400> SEQUENCE: 18

| | |
|---|---|
| tggaagggct aattcactcc caacgaagat aagatctgct ttttgcttgt actgggtctc | 60 |
| tctggttaga ccagatctga gcctgggagc tctctggcta actagggaac ccactgctta | 120 |
| agcctcaata aagcttgcct tgagtgcttc aagtagtgtg tgcccgtctg ttgtgtgact | 180 |
| ctggtaacta gagatccctc agaccctttt agtcagtgtg aaaatctct agcagtagta | 240 |
| gttcatgtca | 250 |

<210> SEQ ID NO 19
<211> LENGTH: 290
<212> TYPE: DNA
<213> ORGANISM: Artificial Sequence
<220> FEATURE:
<223> OTHER INFORMATION: Helper/Rev- Chicken beta actin (CAG) promoter-
    Transcription

<400> SEQUENCE: 19

| | |
|---|---|
| gctattacca tgggtcgagg tgagccccac gttctgcttc actctcccca tctccccccc | 60 |
| ctccccaccc ccaattttgt atttatttat tttttaatta ttttgtgcag cgatgggggc | 120 |
| gggggggggg gggcgcgcg ccaggcgggg cggggcgggg cgaggggcgg ggcggggcga | 180 |
| ggcggagagg tgcggcggca gccaatcaga gcggcgcgct ccgaaagttt ccttttatgg | 240 |
| cgaggcggcg gcggcggcgg ccctataaaa agcgaagcgc gcggcgggcg | 290 |

<210> SEQ ID NO 20
<211> LENGTH: 1503
<212> TYPE: DNA
<213> ORGANISM: Artificial Sequence
<220> FEATURE:
<223> OTHER INFORMATION: Helper/Rev- HIV Gag- Viral capsid

<400> SEQUENCE: 20

| | |
|---|---|
| atgggtgcga gagcgtcagt attaagcggg ggagaattag atcgatggga aaaaattcgg | 60 |
| ttaaggccag ggggaaagaa aaaatataaa ttaaaacata tagtatgggc aagcagggag | 120 |
| ctagaacgat tcgcagttaa tcctggcctg ttagaaacat cagaaggctg tagacaaata | 180 |
| ctgggacagc tacaaccatc ccttcagaca ggatcagaag aacttagatc attatataat | 240 |
| acagtagcaa ccctctattg tgtgcatcaa aggatagaga taaaagacac caaggaagct | 300 |
| ttagacaaga tagaggaaga gcaaaacaaa agtaagaaaa agcacagca agcagcagct | 360 |
| gacacaggac acagcaatca ggtcagccaa aattacccta gtgtcagaa catccagggg | 420 |
| caaatggtac atcaggccat atcacctaga actttaaatg catgggtaaa agtagtagaa | 480 |
| gagaaggctt tcagcccaga agtgataccc atgttttcag cattatcaga aggagccacc | 540 |
| ccacaagatt taaacaccat gctaaacaca gtggggggga tcaagcagc catgcaaatg | 600 |
| ttaaaagaga ccatcaatga ggaagctgca gaatgggata gagtgcatcc agtgcatgca | 660 |

```
gggcctattg caccaggcca gatgagagaa ccaaggggaa gtgacatagc aggaactact    720
agtacccttc aggaacaaat aggatggatg acacataatc cacctatccc agtaggagaa    780
atctataaaa gatggataat cctgggatta aataaaatag taagaatgta tagccctacc    840
agcattctgg acataagaca aggaccaaag gaacccttta gagactatgt agaccgattc    900
tataaaactc taagagccga gcaagcttca caagaggtaa aaaattggat gacagaaacc    960
ttgttggtcc aaaatgcgaa cccagattgt aagactattt taaaagcatt gggaccagga   1020
gcgacactag aagaaatgat gacagcatgt cagggagtgg ggggacccgg ccataaagca   1080
agagttttgg ctgaagcaat gagccaagta acaaatccag ctaccataat gatacagaaa   1140
ggcaatttta ggaaccaaag aaagactgtt aagtgtttca attgtggcaa agaagggcac   1200
atagccaaaa attgcagggc ccctaggaaa aagggctgtt ggaaatgtgg aaaggaagga   1260
caccaaatga aagattgtac tgagagacag gctaattttt tagggaagat ctggccttcc   1320
cacaagggaa ggccagggaa ttttcttcag agcagaccag agccaacagc cccaccagaa   1380
gagagcttca ggtttgggga agacaaca actccctctc agaagcagga gccgatagac   1440
aaggaactgt atcctttagc ttccctcaga tcactctttg gcagcgaccc ctcgtcacaa   1500
taa                                                                 1503

<210> SEQ ID NO 21
<211> LENGTH: 1872
<212> TYPE: DNA
<213> ORGANISM: Artificial Sequence
<220> FEATURE:
<223> OTHER INFORMATION: Helper/Rev- HIV Pol- Protease and reverse
      transcriptase

<400> SEQUENCE: 21
atgaatttgc caggaagatg gaaaccaaaa atgataggggg gaattggagg ttttatcaaa     60
gtaggacagt atgatcagat actcatagaa atctgcggac ataaagctat aggtacagta    120
ttagtaggac ctacacctgt caacataatt ggaagaaatc tgttgactca gattggctgc    180
actttaaatt ttcccattag tcctattgag actgtaccag taaaattaaa gccaggaatg    240
gatggcccaa aagttaaaca atggccattg acagaagaaa aaataaaagc attagtagaa    300
atttgtacag aaatggaaaa ggaaggaaaa atttcaaaaa ttgggcctga aaatccatac    360
aatactccag tatttgccat aaagaaaaaa gacagtacta atggagaaaa attagtagat    420
ttcagagaac ttaataagag aactcaagat ttctgggaag ttcaattagg aataccacat    480
cctgcagggt taaaacagaa aaaatcagta acagtactgg atgtgggcga tgcatatttt    540
tcagttccct tagataaaga cttcaggaag tatactgcat ttaccatacc tagtataaac    600
aatgagacac cagggattag atatcagtac aatgtgcttc cacagggatg gaaaggatca    660
ccagcaatat tccagtgtag catgacaaaa atcttagagc cttttagaaa acaaaatcca    720
gacatagtca tctatcaata catggatgat ttgtatgtag gatctgactt agaaataggg    780
cagcatagaa caaaaataga ggaactgaga caacatctgt tgaggtgggg atttaccaca    840
ccagacaaaa aacatcagaa agaacctcca ttcctttgga tgggttatga actccatcct    900
gataaatgga cagtacagcc tatagtgctg ccagaaaagg acagctggac tgtcaatgac    960
atacagaaat tagtgggaaa attgaattgg gcaagtcaga tttatgcagg gattaaagta   1020
aggcaattat gtaaacttct taggggaacc aaagcactaa cagaagtagt accactaaca   1080
gaagaagcag agctagaact ggcagaaaac agggagattc taaaagaacc ggtacatgga   1140
```

```
gtgtattatg acccatcaaa agacttaata gcagaaatac agaagcaggg gcaaggccaa    1200
tggacatatc aaatttatca agagccattt aaaaatctga aaacaggaaa atatgcaaga    1260
atgaagggtg cccacactaa tgatgtgaaa caattaacag aggcagtaca aaaaatagcc    1320
acagaaagca tagtaatatg gggaaagact cctaaattta aattacccat acaaaaggaa    1380
acatgggaag catggtggac agagtattgg caagccacct ggattcctga gtgggagttt    1440
gtcaataccc ctcccttagt gaagttatgg taccagttag agaaagaacc cataatagga    1500
gcagaaactt tctatgtaga tggggcagcc aatagggaaa ctaaattagg aaaagcagga    1560
tatgtaactg acagaggaag acaaaaagtt gtccccctaa cggacacaac aaatcagaag    1620
actgagttac aagcaattca tctagctttg caggattcgg gattagaagt aaacatagtg    1680
acagactcac aatatgcatt gggaatcatt caagcacaac cagataagag tgaatcagag    1740
ttagtcagtc aaataataga gcagttaata aaaaaggaaa aagtctacct ggcatgggta    1800
ccagcacaca aaggaattgg aggaaatgaa caagtagatg ggttggtcag tgctggaatc    1860
aggaaagtac ta                                                       1872

<210> SEQ ID NO 22
<211> LENGTH: 867
<212> TYPE: DNA
<213> ORGANISM: Artificial Sequence
<220> FEATURE:
<223> OTHER INFORMATION: Helper Rev- HIV Integrase- Integration of viral
      RNA

<400> SEQUENCE: 22
tttttagatg gaatagataa ggcccaagaa gaacatgaga aatatcacag taattggaga      60
gcaatggcta gtgattttaa cctaccacct gtagtagcaa aagaaatagt agccagctgt     120
gataaatgtc agctaaaagg ggaagccatg catggacaag tagactgtag cccaggaata     180
tggcagctag attgtacaca tttagaagga aaagttatct tggtagcagt tcatgtagcc     240
agtggatata tagaagcaga agtaattcca gcagagacag ggcaagaaac agcatacttc     300
ctcttaaaat tagcaggaag atggccagta aaaacagtac atacagacaa tggcagcaat     360
ttcaccagta ctacagttaa ggccgcctgt tggtgggcgg ggatcaagca ggaatttggc     420
attccctaca atccccaaag tcaaggagta atagaatcta tgaataaaga attaaagaaa     480
attataggac aggtaagaga tcaggctgaa catcttaaga cagcagtaca aatggcagta     540
ttcatccaca attttaaaag aaaagggggg attggggggt acagtgcagg ggaaagaata     600
gtagacataa tagcaacaga catacaaact aaagaattac aaaaacaaat tacaaaaatt     660
caaaattttc gggtttatta cagggacagc agagatccag tttggaaagg accagcaaag     720
ctcctctgga aaggtgaagg ggcagtagta atacaagata atagtgacat aaaagtagtg     780
ccaagaagaa aagcaaagat catcagggat tatggaaaac agatggcagg tgatgattgt     840
gtggcaagta gacaggatga ggattaa                                        867

<210> SEQ ID NO 23
<211> LENGTH: 234
<212> TYPE: DNA
<213> ORGANISM: Artificial Sequence
<220> FEATURE:
<223> OTHER INFORMATION: Helper/Rev- HIV RRE- Binds Rev element

<400> SEQUENCE: 23
aggagctttg ttccttgggt tcttgggagc agcaggaagc actatgggcg cagcgtcaat      60
```

```
gacgctgacg gtacaggcca gacaattatt gtctggtata gtgcagcagc agaacaattt    120
gctgagggct attgaggcgc aacagcatct gttgcaactc acagtctggg gcatcaagca    180
gctccaggca agaatcctgg ctgtggaaag atacctaaag gatcaacagc tcct          234

<210> SEQ ID NO 24
<211> LENGTH: 351
<212> TYPE: DNA
<213> ORGANISM: Artificial Sequence
<220> FEATURE:
<223> OTHER INFORMATION: Helper/Rev- HIV Rev- Nuclear export and
      stabilize viral mRNA

<400> SEQUENCE: 24
atggcaggaa gaagcggaga cagcgacgaa gaactcctca aggcagtcag actcatcaag    60
tttctctatc aaagcaaccc acctcccaat cccgagggga cccgacaggc ccgaaggaat    120
agaagaagaa ggtggagaga gagacagaga cagatccatt cgattagtga acggatcctt    180
agcacttatc tgggacgatc tgcggagcct gtgcctcttc agctaccacc gcttgagaga    240
cttactcttg attgtaacga ggattgtgga acttctggga cgcaggggt gggaagccct    300 caaatattgg tggaatctcc tacaatattg gagtcaggag ctaaagaata g             351

<210> SEQ ID NO 25
<211> LENGTH: 577
<212> TYPE: DNA
<213> ORGANISM: Artificial Sequence
<220> FEATURE:
<223> OTHER INFORMATION: Envelope- CMV promoter- Transcription

<400> SEQUENCE: 25
acattgatta ttgactagtt attaatagta atcaattacg gggtcattag ttcatagccc    60
atatatggag ttccgcgtta cataacttac ggtaaatggc ccgcctggct gaccgcccaa    120
cgacccccgc ccattgacgt caataatgac gtatgttccc atagtaacgc caatagggac    180
tttccattga cgtcaatggg tggagtattt acggtaaact gcccacttgg cagtacatca    240
agtgtatcat atgccaagta cgccccctat tgacgtcaat gacggtaaat ggcccgcctg    300
gcattatgcc cagtacatga ccttatggga cttttcctact tggcagtaca tctacgtatt    360
agtcatcgct attaccatgg tgatgcggtt ttggcagtac atcaatgggc gtggatagcg    420
gtttgactca cggggatttc caagtctcca ccccattgac gtcaatggga gtttgttttg    480
gcaccaaaat caacgggact ttccaaaatg tcgtaacaac tccgccccat tgacgcaaat    540
gggcggtagg cgtgtacggt gggaggtcta tataagc                             577

<210> SEQ ID NO 26
<211> LENGTH: 1519
<212> TYPE: DNA
<213> ORGANISM: Artificial Sequence
<220> FEATURE:
<223> OTHER INFORMATION: Envelope- VSV-G- Glycoprotein envelope-cell
      entry

<400> SEQUENCE: 26
atgaagtgcc ttttgtactt agccttttta ttcattgggg tgaattgcaa gttcaccata    60 gttttttccac acaaccaaaa aggaaactgg aaaaatgttc cttctaatta ccattattgc    120
ccgtcaagct cagatttaaa ttggcataat gacttaatag gcacagcctt acaagtcaaa    180
atgcccaaga gtcacaaggc tattcaagca gacggttgga tgtgtcatgc ttccaaatgg    240
```

```
gtcactactt gtgatttccg ctggtatgga ccgaagtata taacacattc catccgatcc    300
ttcactccat ctgtagaaca atgcaaggaa agcattgaac aaacgaaaca aggaacttgg    360
ctgaatccag gcttccctcc tcaaagttgt ggatatgcaa ctgtgacgga tgccgaagca    420
gtgattgtcc aggtgactcc tcaccatgtg ctggttgatg aatacacagg agaatgggtt    480
gattcacagt tcatcaacgg aaaatgcagc aattacatat gccccactgt ccataactct    540
acaacctggc attctgacta taaggtcaaa gggctatgtg attctaacct catttccatg    600
gacatcacct tcttctcaga ggacggagag ctatcatccc tgggaaagga gggcacaggg    660
ttcagaagta actactttgc ttatgaaact ggaggcaagg cctgcaaaat gcaatactgc    720
aagcattggg gagtcagact cccatcaggt gtctggttcg agatggctga taaggatctc    780
tttgctgcag ccagattccc tgaatgccca gaagggtcaa gtatctctgc tccatctcag    840
acctcagtgg atgtaagtct aattcaggac gttgagagga tcttggatta ttccctctgc    900
caagaaacct ggagcaaaat cagagcgggt cttccaatct ctccagtgga tctcagctat    960
cttgctccta aaaacccagg aaccggtcct gctttcacca taatcaatgg tacccctaaaa   1020 tactttgaga ccagatacat cagagtcgat attgctgctc caatcctctc aagaatggtc   1080
ggaatgatca gtgaactac cacagaaagg gaactgtggg atgactgggc accatatgaa   1140
gacgtggaaa ttggacccaa tggagttctg aggaccagtt caggatataa gtttccttta   1200
tacatgattg gacatggtat gttggactcc gatcttcatc ttagctcaaa ggctcaggtg   1260
ttcgaacatc ctcacattca agacgctgct tcgcaacttc ctgatgatga gagtttattt   1320
tttggtgata ctgggctatc caaaaatcca atcgagcttg tagaaggttg gttcagtagt   1380
tggaaaagct ctattgcctc ttttttcttt atcatagggt taatcattgg actattcttg   1440
gttctccgag ttggtatcca tctttgcatt aaattaaagc acaccaagaa aagacagatt   1500
tatacagaca tagagatga                                                 1519
```

<210> SEQ ID NO 27
<211> LENGTH: 352
<212> TYPE: DNA
<213> ORGANISM: Artificial Sequence
<220> FEATURE:
<223> OTHER INFORMATION: Helper/Rev- CMV early (CAG) enhancer-
      EnhanceTranscription

<400> SEQUENCE: 27

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggac tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tc            352
```

<210> SEQ ID NO 28
<211> LENGTH: 960
<212> TYPE: DNA
<213> ORGANISM: Artificial Sequence
<220> FEATURE:
<223> OTHER INFORMATION: Helper/Rev- Chicken beta actin intron- Enhance
      gene expression

<400> SEQUENCE: 28

```
ggagtcgctg cgttgccttc gccccgtgcc ccgctccgcg ccgcctcgcg ccgcccgccc     60
```

```
cggctctgac tgaccgcgtt actcccacag gtgagcgggc gggacggccc ttctcctccg      120
ggctgtaatt agcgcttggt ttaatgacgg ctcgtttctt ttctgtggct gcgtgaaagc      180
cttaaagggc tccgggaggg ccctttgtgc ggggggggagc ggctcggggg gtgcgtgcgt    240
gtgtgtgtgc gtggggagcg ccgcgtgcgg cccgcgctgc ccggcggctg tgagcgctgc    300
gggcgcggcg cggggctttg tgcgctccgc gtgtgcgcga ggggagcgcg gccggggcg      360 gtgccccgcg gtgcgggggg gctgcgaggg gaacaaaggc tgcgtgcggg gtgtgtgcgt    420 ggggggggtga gcaggggggtg tgggcgcggc ggtcgggctg taaccccccc ctgcaccccc    480
ctccccgagt tgctgagcac ggcccggctt cgggtgcggg gctccgtgcg gggcgtggcg    540
cggggctcgc cgtgccgggc gggggggtggc ggcaggtggg ggtgccgggc ggggcggggc    600
cgcctcgggc cggggagggc tcggggggagg ggcgcggcgg ccccggagcg ccggcggctg    660
tcgaggcgcg gcgagccgca gccattgcct tttatggtaa tcgtgcgaga gggcgcaggg    720
acttcctttg tcccaaatct ggcggagccg aaatctggga ggcgccgccg caccccctct    780
agcgggcgcg ggcgaagcgg tgcggcgccg gcaggaagga aatgggcggg gagggccttc    840
gtgcgtcgcc gcgccgccgt ccccttctcc atctccagcc tcggggctgc cgcaggggga    900
cggctgcctt cgggggggac ggggcagggc ggggttcggc ttctggcgtg tgaccggcgg    960

<210> SEQ ID NO 29
<211> LENGTH: 448
<212> TYPE: DNA
<213> ORGANISM: Artificial Sequence
<220> FEATURE:
<223> OTHER INFORMATION: Helper/Rev- Rabbit beta globin poly A- RNA
      stability

<400> SEQUENCE: 29 agatctttt cccctctgcca aaaattatgg ggacatcatg aagccccttg agcatctgac      60
ttctggctaa taaaggaaat ttattttcat tgcaatagtg tgttggaatt ttttgtgtct    120
ctcactcgga aggacatatg ggagggcaaa tcatttaaaa catcagaatg agtatttggt    180
ttagagtttg gcaacatatg ccatatgctg gctgccatga acaaaggtgg ctataaagag    240
gtcatcagta tatgaaacag ccccctgctg tccattcctt attccataga aaagccttga    300
cttgaggtta gatttttttt atattttgtt ttgtgttatt tttttctta acatccctaa      360 aattttcctt acatgtttta ctagccagat ttttcctcct ctcctgacta ctcccagtca    420
tagctgtccc tcttctctta tgaagatc                                        448

<210> SEQ ID NO 30
<211> LENGTH: 573
<212> TYPE: DNA
<213> ORGANISM: Artificial Sequence
<220> FEATURE:
<223> OTHER INFORMATION: Envelope- Beta globin intron- Enhance gene
      expression

<400> SEQUENCE: 30
gtgagtttgg ggacccttga ttgttctttc ttttttcgcta ttgtaaaatt catgttatat      60
ggagggggca aagttttcag ggtgttgttt agaatgggaa gatgtccctt gtatcaccat    120
ggaccctcat gataaatttg tttctttcac tttctactct gttgacaacc attgtctcct    180 cttatttttct tttcattttc tgtaacttttt tcgttaaact ttagcttgca tttgtaacga    240 attttttaaat tcacttttgt ttatttgtca gattgtaagt actttctcta atcacttttt    300
```

```
tttcaaggca atcagggtat attatattgt acttcagcac agttttagag aacaattgtt    360
ataattaaat gataaggtag aatatttctg catataaatt ctggctggcg tggaaatatt    420
cttattggta gaaacaacta caccctggtc atcatcctgc ctttctcttt atggttacaa    480
tgatatacac tgtttgagat gaggataaaa tactctgagt ccaaaccggg cccctctgct    540
aaccatgttc atgccttctt ctctttccta cag                                 573
```

<210> SEQ ID NO 31
<211> LENGTH: 450
<212> TYPE: DNA
<213> ORGANISM: Artificial Sequence
<220> FEATURE:
<223> OTHER INFORMATION: Envelope- Rabbit beta globin poly A- RNA
      stability

<400> SEQUENCE: 31

```
agatcttttt ccctctgcca aaaattatgg ggacatcatg aagccccttg agcatctgac     60
ttctggctaa taaggaaat ttattttcat tgcaatagtg tgttggaatt ttttgtgtct    120
ctcactcgga aggacatatg ggagggcaaa tcatttaaaa catcagaatg agtatttggt    180
ttagagtttg gcaacatatg cccatatgct ggctgccatg aacaaaggtt ggctataaag    240
aggtcatcag tatatgaaac agccccctgc tgtccattcc ttattccata gaaaagcctt    300
gacttgaggt tagatttttt ttatattttg tttgtgtta ttttttttctt taacatccct    360 aaaattttcc ttacatgttt tactagccag attttttcctc ctctcctgac tactcccagt    420
catagctgtc cctcttctct tatggagatc                                    450
```

<210> SEQ ID NO 32
<211> LENGTH: 31
<212> TYPE: DNA
<213> ORGANISM: Artificial Sequence
<220> FEATURE:
<223> OTHER INFORMATION: Primer

<400> SEQUENCE: 32

```
taagcagaat tcatgaattt gccaggaaga t                                   31
```

<210> SEQ ID NO 33
<211> LENGTH: 36
<212> TYPE: DNA
<213> ORGANISM: Artificial Sequence
<220> FEATURE:
<223> OTHER INFORMATION: Primer

<400> SEQUENCE: 33

```
ccatacaatg aatggacact aggcggccgc acgaat                              36
```

<210> SEQ ID NO 34
<211> LENGTH: 2745
<212> TYPE: DNA
<213> ORGANISM: Artificial Sequence
<220> FEATURE:
<223> OTHER INFORMATION: Gag, Pol, Integrase fragment

<400> SEQUENCE: 34

```
gaattcatga atttgccagg aagatggaaa ccaaaaatga tagggggaat tggaggtttt     60
atcaaagtaa gacagtatga tcagatactc atagaaatct gcggacataa agctataggt    120
acagtattag taggacctac acctgtcaac ataattggaa gaaatctgtt gactcagatt    180
ggctgcactt taaattttcc cattagtcct attgagactg taccagtaaa attaaagcca    240
```

```
ggaatggatg gcccaaaagt taaacaatgg ccattgacag aagaaaaaat aaaagcatta       300
gtagaaattt gtacagaaat ggaaaaggaa ggaaaaattt caaaaattgg gcctgaaaat       360
ccatacaata ctccagtatt tgccataaag aaaaaagaca gtactaaatg gagaaaatta       420
gtagatttca gagaacttaa taagagaact caagatttct gggaagttca attaggaata       480
ccacatcctg cagggttaaa acagaaaaaa tcagtaacag tactggatgt gggcgatgca       540
tatttttcag ttcccttaga taaagacttc aggaagtata ctgcatttac catacctagt       600
ataaacaatg agacaccagg gattagatat cagtacaatg tgcttccaca gggatggaaa       660
ggatcaccag caatattcca gtgtagcatg acaaaaatct tagagccttt tagaaaacaa       720
aatccagaca tagtcatcta tcaatacatg gatgatttgt atgtaggatc tgacttagaa       780
atagggcagc atagaacaaa aatagaggaa ctgagacaac atctgttgag gtggggattt       840
accacaccag acaaaaaaca tcagaaagaa cctccattcc tttggatggg ttatgaactc       900
catcctgata atggacagt acagcctata gtgctgccag aaaaggacag ctggactgtc       960
aatgacatac agaaattagt gggaaaattg aattgggcaa gtcagattta tgcagggatt      1020
aaagtaaggc aattatgtaa acttcttagg ggaaccaaag cactaacaga agtagtacca      1080
ctaacagaag aagcagagct agaactggca gaaaacaggg agattctaaa agaaccggta      1140
catggagtgt attatgaccc atcaaaagac ttaatagcag aaatacagaa gcaggggcaa      1200
ggccaatgga catatcaaat ttatcaagag ccatttaaaa atctgaaaac aggaaagtat      1260
gcaagaatga agggtgccca cactaatgat gtgaaacaat taacagaggc agtacaaaaa      1320
atagccacag aaagcatagt aatatgggga aagactccta aatttaaatt acccatacaa      1380
aaggaaacat gggaagcatg gtggacagag tattggcaag ccacctggat tcctgagtgg      1440
gagtttgtca atacccctcc cttagtgaag ttatggtacc agttagaaa agaacccata       1500 ataggagcag aaactttcta tgtagatggg gcagccaata gggaaactaa attaggaaaa      1560
gcaggatatg taactgacag aggaagacaa aaagttgtcc ccctaacgga cacaacaaat      1620
cagaagactg agttacaagc aattcatcta gctttgcagg attcgggatt agaagtaaac      1680
atagtgacag actcacaata tgcattggga atcattcaag cacaaccaga taagagtgaa      1740
tcagagttag tcagtcaaat aatagagcag ttaataaaaa aggaaaaagt ctacctggca      1800
tgggtaccag cacacaaagg aattggagga aatgaacaag tagataaatt ggtcagtgct      1860
ggaatcagga aagtactatt tttagatgga atagataagg cccaagaaga acatgagaaa      1920
tatcacagta attggagagc aatggctagt gattttaacc taccacctgt agtagcaaaa      1980
gaaatagtag ccagctgtga taaatgtcag ctaaaggggg aagccatgca tggacaagta      2040
gactgtagcc caggaatatg gcagctagat tgtacacatt tagaaggaaa agttatcttg      2100
gtagcagttc atgtagccag tggatatata gaagcagaag taattccagc agagacaggg      2160
caagaaacag catacttcct cttaaaatta gcaggaagat ggccagtaaa aacagtacat      2220
acagacaatg gcagcaattt caccagtact acagttaagg ccgcctgttg gtgggcgggg      2280
atcaagcagg aatttggcat tccctacaat ccccaaagtc aaggagtaat agaatctatg      2340
aataaagaat taaagaaaat tataggacag gtaagagatc aggctgaaca tcttaagaca      2400
gcagtacaaa tggcagtatt catccacaat tttaaaagaa aaggggggat tggggggtac      2460
agtgcagggg aaagaatagt agacataata gcaacagaca tacaaactaa agaattacaa      2520
aaacaaatta caaaaattca aaattttcgg gtttattaca gggacagcag agatccagtt      2580
tggaaaggac cagcaaagct cctctggaaa ggtgaagggg cagtagtaat acaagataat      2640
```

```
agtgacataa aagtagtgcc aagaagaaaa gcaaagatca tcagggatta tggaaaacag    2700
atggcaggtg atgattgtgt ggcaagtaga caggatgagg attaa                    2745
```

<210> SEQ ID NO 35
<211> LENGTH: 1586
<212> TYPE: DNA
<213> ORGANISM: Artificial Sequence
<220> FEATURE:
<223> OTHER INFORMATION: DNA Fragment containing Rev, RRE and rabbit
      beta globin poly A

<400> SEQUENCE: 35

```
tctagaatgg caggaagaag cggagacagc gacgaagagc tcatcagaac agtcagactc      60
atcaagcttc tctatcaaag caacccacct cccaatcccg aggggacccg acaggcccga     120
aggaatagaa gaagaaggtg gagagagaga cagagacaga tccattcgat tagtgaacgg     180
atccttggca cttatctggg acgatctgcg gagcctgtgc ctcttcagct accaccgctt     240
gagagactta ctcttgattg taacgaggat tgtggaactt ctgggacgca gggggtggga     300
agccctcaaa tattggtgga atctcctaca atattggagt caggagctaa gaatagagg     360 agctttgttc cttgggttct tgggagcagc aggaagcact atgggcgcag cgtcaatgac     420
gctgacggta caggccagac aattattgtc tggtatagtg cagcagcaga caatttgct     480 gagggctatt gaggcgcaac agcatctgtt gcaactcaca gtctggggca tcaagcagct     540
ccaggcaaga atcctggctg tggaaagata cctaaaggat caacagctcc tagatctttt     600
tccctctgcc aaaaattatg gggacatcat gaagccccctt gagcatctga cttctggcta     660
ataaaggaaa tttattttca ttgcaatagt gtgttggaat ttttgtgtc tctcactcgg     720 aaggacatat gggagggcaa atcatttaaa acatcagaat gagtatttgg tttagagttt     780
ggcaacatat gccatatgct ggctgccatg aacaaaggtg gctataaaga ggtcatcagt     840
atatgaaaca gccccctgct gtccattcct tattccatag aaaagccttg acttgaggtt     900 agatttttttt tatatttgt tttgtgttat ttttttcttt aacatcccta aaattttcct     960
tacatgtttt actagccaga ttttttcctcc tctcctgact actcccagtc atagctgtcc    1020
ctcttctctt atgaagatcc ctcgacctgc agcccaagct tggcgtaatc atggtcatag    1080
ctgtttcctg tgtgaaattg ttatccgctc acaattccac acaacatacg agccggaagc    1140
ataaagtgta aagcctgggg tgcctaatga gtgagctaac tcacattaat tgcgttgcgc    1200
tcactgcccg ctttccagtc gggaaacctg tcgtgccagc ggatccgcat ctcaattagt    1260
cagcaaccat agtcccgccc ctaactccgc ccatcccgcc cctaactccg cccagttccg    1320
cccattctcc gccccatggc tgactaattt ttttttattta tgcagaggcc gaggccgcct    1380
cggcctctga gctattccag aagtagtgag gaggcttttt tggaggccta ggcttttgca    1440
aaaagctaac ttgtttattg cagcttataa tggttacaaa taaagcaata gcatcacaaa    1500
tttcacaaat aaagcatttt tttcactgca ttctagttgt ggtttgtcca aactcatcaa    1560
tgtatcttat cagcggccgc cccggg                                         1586
```

<210> SEQ ID NO 36
<211> LENGTH: 1614
<212> TYPE: DNA
<213> ORGANISM: Artificial Sequence
<220> FEATURE:
<223> OTHER INFORMATION: DNA fragment containing the CAG
      enhancer/promoter/intron sequence

<400> SEQUENCE: 36

```
acgcgttagt tattaatagt aatcaattac ggggtcatta gttcatagcc catatatgga      60
gttccgcgtt acataactta cggtaaatgg cccgcctggc tgaccgccca acgaccccg      120
cccattgacg tcaataatga cgtatgttcc catagtaacg ccaataggga ctttccattg     180
acgtcaatgg gtggactatt tacggtaaac tgcccacttg gcagtacatc aagtgtatca    240
tatgccaagt acgcccccta ttgacgtcaa tgacggtaaa tggcccgcct ggcattatgc    300
ccagtacatg accttatggg actttcctac ttggcagtac atctacgtat tagtcatcgc    360
tattaccatg gtcgaggtg agccccacgt tctgcttcac tctccccatc tcccccccct    420
ccccaccccc aattttgtat ttatttattt tttaattatt ttgtgcagcg atgggggcgg    480
ggggggggg gcgcgcgcc aggcggggcg gggcggggcg aggggcgggg cggggcgagg    540
cggagaggtg cggcggcagc caatcagagc ggcgcgctcc gaaagtttcc ttttatggcg    600
aggcggcggc ggcggcggcc ctataaaaag cgaagcgcgc ggcgggcggg agtcgctgcg    660
ttgccttcgc cccgtgcccc gctccgcgcc gcctcgcgcc gcccgcccg gctctgactg    720
accgcgttac tcccacaggt gagcgggcgg gacggccctt ctcctccggg ctgtaattag    780
cgcttggttt aatgacggct cgtttctttt ctgtggctgc gtgaaagcct taaagggctc    840
cgggagggcc ctttgtgcgg gggagcgg ctcgggggt gcgtgcgtgt gtgtgtgcgt    900
ggggagcgcc gcgtgcggcc cgcgctgccc ggcggctgtg agcgctgcgg gcgcggcgcg    960
gggctttgtg cgctccgcgt gtgcgcgagg ggagcgcggc cggggcggt gcccgcggt    1020
gcgggggggc tgcgagggga acaaaggctg cgtgcgggt gtgtgcgtgg gggggtgagc   1080
aggggggtgtg ggcgcggcgg tcgggctgta accccccct gcaccccct ccccgagttg   1140
ctgagcacgg cccggcttcg ggtgcgggc tccgtgcggg gcgtggcgcg gggctcgccg   1200
tgccgggcgg ggggtggcgg caggtggggg tgccgggcgg ggcggggccg cctcgggccg   1260
gggagggctc gggggagggg cgcggcgccc ccggagcgcc ggcggctgtc gaggcgcggc   1320
gagccgcagc cattgccttt tatggtaatc gtgcgagagg gcgcagggac ttcctttgtc   1380
ccaaatctgg cggagccgaa atctgggagg cgccgccgca ccccctctag cgggcgcggg   1440
cgaagcggtg cggcgccggc aggaaggaaa tgggcgggga gggccttcgt gcgtcgccgc   1500
gccgccgtcc ccttctccat ctccagcctc ggggctgccg caggggacg gctgccttcg   1560
gggggacgg ggcagggcgg ggttcggctt ctggcgtgtg accggcggga attc            1614
```

<210> SEQ ID NO 37
<211> LENGTH: 1531
<212> TYPE: DNA
<213> ORGANISM: Artificial Sequence
<220> FEATURE:
<223> OTHER INFORMATION: DNA fragment containing VSV-G

<400> SEQUENCE: 37

```
gaattcatga agtgcctttt gtacttagcc ttttttattca ttggggtgaa ttgcaagttc      60
accatagttt ttccacacaa ccaaaaagga aactggaaaa atgttccttc taattaccat    120
tattgcccgt caagctcaga tttaaattgg cataatgact aataggcac agccttacaa    180
gtcaaaatgc ccaagagtca caaggctatt caagcagacg gttggatgtg tcatgcttcc    240
aaatgggtca ctacttgtga tttccgctgg tatggaccga agtatataac acattccatc    300
cgatccttca ctccatctgt agaacaatgc aaggaaagca ttgaacaaac gaaacaagga    360
acttggctga atccaggctt ccctcctcaa agttgtggat atgcaactgt gacggatgcc    420
```

```
gaagcagtga ttgtccaggt gactcctcac catgtgctgg ttgatgaata cacaggagaa    480
tgggttgatt cacagttcat caacggaaaa tgcagcaatt acatatgccc cactgtccat    540
aactctacaa cctggcattc tgactataag gtcaaagggc tatgtgattc taacctcatt    600
tccatggaca tcaccttctt ctcagaggac ggagagctat catccctggg aaaggagggc    660
acagggttca gaagtaacta ctttgcttat gaaactggag gcaaggcctg caaaatgcaa    720
tactgcaagc attggggagt cagactccca tcaggtgtct ggttcgagat ggctgataag    780
gatctctttg ctgcagccag attccctgaa tgcccagaag ggtcaagtat ctctgctcca    840
tctcagacct cagtggatgt aagtctaatt caggacgttg agaggatctt ggattattcc    900
ctctgccaag aaacctggag caaaatcaga gcgggtcttc caatctctcc agtggatctc    960
agctatcttg ctcctaaaaa cccaggaacc ggtcctgctt tcaccataat caatggtacc   1020
ctaaaatact ttgagaccag atacatcaga gtcgatattg ctgctccaat cctctcaaga   1080
atggtcggaa tgatcagtgg aactaccaca gaaagggaac tgtgggatga ctgggcacca   1140
tatgaagacg tggaaattgg acccaatgga gttctgagga ccagttcagg atataagttt   1200
cctttataca tgattggaca tggtatgttg gactccgatc ttcatcttag ctcaaaggct   1260
caggtgttcg aacatcctca cattcaagac gctgcttcgc aacttcctga tgatgagagt   1320 ttatttttg gtgatactgg gctatccaaa aatccaatcg agcttgtaga aggttggttc   1380
agtagttgga aaagctctat tgcctctttt ttctttatca tagggttaat cattggacta   1440
ttcttggttc tccgagttgg tatccatctt tgcattaaat taaagcacac caagaaaaga   1500
cagatttata cagacataga gatgagaatt c                                  1531

<210> SEQ ID NO 38
<211> LENGTH: 351
<212> TYPE: DNA
<213> ORGANISM: Artificial Sequence
<220> FEATURE:
<223> OTHER INFORMATION: Rev- RSV promoter- Transcription

<400> SEQUENCE: 38
atggcaggaa gaagcggaga cagcgacgaa gaactcctca aggcagtcag actcatcaag     60
tttctctatc aaagcaaccc acctcccaat cccgagggga cccgacaggc ccgaaggaat    120
agaagaagaa ggtggagaga gagacagaga cagatccatt cgattagtga acggatcctt    180
agcacttatc tgggacgatc tgcggagcct gtgcctcttc agctaccacc gcttgagaga    240
cttactcttg attgtaacga ggattgtgga acttctggga cgcaggggt gggaagcccct    300 caaatattgg tggaatctcc tacaatattg gagtcaggag ctaaagaata g             351

<210> SEQ ID NO 39
<211> LENGTH: 351
<212> TYPE: DNA
<213> ORGANISM: Artificial Sequence
<220> FEATURE:
<223> OTHER INFORMATION: Rev- HIV Rev- Nuclear export and stabilize
      viral mRNA

<400> SEQUENCE: 39
atggcaggaa gaagcggaga cagcgacgaa gaactcctca aggcagtcag actcatcaag     60
tttctctatc aaagcaaccc acctcccaat cccgagggga cccgacaggc ccgaaggaat    120
agaagaagaa ggtggagaga gagacagaga cagatccatt cgattagtga acggatcctt    180
agcacttatc tgggacgatc tgcggagcct gtgcctcttc agctaccacc gcttgagaga    240
```

```
cttactcttg attgtaacga ggattgtgga acttctggga cgcagggggt gggaagccct    300
caaatattgg tggaatctcc tacaatattg gagtcaggag ctaaagaata g             351

<210> SEQ ID NO 40
<211> LENGTH: 884
<212> TYPE: DNA
<213> ORGANISM: Artificial Sequence
<220> FEATURE:
<223> OTHER INFORMATION: RSV promoter and HIV Rev

<400> SEQUENCE: 40
caattgcgat gtacgggcca gatatacgcg tatctgaggg gactagggtg tgtttaggcg     60
aaaagcgggg cttcggttgt acgcggttag gagtcccctc aggatatagt agtttcgctt   120
ttgcataggg aggggaaat gtagtcttat gcaatacact tgtagtcttg caacatggta    180
acgatgagtt agcaacatgc cttacaagga gagaaaaagc accgtgcatg ccgattggtg   240
gaagtaaggt ggtacgatcg tgccttatta ggaaggcaac agacaggtct gacatggatt   300
ggacgaacca ctgaattccg cattgcagag ataattgtat ttaagtgcct agctcgatac   360
aataaacgcc atttgaccat tcaccacatt ggtgtgcacc tccaagctcg agctcgttta   420
gtgaaccgtc agatcgcctg gagacgccat ccacgctgtt ttgacctcca tagaagacac   480
cgggaccgat ccagcctccc ctcgaagcta gcgattaggc atctcctatg caggaagaa    540 gcggagacag cgacgaagaa ctcctcaagg cagtcagact catcaagttt ctctatcaaa   600
gcaacccacc tcccaatccc gaggggaccc gacaggcccg aaggaataga agaagaaggt   660
ggagagagag acagagacag atccattcga ttagtgaacg gatccttagc acttatctgg   720
gacgatctgc ggagcctgtg cctcttcagc taccaccgct tgagagactt actcttgatt   780
gtaacgagga ttgtggaact tctgggacgc agggggtggg aagccctcaa atattggtgg   840
aatctcctac aatattggag tcaggagcta agaatagtc taga                     884

<210> SEQ ID NO 41
<211> LENGTH: 1104
<212> TYPE: DNA
<213> ORGANISM: Artificial Sequence
<220> FEATURE:
<223> OTHER INFORMATION: Elongation Factor-1 alpha (EF1-alpha) promoter

<400> SEQUENCE: 41
ccggtgccta gagaaggtgg cgcggggtaa actgggaaag tgatgtcgtg tactggctcc     60
gcctttttcc cgagggtggg ggagaaccgt atataagtgc agtagtcgcc gtgaacgttc   120
tttttcgcaa cgggtttgcc gccagaacac aggtaagtgc cgtgtgtggt tcccgcgggc   180
ctggcctctt tacgggttat ggcccttgcg tgccttgaat tacttccacg cccctggctg   240
cagtacgtga ttcttgatcc cgagcttcgg gttggaagtg ggtgggagag ttcgaggcct   300
tgcgcttaag gagcccctc gcctcgtgct tgagttgagg cctggcctgg gcgctggggc    360
cgccgcgtgc gaatctggtg gcaccttcgc gcctgtctcg ctgctttcga taagtctcta   420
gccatttaaa attttgatg acctgctgcg acgcttttttt tctggcaaga tagtcttgta    480
aatgcgggcc aagatctgca cactggtatt tcggtttttg gggccgcggg cggcgacggg   540
gcccgtgcgt cccagcgcac atgttcggcg aggcggggcc tgcgagcgcg gccaccgaga   600
atcggacggg ggtagtctca agctggccgg cctgctctgg tgcctggcct cgcgccgccg   660
tgtatcgccc cgccctgggc ggcaaggctg gcccggtcgg caccagttgc gtgagcggaa   720
```

```
agatggccgc ttcccggccc tgctgcaggg agctcaaaat ggaggacgcg gcgctcggga        780
gagcgggcgg gtgagtcacc cacacaaagg aaaagggcct ttccgtcctc agccgtcgct        840
tcatgtgact ccacggagta ccgggcgccg tccaggcacc tcgattagtt ctcgagcttt        900
tggagtacgt cgtctttagg ttgggggggag gggttttatg cgatggagtt tccccacact       960
gagtgggtgg agactgaagt taggccagct tggcacttga tgtaattctc cttggaattt       1020 gcccttttg agtttggatc ttggttcatt ctcaagcctc agacagtggt tcaaagtttt       1080
tttcttccat ttcaggtgtc gtga                                               1104
```

```
<210> SEQ ID NO 42
<211> LENGTH: 511
<212> TYPE: DNA
<213> ORGANISM: Artificial Sequence
<220> FEATURE:
<223> OTHER INFORMATION: Promoter- PGK

<400> SEQUENCE: 42
```

```
ggggttgggg ttgcgccttt tccaaggcag ccctgggttt gcgcagggac gcggctgctc         60
tgggcgtggt tccgggaaac gcagcggcgc cgaccctggg tctcgcacat tcttcacgtc        120
cgttcgcagc gtcaccccgga tcttcgccgc taccccttgtg gccccccgg cgacgcttcc       180 tgctccgccc ctaagtcggg aaggttcctt gcggttcgcg gcgtgccgga cgtgacaaac        240
ggaagccgca cgtctcacta gtaccctcgc agacggacag cgccagggag caatggcagc        300
gcgccgaccg cgatgggctg tggccaatag cggctgctca gcagggcgcg ccgagagcag        360
cggccgggaa ggggcggtgc gggaggcggg gtgtggggcg gtagtgtggg ccctgttcct        420
gcccgcgcgg tgttccgcat tctgcaagcc tccggagcgc acgtcggcag tcggctccct        480
cgttgaccga atcaccgacc tctctcccca g                                       511
```

```
<210> SEQ ID NO 43
<211> LENGTH: 1162
<212> TYPE: DNA
<213> ORGANISM: Artificial Sequence
<220> FEATURE:
<223> OTHER INFORMATION: Promoter- UbC

<400> SEQUENCE: 43
```

```
gcgccgggtt ttggcgcctc ccgcgggcgc cccctcctc acggcgagcg ctgccacgtc          60
agacgaaggg cgcaggagcg ttcctgatcc ttccgcccgg acgctcagga cagcggcccg        120
ctgctcataa gactcggcct tagaaccca gtatcagcag aaggacattt taggacggga        180
cttgggtgac tctagggcac tggttttctt tccagagagc ggaacaggcg aggaaaagta        240
gtcccttctc ggcgattctg cggagggatc tccgtgggc ggtgaacgcc gatgattata        300
taaggacgcg ccgggtgtgg cacagctagt tccgtcgcag ccgggatttg ggtcgcggtt        360
cttgtttgtg gatcgctgtg atcgtcactt ggtgagttgc gggctgctgg gctggccggg        420
gctttcgtgg ccgccgggcc gctcggtggg acggaagcgt gtggagagac cgccaagggc        480
tgtagtctgg gtccgcgagc aaggttgccc tgaactgggg gttgggggga gcgcacaaaa       540
tggcggctgt tcccgagtct tgaatggaag acgcttgtaa ggcgggctgt gaggtcgttg        600
aaacaaggtg gggggcatgg tgggcggcaa gaacccaagg tcttgaggcc ttcgctaatg        660
cgggaaagct cttattcggg tgagatgggc tggggcacca tctggggacc ctgacgtgaa        720
gtttgtcact gactggagaa ctcgggtttg tcgtctggtt gcgggggcgg cagttatgcg        780
gtgccgttgg gcagtgcacc cgtacctttg ggagcgcgcg cctcgtcgtg tcgtgacgtc        840
```

```
acccgttctg ttggcttata atgcagggtg gggccacctg ccggtaggtg tgcggtaggc    900
ttttctccgt cgcaggacgc agggttcggg cctagggtag gctctcctga atcgacaggc    960
gccggacctc tggtgagggg agggataagt gaggcgtcag tttctttggt cggttttatg   1020
tacctatctt cttaagtagc tgaagctccg gttttgaact atgcgctcgg ggttggcgag   1080
tgtgttttgt gaagtttttt aggcaccttt tgaaatgtaa tcatttgggt caatatgtaa   1140
ttttcagtgt tagactagta aa                                            1162

<210> SEQ ID NO 44
<211> LENGTH: 120
<212> TYPE: DNA
<213> ORGANISM: Artificial Sequence
<220> FEATURE:
<223> OTHER INFORMATION: Poly A- SV40

<400> SEQUENCE: 44
gtttattgca gcttataatg gttacaaata aagcaatagc atcacaaatt tcacaaataa     60
agcatttttt tcactgcatt ctagttgtgg tttgtccaaa ctcatcaatg tatcttatca    120

<210> SEQ ID NO 45
<211> LENGTH: 227
<212> TYPE: DNA
<213> ORGANISM: Artificial Sequence
<220> FEATURE:
<223> OTHER INFORMATION: Poly A- bGH

<400> SEQUENCE: 45
gactgtgcct tctagttgcc agccatctgt tgtttgcccc tcccccgtgc cttccttgac     60
cctggaaggt gccactccca ctgtcctttc ctaataaaat gaggaaattg catcgcattg    120
tctgagtagg tgtcattcta ttctgggggg tggggtgggg caggacagca agggggagga   180
ttgggaagac aatagcaggc atgctgggga tgcggtgggc tctatgg                 227

<210> SEQ ID NO 46
<211> LENGTH: 1695
<212> TYPE: DNA
<213> ORGANISM: Artificial Sequence
<220> FEATURE:
<223> OTHER INFORMATION: Envelope- RD114

<400> SEQUENCE: 46
atgaaactcc caacaggaat ggtcatttta tgtagcctaa taatagttcg ggcagggttt     60
gacgaccccc gcaaggctat cgcattagta caaaacaac atggtaaacc atgcgaatgc    120
agcggagggc aggtatccga ggccccaccg aactccatcc aacaggtaac ttgcccaggc    180
aagacggcct acttaatgac caaccaaaaa tggaaatgca gagtcactcc aaaaaatctc    240 accccctagcg ggggagaact ccagaactgc ccctgtaaca cttttccagga ctcgatgcac    300 agttcttgtt atactgaata ccggcaatgc agggcgaata taagacata ctacacggcc    360 accttgctta aaatacggtc tgggagcctc aacgaggtac agatattaca aaaccccaat    420
cagctcctac agtcccccttg taggggctct ataaatcagc ccgtttgctg gagtgccaca    480
gcccccatcc atatctccga tggtggagga cccctcgata ctaagagagt gtggacagtc    540
caaaaaaggc tagaacaaat tcataaggct atgcatcctg aacttcaata ccaccccctta    600 gccctgccca agtcagaga tgaccttagc cttgatgcac ggactttga tatcctgaat    660 accacttttta ggttactcca gatgtccaat tttagccttg cccaagattg ttggctctgt    720
```

| | |
|---|---|
| ttaaaactag gtaccoctac ccctcttgcg atacccactc cctctttaac ctactcccta | 780 |
| gcagactccc tagcgaatgc ctcctgtcag attatacctc ccctcttggt tcaaccgatg | 840 |
| cagttctcca actcgtcctg tttatcttcc cctttcatta acgatacgga acaaatagac | 900 |
| ttaggtgcag tcacctttac taactgcacc tctgtagcca atgtcagtag tcctttatgt | 960 |
| gccctaaacg ggtcagtctt cctctgtgga aataacatgg catacaccta tttaccccaa | 1020 |
| aactggacag gactttgcgt ccaagcctcc ctcctccccg acattgacat catcccgggg | 1080 |
| gatgagccag tccccattcc tgccattgat cattatatac atagacctaa acgagctgta | 1140 |
| cagttcatcc ctttactagc tggactggga atcaccgcag cattcaccac cggagctaca | 1200 |
| ggcctaggtg tctccgtcac ccagtataca aaattatccc atcagttaat atctgatgtc | 1260 |
| caagtcttat ccggtaccat acaagattta caagaccagg tagactcgtt agctgaagta | 1320 |
| gttctccaaa ataggagggg actggaccta ctaacggcag aacaaggagg aatttgttta | 1380 |
| gccttacaag aaaaatgctg tttttatgct aacagtcag gaattgtgag aaacaaaata | 1440 |
| agaaccctac aagaagaatt acaaaaacgc agggaaagcc tggcatccaa ccctctctgg | 1500 |
| accgggctgc agggctttct tccgtacctc ctacctctcc tgggacccct actcaccctc | 1560 |
| ctactcatac taaccattgg gccatgcgtt ttcaatcgat tggtccaatt tgttaaagac | 1620 |
| aggatctcag tggtccaggc tctggttttg actcagcaat atcaccagct aaaacccata | 1680 |
| gagtacgagc catga | 1695 |

<210> SEQ ID NO 47
<211> LENGTH: 2013
<212> TYPE: DNA
<213> ORGANISM: Artificial Sequence
<220> FEATURE:
<223> OTHER INFORMATION: Envelope- GALV

<400> SEQUENCE: 47

| | |
|---|---|
| atgcttctca cctcaagccc gcaccaccatt cggcaccaga tgagtcctgg gagctggaaa | 60 |
| agactgatca tcctcttaag ctgcgtattc ggagacggca aaacgagtct gcagaataag | 120 |
| aaccccacc agcctgtgac cctcacctgg caggtactgt cccaaactgg ggacgttgtc | 180 |
| tgggacaaaa aggcagtcca gccccttgg acttggtggc cctctcttac acctgatgta | 240 |
| tgtgccctgg cggccggtct tgagtcctgg gatatcccgg gatccgatgt atcgtcctct | 300 |
| aaaagagtta gacctcctga ttcagactat actgccgctt ataagcaaat cacctgggga | 360 |
| gccatagggt gcagctaccc tcgggctagg accaggatgg caaattcccc cttctacgtg | 420 |
| tgtccccgag ctggccgaac ccattcagaa gctaggaggt gtgggggct agaatcccta | 480 |
| tactgtaaag aatggagttg tgagaccacg ggtaccgttt attggcaacc caagtcctca | 540 |
| tgggacctca taactgtaaa atgggaccaa aatgtgaaat gggagcaaaa atttcaaaag | 600 |
| tgtgaacaaa ccggctggtg taaccccctc aagatagact tcacagaaaa aggaaaactc | 660 |
| tccagagatt ggataacgga aaaaacctgg gaattaaggt tctatgtata tggacacccc | 720 |
| ggcatacagt tgactatccg cttagaggtc actaacatgc cggttgtggc agtgggccca | 780 |
| gaccctgtcc ttgcggaaca gggacctcct agcaagcccc tcactctccc tctctcccca | 840 |
| cggaaagcgc cgcccacccc tctacccccg gcggctagtg agcaaacccc tgcggtgcat | 900 |
| ggagaaactg ttaccctaaa ctctccgcct cccaccagtg gcgaccgact ctttggcctt | 960 |
| gtgcagggg ccttcctaac cttgaatgct accaacccag gggccactaa gtcttgctgg | 1020 |
| ctctgtttgg gcatgagccc cccttattat gaagggatag cctcttcagg agaggtcgct | 1080 |

| | | |
|---|---|---|
| tataccteca accataccog atgccactgg ggggcccaag gaaagcttac cctcactgag | 1140 |
| gtctccggac tcgggtcatg catagggaag gtgcctctta cccatcaaca tctttgcaac | 1200 |
| cagaccttac ccatcaattc ctctaaaaac catcagtatc tgctcccctc aaaccatagc | 1260 |
| tggtgggcct gcagcactgg cctcacccce tgcctctcca cctcagtttt taatcagtct | 1320 |
| aaagacttct gtgtccaggt ccagctgatc ccccgcatct attaccattc tgaagaaacc | 1380 |
| ttgttacaag cctatgacaa atcaccccce aggtttaaaa gagagcctgc ctcacttacc | 1440 |
| ctagctgtct tcctggggtt agggattgcg gcaggtatag gtactggctc aaccgcccta | 1500 |
| attaaagggc ccatagacct ccagcaaggc ctaaccagcc tccaaatcgc cattgacgct | 1560 |
| gacctccggg cccttcagga ctcaatcagc aagctagagg actcactgac ttccctatct | 1620 |
| gaggtagtac tccaaaatag gagaggcctt gacttactat tccttaaaga aggaggcctc | 1680 |
| tgcgcggccc taaaagaaga gtgctgtttt tatgtagacc actcaggtgc agtacgagac | 1740 |
| tccatgaaaa aacttaaaga aagactagat aaaagacagt tagagcgcca gaaaaaccaa | 1800 |
| aactggtatg aagggtggtt caataactcc ccttggttta ctaccctact atcaaccatc | 1860 |
| gctgggcccc tattgctcct ccttttgtta ctcactcttg ggccctgcat catcaataaa | 1920 |
| ttaatccaat tcatcaatga taggataagt gcagtcaaaa ttttagtcct tagacagaaa | 1980 |
| tatcagaccc tagataacga ggaaaacctt taa | 2013 |

```
<210> SEQ ID NO 48
<211> LENGTH: 1530
<212> TYPE: DNA
<213> ORGANISM: Artificial Sequence
<220> FEATURE:
<223> OTHER INFORMATION: Envelope- FUG

<400> SEQUENCE: 48
```

| | | |
|---|---|---|
| atggttccgc aggttctttt gtttgtactc cttctgggtt tttcgttgtg tttcgggaag | 60 |
| ttccccattt acacgatacc agacgaactt ggtccctgga gcctattga catacaccat | 120 |
| ctcagctgtc caaataacct ggttgtggag gatgaaggat gtaccaacct gtccgagttc | 180 |
| tcctacatgg aactcaaagt gggatacatc tcagccatca aagtgaacgg ttcacttgc | 240 |
| acaggtgttg tgacagaggc agagacctac accaactttg ttggttatgt cacaaccaca | 300 |
| ttcaagagaa agcatttccg ccccacccca gacgcatgta gagccgcgta taactggaag | 360 |
| atggccggtg accccagata tgaagagtcc ctacacaatc catccccga ctaccactgg | 420 |
| cttcgaactg taagaaccac caaagagtcc ctcattatca tatccccaag tgtgacagat | 480 |
| ttggacccat atgacaaatc ccttcactca agggtcttcc ctggcggaaa gtgctcagga | 540 |
| ataacggtgt cctctaccta ctgctcaact aaccatgatt acaccatttg gatgcccgag | 600 |
| aatccgagac caaggacacc ttgtgacatt tttaccaata gcagagggaa gagagcatcc | 660 |
| aacgggaaca agacttgcgg cttttgtgga tgaaagaggcc tgtataagtc tctaaaagga | 720 |
| gcatgcaggc tcaagttatg tggagttctt ggacttagac ttatggatgg aacatgggtc | 780 |
| gcgatgcaaa catcagatga gaccaaatgg tgccctccag atcagttggt gaatttgcac | 840 |
| gactttcgct cagacgagat cgagcatctc gttgtggagg agttagttaa gaaaagagag | 900 |
| gaatgtctgg atgcattaga gtccatcatg accaccaagt cagtaagttt cagacgtctc | 960 |
| agtcacctga aaaacttgt cccagggttt ggaaaagcat ataccatatt caacaaaacc | 1020 |
| ttgatggagg ctgatgctca ctacaagtca gtccggacct ggaatgagat catcccctca | 1080 |

```
aaagggtgtt tgaaagttgg aggaaggtgc catcctcatg tgaacggggt gtttttcaat   1140
ggtataatat tagggcctga cgaccatgtc ctaatcccag agatgcaatc atccctcctc   1200
cagcaacata tggagttgtt ggaatcttca gttatccccc tgatgcaccc cctggcagac   1260
ccttctacag ttttcaaaga aggtgatgag gctgaggatt ttgttgaagt tcacctcccc   1320
gatgtgtaca aacagatctc aggggttgac ctgggtctcc cgaactgggg aaagtatgta   1380
ttgatgactg caggggccat gattggcctg gtgttgatat tttccctaat gacatggtgc   1440
agagttggta tccatctttg cattaaatta aagcacacca agaaaagaca gatttataca   1500
gacatagaga tgaaccgact tggaaagtaa                                    1530
```

<210> SEQ ID NO 49
<211> LENGTH: 1497
<212> TYPE: DNA
<213> ORGANISM: Artificial Sequence
<220> FEATURE:
<223> OTHER INFORMATION: Envelope- LCMV

<400> SEQUENCE: 49

```
atgggtcaga ttgtgacaat gtttgaggct ctgcctcaca tcatcgatga ggtgatcaac     60
attgtcatta ttgtgcttat cgtgatcacg ggtatcaagg ctgtctacaa ttttgccacc    120
tgtgggatat tcgcattgat cagtttccta cttctggctg gcaggtcctg tggcatgtac    180
ggtcttaagg gacccgacat ttacaaagga gtttaccaat ttaagtcagt ggagtttgat    240
atgtcacatc tgaacctgac catgcccaac gcatgttcag ccaacaactc ccaccattac    300
atcagtatgg ggacttctgg actagaattg accttcacca atgattccat catcagtcac    360
aacttttgca atctgacctc tgccttcaac aaaaagacct ttgaccacac actcatgagt    420
atagtttcga gcctacacct cagtatcaga gggaactcca actataaggc agtatcctgc    480
gacttcaaca atggcataac catccaatac aacttgacat tctcagatcg acaaagtgct    540
cagagccagt gtagaacctt cagaggtaga gtcctagata tgtttagaac tgccttcggg    600
gggaaataca tgaggagtgg ctggggctgg acaggctcag atggcaagac cacctggtgt    660
agccagacga gttaccaata cctgattata caaaatagaa cctgggaaaa ccactgcaca    720
tatgcaggtc cttttgggat gtccaggatt ctcctttccc aagagaagac taagttcttc    780
actaggagac tagcgggcac attcacctgg actttgtcag actcttcagg ggtggagaat    840
ccaggtggtt attgcctgac caaatggatg attcttgctg cagagcttaa gtgtttcggg    900
aacacagcag ttgcgaaatg caatgtaaat catgatgccg aattctgtga catgctgcga    960
ctaattgact acaacaaggc tgctttgagt aagttcaaag aggacgtaga atctgccttg   1020
cacttattca aaacaacagt gaattctttg atttcagatc aactactgat gaggaaccac   1080
ttgagagatc tgatgggggt gccatattgc aattactcaa agttttggta cctagaacat   1140
gcaaagaccg gcgaaactag tgtccccaag tgctggcttg tcaccaatgg ttcttactta   1200
aatgagaccc acttcagtga tcaaatcgaa caggaagccg ataacatgat tacagagatg   1260
ttgaggaagg attacataaa gaggcagggg agtacccccc tagcattgat ggaccttctg   1320
atgttttcca catctgcata tctagtcagc atcttcctgc accttgtcaa aataccaaca   1380
cacaggcaca taaaaggtgg ctcatgtcca aagccacacc gattaaccaa caaaggaatt   1440
tgtagttgtg gtgcatttaa ggtgcctggt gtaaaaaccg tctggaaaag acgctga      1497
```

<210> SEQ ID NO 50
<211> LENGTH: 1692

<212> TYPE: DNA
<213> ORGANISM: Artificial Sequence
<220> FEATURE:
<223> OTHER INFORMATION: Envelope- FPV

<400> SEQUENCE: 50

```
atgaacactc aaatcctggt tttcgccctt gtggcagtca tccccacaaa tgcagacaaa 60
atttgtcttg gacatcatgc tgtatcaaat ggcaccaaag taaacacact cactgagaga 120
ggagtagaag ttgtcaatgc aacggaaaca gtggagcgga caaacatccc caaaatttgc 180
tcaaaaggga aaagaaccac tgatcttggc caatgcggac tgttagggac cattaccgga 240
ccacctcaat gcgaccaatt tctagaattt tcagctgatc taataatcga gagacgagaa 300
ggaaatgatg tttgttaccc ggggaagttt gttaatgaag aggcattgcg acaaatcctc 360
agaggatcag gtgggattga caaagaaaca atgggattca catatagtgg aataaggacc 420
aacggaacaa ctagtgcatg tagaagatca gggtcttcat tctatgcaga aatggagtgg 480
ctcctgtcaa atacagacaa tgctgctttc ccacaaatga caaaatcata caaaaacaca 540
aggagagaat cagctctgat agtctgggga atccaccatt caggatcaac caccgaacag 600
accaaactat atgggagtgg aaataaactg ataacagtcg ggagttccaa atatcatcaa 660
tcttttgtgc cgagtccagg aacacgaccg cagataaatg gccagtccgg acggattgat 720
tttcattggt tgatcttgga tcccaatgat acagttactt ttagtttcaa tggggctttc 780
atagctccaa atcgtgccag cttcttgagg ggaaagtcca tggggatcca gagcgatgtg 840
caggttgatg ccaattgcga aggggaatgc taccacagtg gagggactat aacaagcaga 900
ttgccttttc aaaacatcaa tagcagagca gttggcaaat gcccaagata tgtaaaacag 960
gaaagtttat tattggcaac tgggatgaag aacgttcccg aaccttccaa aaaaaggaaa 1020
aaaagaggcc tgtttggcgc tatagcaggg tttattgaaa atggttggga aggtctggtc 1080
gacgggtggt acggtttcag gcatcagaat gcacaaggag aaggaactgc agcagactac 1140
aaaagcaccc aatcggcaat tgatcagata accggaaagt taaatagact cattgagaaa 1200
accaaccagc aatttgagct aatagataat gaattcactg aggtggaaaa gcagattggc 1260
aatttaatta actggaccaa agactccatc acagaagtat ggtcttacaa tgctgaactt 1320
cttgtggcaa tggaaaacca gcacactatt gatttggctg attcagagat gaacaagctg 1380
tatgagcgag tgaggaaaca attaagggaa aatgctgaag aggatggcac tggttgcttt 1440
gaaatttttc ataaatgtga cgatgattgt atggctagta taaggaacaa tacttatgat 1500
cacagcaaat acagagaaga agcgatgcaa aatagaatac aaattgaccc agtcaaattg 1560
agtagtggct acaaagatgt gatactttgg tttagcttcg ggcatcatg cttttgctt 1620
cttgccattg caatgggcct tgttttcata tgtgtgaaga acggaaacat gcggtgcact 1680
atttgtatat aa 1692

<210> SEQ ID NO 51
<211> LENGTH: 1266
<212> TYPE: DNA
<213> ORGANISM: Artificial Sequence
<220> FEATURE:
<223> OTHER INFORMATION: Envelope- RRV
<400> SEQUENCE: 51
agtgtaacag agcactttaa tgtgtataag gctactagac catacctagc acattgcgcc 60
gattgcgggg acgggtactt ctgctatagc ccagttgcta tcgaggagat ccgagatgag 120
```

```
gcgtctgatg gcatgcttaa gatccaagtc tccgcccaaa taggtctgga caaggcaggc      180
acccacgccc acacgaagct ccgatatatg gctggtcatg atgttcagga atctaagaga      240
gattccttga gggtgtacac gtccgcagcg tgctccatac atgggacgat gggacacttc      300
atcgtcgcac actgtccacc aggcgactac ctcaaggttt cgttcgagga cgcagattcg      360
cacgtgaagg catgtaaggt ccaatacaag cacaatccat tgccggtggg tagagagaag      420
ttcgtggtta gaccacactt tggcgtagag ctgccatgca cctcatacca gctgacaacg      480
gctcccaccg acgaggagat tgacatgcat acaccgccag atataccgga tcgcaccctg      540
ctatcacaga cggcgggcaa cgtcaaaata acagcaggcg gcaggactat caggtacaac      600
tgtacctgcg gccgtgacaa cgtaggcact accagtactg acaagaccat caacacatgc      660
aagattgacc aatgccatgc tgccgtcacc agccatgaca atggcaatt  tacctctcca      720 tttgttccca gggctgatca gacagctagg aaaggcaagg tacacgttcc gttccctctg      780
actaacgtca cctgccgagt gccgttggct cgagcgccgg atgccaccta tggtaagaag      840
gaggtgaccc tgagattaca cccagatcat ccgacgctct tctcctatag gagtttagga      900
gccgaaccgc acccgtacga ggaatgggtt gacaagttct ctgagcgcat catcccagtg      960
acggaagaag ggattgagta ccagtggggc aacaacccgc cggtctgcct gtgggcgcaa     1020
ctgacgaccg agggcaaacc ccatggctgg ccacatgaaa tcattcagta ctattatgga     1080 ctatacccg ccgccactat tgccgcagta tccggggcga gtctgatggc cctcctaact     1140
ctggcggcca catgctgcat gctggccacc gcgaggagaa agtgcctaac accgtacgcc     1200
ctgacgccag agcggtggt accgttgaca ctggggctgc tttgctgcgc accgagggcg     1260
aatgca                                                               1266

<210> SEQ ID NO 52
<211> LENGTH: 1266
<212> TYPE: DNA
<213> ORGANISM: Artificial Sequence
<220> FEATURE:
<223> OTHER INFORMATION: Envelope- MLV 10A1

<400> SEQUENCE: 52
agtgtaacag agcactttaa tgtgtataag gctactagac catacctagc acattgcgcc       60
gattgcgggg acgggtactt ctgctatagc ccagttgcta tcgaggagat ccagatgag      120 gcgtctgatg gcatgcttaa gatccaagtc tccgcccaaa taggtctgga caaggcaggc      180
acccacgccc acacgaagct ccgatatatg gctggtcatg atgttcagga atctaagaga      240
gattccttga gggtgtacac gtccgcagcg tgctccatac atgggacgat gggacacttc      300
atcgtcgcac actgtccacc aggcgactac ctcaaggttt cgttcgagga cgcagattcg      360
cacgtgaagg catgtaaggt ccaatacaag cacaatccat tgccggtggg tagagagaag      420
ttcgtggtta gaccacactt tggcgtagag ctgccatgca cctcatacca gctgacaacg      480
gctcccaccg acgaggagat tgacatgcat acaccgccag atataccgga tcgcaccctg      540
ctatcacaga cggcgggcaa cgtcaaaata acagcaggcg gcaggactat caggtacaac      600
tgtacctgcg gccgtgacaa cgtaggcact accagtactg acaagaccat caacacatgc      660
aagattgacc aatgccatgc tgccgtcacc agccatgaca atggcaatt  tacctctcca      720 tttgttccca gggctgatca gacagctagg aaaggcaagg tacacgttcc gttccctctg      780
actaacgtca cctgccgagt gccgttggct cgagcgccgg atgccaccta tggtaagaag      840
gaggtgaccc tgagattaca cccagatcat ccgacgctct tctcctatag gagtttagga      900
```

```
gccgaaccgc acccgtacga ggaatgggtt gacaagttct ctgagcgcat catcccagtg    960
acggaagaag ggattgagta ccagtggggc aacaacccgc cggtctgcct gtgggcgcaa   1020
ctgacgaccg agggcaaacc ccatggctgg ccacatgaaa tcattcagta ctattatgga   1080
ctataccccg ccgccactat tgccgcagta tccggggcga gtctgatggc cctcctaact   1140
ctggcggcca catgctgcat gctggccacc gcgaggagaa agtgcctaac accgtacgcc   1200
ctgacgccag gagcggtggt accgttgaca ctggggctgc tttgctgcgc accgagggcg   1260
aatgca                                                              1266
```

<210> SEQ ID NO 53
<211> LENGTH: 2030
<212> TYPE: DNA
<213> ORGANISM: Artificial Sequence
<220> FEATURE:
<223> OTHER INFORMATION: Envelope- Ebola

<400> SEQUENCE: 53

```
atgggtgtta caggaatatt gcagttacct cgtgatcgat tcaagaggac atcattcttt     60
ctttgggtaa ttatcctttt ccaaagaaca ttttccatcc cacttggagt catccacaat    120
agcacattac aggttagtga tgtcgacaaa ctggtttgcc gtgacaaact gtcatccaca    180
aatcaattga gatcagttgg actgaatctc gaagggaatg gagtggcaac tgacgtgcca    240
tctgcaacta aagatggggg cttcaggtcc ggtgtcccac caaggtggt caattatgaa    300
gctggtgaat gggctgaaaa ctgctacaat cttgaaatca aaaaacctga cgggagtgag    360
tgtctaccag cagcgccaga cgggattcgg ggcttccccc ggtgccggta tgtgcacaaa    420
gtatcaggaa cgggaccgtg tgccggagac tttgccttcc acaaagaggg tgctttcttc    480
ctgtatgacc gacttgcttc cacagttatc taccgaggaa cgactttcgc tgaaggtgtc    540
gttgcatttc tgatactgcc ccaagctaag aaggacttct tcagctcaca ccccttgaga    600
gagccggtca tgcaacggga ggacccgtct agtggctact attctaccac aattagatat    660
caagctaccg ttttggaac caatgagaca gagtatttgt tcgaggttga caatttgacc    720
tacgtccaac ttgaatcaag attcacacca cagtttctgc tccagctgaa tgagacaata    780
tatacaagtg ggaaaaggag caataccacg ggaaaactaa tttggaaggt caaccccgaa    840
attgatacaa caatcgggga gtgggccttc tgggaaacta aaaaaacctc actagaaaaa    900
ttcgcagtga agagttgtct ttcacagctg tatcaaacag agccaaaaac atcagtggtc    960
agagtccggc gcgaacttct ccgacccag ggaccaacac aacaactgaa gaccacaaaa   1020
tcatggcttc agaaaattcc tctgcaatgg ttcaagtgca cagtcaagga agggaagctg   1080
cagtgtcgca tctgacaacc cttgccacaa tctccgcgag tcctcaaccc ccacaaacca   1140
aaccaggtcc ggacaacagc acccacaata caccgtgta taacttgac atctctgagg   1200
caactcaagt tgaacaacat caccgcagaa cagacaacga cagcacagcc tccgacactc   1260
ccccgccac gaccgcagcc ggaccctaa agcagaaaac accaacacg agcaagggta   1320
ccgacctcct ggaccccgcc accacaacaa gtccccaaaa ccacagcgag accgctggca   1380
acaacaacac tcatcaccaa gataccggag aagagagtgc cagcagcggg aagctaggct   1440
taattaccaa tactattgct ggagtcgcag gactgatcac aggcgggagg agagctcgaa   1500
gagaagcaat tgtcaatgct caacccaaat gcaaccctaa tttacattac tggactactc   1560
aggatgaagg tgctgcaatc ggactggcct ggataccata tttcgggcca gcagccgagg   1620
```

-continued

| | |
|---|---|
| gaatttacat agaggggctg atgcacaatc aagatggttt aatctgtggg ttgagacagc | 1680 |
| tggccaacga gacgactcaa gctcttcaac tgttcctgag agccacaacc gagctacgca | 1740 |
| ccttttcaat cctcaaccgt aaggcaattg atttcttgct gcagcgatgg ggcggcacat | 1800 |
| gccacatttt gggaccggac tgctgtatcg aaccacatga ttggaccaag aacataacag | 1860 |
| acaaaattga tcagattatt catgatttig ttgataaaac ccttccggac caggggggaca | 1920 |
| atgacaattg gtggacagga tggagacaat ggataccggc aggtattgga gttacaggcg | 1980 |
| ttataattgc agttatcgct ttattctgta tatgcaaatt tgtcttttag | 2030 |

<210> SEQ ID NO 54
<211> LENGTH: 237
<212> TYPE: DNA
<213> ORGANISM: Artificial Sequence
<220> FEATURE:
<223> OTHER INFORMATION: Polymerase III shRNA promoters- U6 promoter

<400> SEQUENCE: 54

| | |
|---|---|
| tttcccatga ttccttcata tttgcatata cgatacaagg ctgttagaga gataattgga | 60 |
| attaatttga ctgtaaacac aaagatatta gtacaaaata cgtgacgtag aaagtaataa | 120 |
| tttcttgggt agtttgcagt tttaaaatta tgttttaaaa tggactatca tatgcttacc | 180 |
| gtaacttgaa agtatttcga tttcttggct ttatatatct tgtggaaagg acgaaac | 237 |

<210> SEQ ID NO 55
<211> LENGTH: 243
<212> TYPE: DNA
<213> ORGANISM: Artificial Sequence
<220> FEATURE:
<223> OTHER INFORMATION: Polymerase III shRNA promoters- 7SK promoter

<400> SEQUENCE: 55

| | |
|---|---|
| ctgcagtatt tagcatgccc cacccatctg caaggcattc tggatagtgt caaaacagcc | 60 |
| ggaaatcaag tccgtttatc tcaaacttta gcattttggg aataaatgat atttgctatg | 120 |
| ctggttaaat tagattttag ttaaattttcc tgctgaagct ctagtacgat aagcaacttg | 180 |
| acctaagtgt aaagttgaga tttccttcag gtttatatag cttgtgcgcc gcctggctac | 240 |
| ctc | 243 |

<210> SEQ ID NO 56
<211> LENGTH: 21
<212> TYPE: DNA
<213> ORGANISM: Artificial Sequence
<220> FEATURE:
<223> OTHER INFORMATION: FDPS target sequence #1

<400> SEQUENCE: 56

| | |
|---|---|
| gtcctggagt acaatgccat t | 21 |

<210> SEQ ID NO 57
<211> LENGTH: 21
<212> TYPE: DNA
<213> ORGANISM: Artificial Sequence
<220> FEATURE:
<223> OTHER INFORMATION: FDPS target sequence #2

<400> SEQUENCE: 57

| | |
|---|---|
| gcaggatttc gttcagcact t | 21 |

<210> SEQ ID NO 58
<211> LENGTH: 21

```
<212> TYPE: DNA
<213> ORGANISM: Artificial Sequence
<220> FEATURE:
<223> OTHER INFORMATION: FDPS target sequence #3

<400> SEQUENCE: 58
gccatgtaca tggcaggaat t                                              21

<210> SEQ ID NO 59
<211> LENGTH: 21
<212> TYPE: DNA
<213> ORGANISM: Artificial Sequence
<220> FEATURE:
<223> OTHER INFORMATION: FDPS target sequence #4

<400> SEQUENCE: 59
gcagaaggag gctgagaaag t                                              21

<210> SEQ ID NO 60
<211> LENGTH: 49
<212> TYPE: DNA
<213> ORGANISM: Artificial Sequence
<220> FEATURE:
<223> OTHER INFORMATION: Non-targeting sequence

<400> SEQUENCE: 60
gccgctttgt aggatagagc tcgagctcta tcctacaaag cggctttt                 49

<210> SEQ ID NO 61
<211> LENGTH: 20
<212> TYPE: DNA
<213> ORGANISM: Artificial Sequence
<220> FEATURE:
<223> OTHER INFORMATION: Forward primer

<400> SEQUENCE: 61
aggaattgat ggcgagaagg                                                20

<210> SEQ ID NO 62
<211> LENGTH: 22
<212> TYPE: DNA
<213> ORGANISM: Artificial Sequence
<220> FEATURE:
<223> OTHER INFORMATION: Reverse primer

<400> SEQUENCE: 62
cccaaagagg tcaaggtaat ca                                             22

<210> SEQ ID NO 63
<211> LENGTH: 18
<212> TYPE: DNA
<213> ORGANISM: Artificial Sequence
<220> FEATURE:
<223> OTHER INFORMATION: Forward primer

<400> SEQUENCE: 63
agcgcggcta cagcttca                                                  18

<210> SEQ ID NO 64
<211> LENGTH: 20
<212> TYPE: DNA
<213> ORGANISM: Artificial Sequence
<220> FEATURE:
<223> OTHER INFORMATION: Reverse primer

<400> SEQUENCE: 64
```

```
ggcgacgtag cacagcttct                                                 20

<210> SEQ ID NO 65
<211> LENGTH: 130
<212> TYPE: DNA
<213> ORGANISM: Artificial Sequence
<220> FEATURE:
<223> OTHER INFORMATION: Left Inverted Terminal Repeat (Left ITR)

<400> SEQUENCE: 65
cctgcaggca gctgcgcgct cgctcgctca ctgaggccgc ccgggcgtcg ggcgaccttt     60
ggtcgcccgg cctcagtgag cgagcgagcg cgcagagagg gagtgggcaa ctccatcact   120
aggggttcct                                                           130

<210> SEQ ID NO 66
<211> LENGTH: 151
<212> TYPE: DNA
<213> ORGANISM: Artificial Sequence
<220> FEATURE:
<223> OTHER INFORMATION: Right Inverted Terminal Repeat (Right ITR)

<400> SEQUENCE: 66
gagcggccgc aggaacccct agtgatggag ttggccactc cctctctgcg cgctcgctcg     60
ctcactgagg ccgggcgacc aaaggtcgcc cgacgcccgg gctttgcccg ggcggcctca   120
gtgagcgagc gagcgcgcag ctgcctgcag g                                   151

<210> SEQ ID NO 67
<211> LENGTH: 1227
<212> TYPE: DNA
<213> ORGANISM: Artificial Sequence
<220> FEATURE:
<223> OTHER INFORMATION: Helper plasmid without REV

<400> SEQUENCE: 67
tctagaagga gctttgttcc ttgggttctt gggagcagca ggaagcacta tgggcgcagc     60
gtcaatgacg ctgacggtac aggccagaca attattgtct ggtatagtgc agcagcagaa   120
caatttgctg agggctattg aggcgcaaca gcatctgttg caactcacag tctgggcat    180 caagcagctc caggcaagaa tcctggctgt ggaaagatac ctaaaggatc aacagctcct   240 agatctttt ccctctgcca aaaattatgg ggacatcatg aagccccttg agcatctgac   300
ttctggctaa taaaggaaat ttattttcat tgcaatagtg tgttggaatt ttttgtgtct   360
ctcactcgga aggacatatg ggagggcaaa tcatttaaaa catcagaatg agtatttggt   420
ttagagtttg gcaacatatg ccatatgctg ctgccatga acaaggtgg ctataaagag    480 gtcatcagta tatgaaacag ccccctgctg tccattcctt attccataga aaagccttga   540
cttgaggtta gattttttt atattttgtt ttgtgttatt ttttctttta acatccctaa    600
aattttcctt acatgtttta ctagccagat ttttcctcct ctcctgacta ctcccagtca   660
tagctgtccc tcttctctta tgaagatccc tcgacctgca gcccaagctt ggcgtaatca   720
tggtcatagc tgtttcctgt gtgaaattgt tatccgctca caattccaca acatacga    780 gccgaagca taaagtgtaa agcctggggt gcctaatgag tgagctaact cacattaatt   840
gcgttgcgct cactgcccgc tttccagtcg ggaaacctgt cgtgccagcg gatccgcatc   900
tcaattagtc agcaaccata gtcccgcccc taactccgcc catcccgccc ctaactccgc   960
ccagttccgc ccattctccg ccccatggct gactaatttt ttttatttat gcagaggccg  1020
aggccgcctc ggcctctgag ctattccaga agtagtgagg aggcttttt ggaggcctag  1080
```

-continued

```
gcttttgcaa aaagctaact tgtttattgc agcttataat ggttacaaat aaagcaatag    1140
catcacaaat ttcacaaata aagcattttt ttcactgcat tctagttgtg gtttgtccaa    1200
actcatcaat gtatcttatc acccggg                                        1227
```

METHODS AND COMPOSITIONS FOR THE ACTIVATION OF GAMMA-DELTA T-CELLS

CROSS-REFERENCE TO RELATED APPLICATION

This application is a continuation of U.S. patent application Ser. No. 15/652,080, filed on Jul. 17, 2017 entitled "Methods and Compositions for the Activation of Gamma-Delta T-cells" which is a continuation of International Application No. PCT/US17/13399 filed on Jan. 13, 2017, entitled "Methods and Compositions for the Activation of Gamma-Delta T-cells" which claims priority to U.S. Provisional Patent Application No. 62/279,474, filed on Jan. 15, 2016, and entitled "Methods and Compositions for the Activation of Gamma-Delta T-cells," the disclosures of which are incorporated herein by reference.

FIELD OF THE INVENTION

The present disclosure relates generally to the fields of gene therapy and immunotherapy, specifically in relation to increased activation of gamma delta ("GD") T cells.

BACKGROUND

Human T cells are distinguished on the basis of T cell receptor structure. The major populations, including CD4+ and CD8+ subsets, express a receptor composed of alpha and beta chains. A smaller subset expresses T cell receptor made from gamma and delta chains. Gamma delta ("GD") T cells make up 3-10% circulating lymphocytes, and Vδ2+ subset makes up 75% of GD T cells in blood. Vδ2+ cells recognize non-peptide epitopes and do not require antigen presentation by major histocompatibility complexes ("MHC") or human leukocyte antigen ("HLA"). The majority of Vδ2+ T cells also express a Vγ9 chain and are stimulated by exposure to 5-carbon pyrophosphate compounds that are intermediates in mevalonate and non-mevalonate sterol/isoprenoid synthesis pathways. The response to isopentenyl pyrophosphate (5-carbon) is universal among healthy human beings.

Another subset of GD T cells, Vδ1+, make up a much smaller percentage of the T cells circulating in the blood, but Vδ+1 cells are commonly found in the epithelial mucosa and the skin.

In general, GD T cells have several functions, including killing tumor cells and pathogen-infected cells. Stimulation through their unique T cell receptor ("TCRs") composed of two glycoprotein chains, γ and δ, improves the capacity for cellular cytotoxicity, cytokine secretion and other effector functions. The TCRs of GD T cells have unique specificities and the cells themselves occur in high clonal frequencies, thus allowing rapid innate-like responses to tumors and pathogens.

Aminobisphosphonate drugs ("ABPs") and other inhibitors of farnesyl diphosphate synthase ("FDPS"), which are downstream from isopentenyl pyrophosphate ("IPP") in the mevalonate pathway (see, for e.g., FIG. 1), have been used to treat various diseases, including cancers, specifically those involving bone metastasis. ABPs include trade names such as Zometa® (Novartis) and Fosamax® (Merck).

ABPs have also been used to stimulate GD T cells. This may be because when FDPS is inhibited in myeloid cells, IPP begins to accumulate and geranylgeranyl pyrophosphate ("GGPP"), a downstream product of FDPS that suppresses activation of the inflammasome pathway, is reduced. The reduction in GGPP removes an inhibitor of the caspase-dependent inflammasome pathway and allows secretion of mature cytokines including interleukin-beta and interleukin-18, the latter being especially important for gamma delta T cell activation.

Thus, when FDPS is blocked, the increased IPP and decreased GGPP combine to activate Vδ2+ T cells. Vδ2+ cells activated by IPP or ABPs will proliferate rapidly, express a number of cytokines and chemokines, and can function to cytotoxically destroy tumor cells or cells infected with pathogenic microorganisms.

However, ABPs are associated with inflammation and osteonecrosis, as well as having poor bioavailability due to their chemistry. Likewise, IPP has a very short half-life and is difficult to synthesize. Both types of compounds require systemic administration in an individual. Accordingly, both ABPs in general, and IPP specifically, leave a great deal to be desired for therapeutic purposes.

SUMMARY OF THE INVENTION

In one aspect, a method of activating a GD T cell is provided. The method includes infecting, in the presence of the GD T cell, a target cell with a viral delivery system that encodes at least one genetic element. In embodiments, the at least one genetic element includes a small RNA capable of inhibiting production of an enzyme involved in the mevalonate pathway. In embodiments, the enzyme is FDPS. In embodiments, when the enzyme is inhibited in the target cell, the target cell subsequently activates the GD T cell. In embodiments, the target cell is a cancer cell or a cell that has been infected with an infectious agent. In a preferred embodiment, the activation of the GD T cell results in the GD T cell killing the cancer cell or the cell infected with an infectious agent. In embodiments, the at least one encoded genetic element includes a microRNA or a shRNA. In further embodiments, the target cell is also contacted with an aminobisphosphonate drug. In embodiments, the aminobisphosphonate drug is zoledronic acid.

In another aspect, a method of treating cancer in a subject is provided. The method includes administering to the subject a therapeutically-effective amount of a viral delivery system that encodes at least one genetic element. In embodiments, the at least one genetic element includes a small RNA capable of inhibiting production of an enzyme involved in the mevalonate pathway. In further embodiments, when the enzyme is inhibited in a cancer cell in the presence of a GD T cell, the cancer cell activates the GD T cell, to thereby treat the cancer. In embodiments, the enzyme is FDPS. In embodiments, the at least one encoded genetic element includes a microRNA or a shRNA. In further embodiments, the target cell is also contacted with an aminobisphosphonate drug. In embodiments, the aminobisphosphonate drug is zoledronic acid.

In another aspect, a method of treating an infectious disease in a subject is provided. The method includes administering to the subject a therapeutically-effective amount of a viral delivery system that encodes at least one genetic element. In embodiments, the at least one genetic element includes a small RNA capable of inhibiting production of an enzyme involved in the mevalonate pathway. In further embodiments, when the enzyme is inhibited in a cell that is infected with an infectious agent in the presence of a GD T cell, the infected cell activates the GD T cell, to thereby treat the infected cell, and the infectious disease. In embodiments, the enzyme is FDPS. In embodiments, the at least one encoded genetic element includes a microRNA or a shRNA. In further embodiments, the target cell is also contacted with an aminobisphosphonate drug. In embodiments, the aminobisphosphonate drug is zoledronic acid.

In another aspect, the at least one encoded genetic element includes a shRNA having at least 80%, or at least 85%, or at least 90%, or at least 95% percent identity with GTCCTGGAGTACAATGCCATTCTCGAGAATGGCATTGTACTCCAGGACTTTTT (SEQ ID NO: 1); GCAGGATTTCGTTCAGCACTTCTCGAGAAGTGCTGAACGAA ATCCTGCTTTTT (SEQ ID NO: 2); GCCATGTACATGGCAGGAATTCTCGAGAA TTCCTGCCATGTACATGGCTTTTT (SEQ ID NO: 3); or GCAGAAGGAGGCTGA GAAAGTCTCGAGACTTTCTCAGCCTCCTTCTGCTTTTT (SEQ ID NO: 4). In a preferred embodiment, the shRNA includes GTCCTGGAGTACAATGCCATTCTCGAG AATGGCATTGTACTCCAGGACTTTTT (SEQ ID NO: 1); GCAGGATTTCGTTCAGCACTTCTCGAGAAGTGCTGAACGAAATCCTGCTTTTT (SEQ ID NO: 2); GCCA TGTACATGGCAGGAATTCTCGAGAATTCCTGCCATGTACATGGCTTTTT (SEQ ID NO: 3); or GCAGAAGGAGGCTGAGAAAGTCTCGAGACTTTCTCAGCCTCCTT CTGCTTTTT (SEQ ID NO: 4).

In another aspect, the at least one encoded genetic element includes a microRNA having at least 80%, or at least 85%, or at least 90%, or at least 95% percent identity with AAGGTATATTGCTGTTGACAGTGAGCGACACTTTCTCAGCCTCCTTCTGCGTGAA GCCACAGATGGCAGAAGGAGGCTGAGAAAGTGCTGCCTACTGCCTCGGACTTCA AGGGGCT (SEQ ID NO: 5); AAGGTATATTGCTGTTGACAGTGAGCGACACT TTCTCAGCCTCCTTCTGCGTGAAGCCACAGATGGCAGAAGGGCTGAGAAAGTGCT GCCTACTGCCTCGGACTTCAAGGGGCT (SEQ ID NO: 6); TGCTGTTGACAGTGAGCGACTTTCTCAGCCTCCTTCTGCGTGAAGCCACAGATGGCAGAAGGAGGCTG AGAAAGTTGCCTACTGCCTCGGA (SEQ ID NO: 7); CCTGGAGGCTTGCTGAAG GCTGTATGCTGACTTTCTCAGCCTCCTTCTGCTTTTGGCCACTGACTGAGCAGAAG GGCTGAGAAAGTCAGGACACAAGGCCTGTTACTAGCACTCA (SEQ ID NO: 8); CATCTCCATGGCTGTACCACCTTGTCGGGACTTTCTCAGCCTCCTTCTGCCTGTTG AATCTCATGGCAGAAGGAGGCGAGAAAAGTCTGACATTTTGGTATCTTTCATCTGA CCA (SEQ ID NO: 9); or GGGCCTGGCTCGAGCAGGGGGCGAGGGATACTTTCTCAGCCTCCTTCTGCTGGTCCCCTCCCCGCAGAAGGAGGCTGAGAAA GTCCTTCCCTCCCAATGACCGCGTCTTCGTCG (SEQ ID NO: 10).

In another aspect, a viral vector comprising at least one encoded genetic element is provided. The at least one encoded genetic element includes a small RNA capable of inhibiting production of an enzyme involved in the mevalonate pathway. In embodiments, the enzyme involved in the mevalonate pathway is farnesyl diphosphate synthase (FDPS). In embodiments, the at least one encoded genetic element includes a microRNA or a shRNA.

In another aspect, the at least one encoded genetic element includes a shRNA having at least 80%, or at least 85%, or at least 90%, or at least 95% percent identity with v In a preferred embodiment, the shRNA includes SEQ ID NO: 1; SEQ ID NO: 2; SEQ ID NO: 3; or SEQ ID NO: 4.

In another aspect, the at least one encoded genetic element includes a microRNA having at least 80%, or at least 85%, or at least 90%, or at least 95% percent identity with SEQ ID NO: 5; SEQ ID NO: 6; SEQ ID NO: 7; SEQ ID NO: 8; SEQ ID NO: 9; or SEQ ID NO: 10. In a preferred embodiment, the microRNA includes SEQ ID NO: 5; SEQ ID NO: 6; SEQ ID NO: 7; SEQ ID NO: 8; SEQ ID NO: 9; or SEQ ID NO: 10.

In embodiments, the viral vector is comprised of any vector that can effectively transduce the small RNA into a target cell. In embodiments, the viral vector is a lentiviral vector. In other embodiments, the viral vector is an adeno-associated virus vector.

In another aspect, the viral vector includes a second encoded genetic element. In embodiments, the second genetic element includes at least one cytokine or chemokine. In embodiments, the at least one cytokine is selected from the group consisting of: IL-18, TNF-α, interferon-γ, IL-1, IL-2, IL-15, IL-17, and IL-12. In embodiments, the at least one chemokine is a CC chemokine or a CXC chemokine. In further embodiments, the at least one chemokine is RANTES.

In another aspect, a lentiviral vector system for expressing a lentiviral particle is provided. The system includes a lentiviral vector, at least one envelope plasmid for expressing an envelope protein optimized for infecting a cell; and at least one helper plasmid for expressing gag, pol, and rev genes. When the lentiviral vector, the at least one envelope plasmid, and the at least one helper plasmid are transfected into a packaging cell, a lentiviral particle is produced by the packaging cell. In embodiments, the lentiviral particle is capable of infecting a targeting cell, and inhibiting an enzyme involved in the mevalonate pathway within the target cell. In embodiments, the enzyme involved in the mevalonate pathway is FDPS. In embodiments, the lentiviral vector system includes a first helper plasmid for expressing the gag and pol genes, and a second helper plasmid for expressing the rev gene. In embodiments, the envelope protein is preferably optimized for infecting a target cell. In embodiments, the target cell is a cancer cell. In other embodiments, the target cell is a cell that is infected with an infectious agent.

DETAILED DESCRIPTION

Overview of Disclosure

Figure 1:
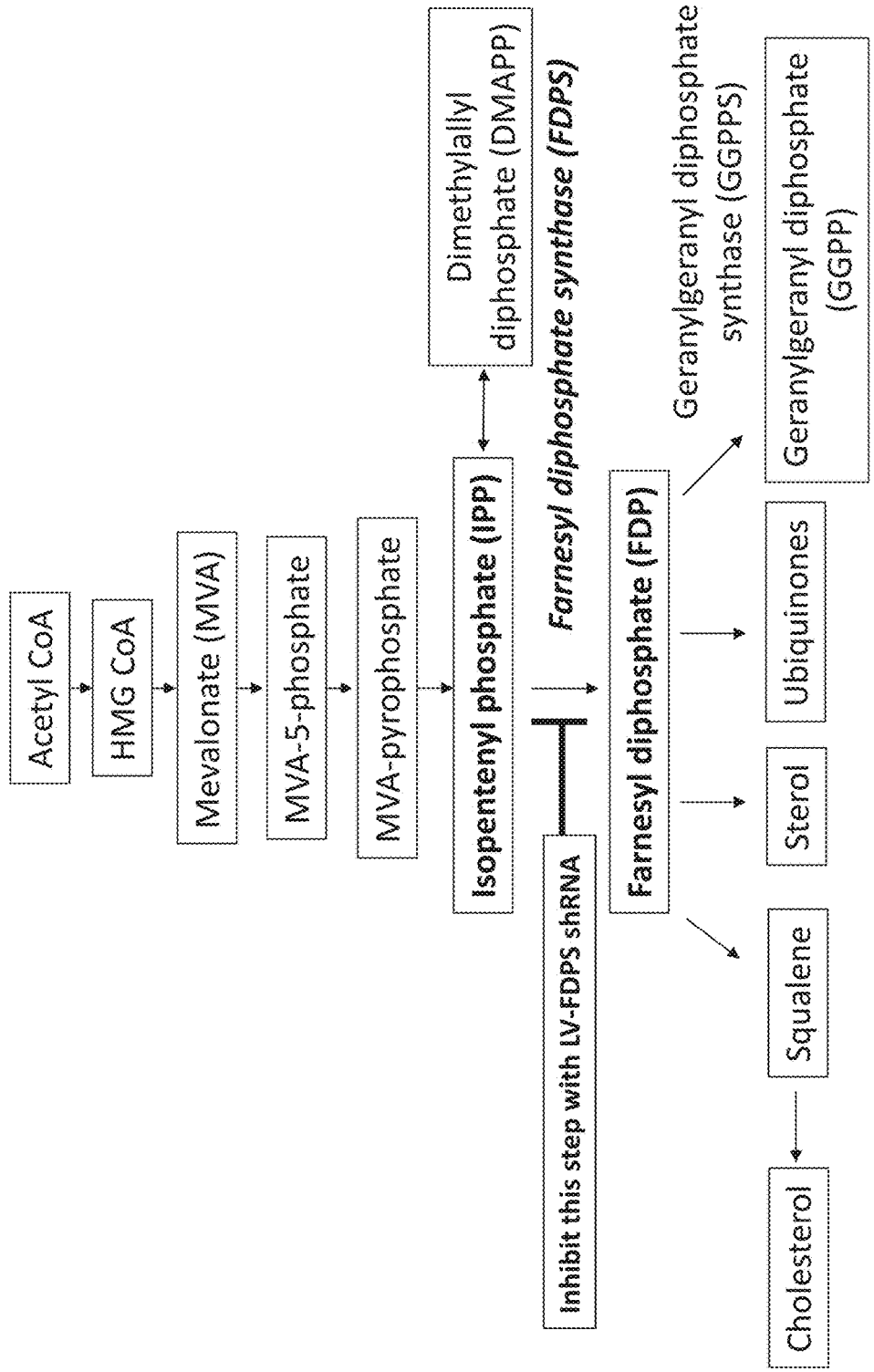
FIG. 1 depicts an overview of the major steps in the mevalonate pathway for biosynthesis of steroids and isoprenoids.

The present disclosure relates to gene therapy constructs and delivery of the same to cells, resulting in suppression of Farnesyl diphosphate synthase ("FDPS"), which is necessary to convert isopentenyl phosphate (IPP) to farnesyl diphosphate (FDP), as shown, for example, in FIG. 1. In embodiments, one or more viral vectors are provided with microRNAs or short homology RNAs (shRNA) that target FDPS, thereby reducing expression levels of this enzyme. The viral vectors include lentiviral vectors and AAV vectors. A consequence of modulating expression of FDPS is to increase the accumulation of IPP, which is a stimulator of GD T cell proliferation and differentiation. Accordingly, the constructs provided herein are used to activate GD T cells, and are used to treat cancers and infectious diseases.

Definitions and Interpretation

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g.: Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual; Cold Spring Harbor Laboratory Press, Cold Spring Harbor, N.Y. (1998); and Coligan et al., Short Protocols in Protein Science, Wiley, John & Sons, Inc. (2003). Any enzymatic reactions or purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art.

As used in the description and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The terms "administration of" or "administering" an active agent should be understood to mean providing an active agent to the subject in need of treatment in a form that can be introduced into that individual's body in a therapeutically useful form and therapeutically effective amount.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

As used herein, "expression," "expressed," or "encodes" refers to the process by which polynucleotides are transcribed into mRNA and/or the process by which the transcribed mRNA is subsequently being translated into peptides, polypeptides, or proteins. Expression may include splicing of the mRNA in a eukaryotic cell or other forms of post-transcriptional modification or post-translational modification.

The term "farnesyl diphosphate synthase" may also be referred to herein as FDPS, and may also be referred to herein as farnesyl pyrophosphate synthase or FPPS.

The term "gamma delta T cell" may also be referred to herein as a γδ T cell, or further as a GD T cell. The term "gamma delta T cell activation" refers to any measurable biological phenomenon associated with a gamma delta T cell that is representative of such T cell being activated. Non-limiting examples of such a biological phenomenon include an increase of cytokine production, changes in the qualitative or quantitative composition of cell surface proteins, an increase in T cell proliferation, and/or an increase in T cell effector function, such killing or a target cell or assisting another effector cell to kill a target cell.

The terms "individual," "subject," and "patient" are used interchangeably herein, and refer to any individual mammal subject, e.g., bovine, canine, feline, equine, or human.

The term "miRNA" refers to a microRNA, and also may be referred to herein as "miR".

The term "packaging cell line" refers to any cell line that can be used to express a lentiviral particle.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to the nucleic acid molecules provided in the disclosure. BLAST protein searches can be performed with the XBLAST program, score=50, word-length=3 to obtain amino acid sequences homologous to the protein molecules of the disclosure. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. See http://www.ncbi.nlm.nih.gov.

As used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) J Pharm Sci 66:1-19).

As used herein, the term "SEQ ID NO" is synonymous with the term "Sequence ID No."

As used herein, "small RNA" refers to non-coding RNA that are generally less than about 200 nucleotides or less in length and possess a silencing or interference function. In other embodiments, the small RNA is about 175 nucleotides or less, about 150 nucleotides or less, about 125 nucleotides or less, about 100 nucleotides or less, or about 75 nucleotides or less in length. Such RNAs include microRNA (miRNA), small interfering RNA (siRNA), double stranded RNA (dsRNA), and short hairpin RNA (shRNA). "Small RNA" of the disclosure should be capable of inhibiting or knocking-down gene expression of a target gene, generally through pathways that result in the destruction of the target gene mRNA.

The term "therapeutically effective amount" refers to a sufficient quantity of the active agents of the present disclosure, in a suitable composition, and in a suitable dosage form to treat or prevent the symptoms, progression, or onset of the complications seen in patients suffering from a given ailment, injury, disease, or condition. The therapeutically effective amount will vary depending on the state of the patient's condition or its severity, and the age, weight, etc., of the subject to be treated. A therapeutically effective amount can vary, depending on any of a number of factors, including, e.g., the route of administration, the condition of the subject, as well as other factors understood by those in the art.

As used herein, the term "therapeutic vector" includes, without limitation, reference to a lentiviral vector or an AAV vector.

"A treatment" is intended to target the disease state and combat it, i.e., ameliorate or prevent the disease state. The particular treatment thus will depend on the disease state to be targeted and the current or future state of medicinal therapies and therapeutic approaches. A treatment may have associated toxicities.

The term "treatment" or "treating" generally refers to an intervention in an attempt to alter the natural course of the subject being treated, and can be performed either for prophylaxis or during the course of clinical pathology. Desirable effects include, but are not limited to, preventing occurrence or recurrence of disease, alleviating symptoms, suppressing, diminishing or inhibiting any direct or indirect pathological consequences of the disease, ameliorating or palliating the disease state, and causing remission or improved prognosis.

DESCRIPTION OF ASPECTS OF THE DISCLOSURE

In one aspect, a method of activating a GDT cell is provided. The method includes infecting, in the presence of the GD T cell, a target cell with a viral delivery system encoding at least one genetic element. In embodiments, the at least one encoded genetic element includes a small RNA capable of inhibiting production of an enzyme involved in the mevalonate pathway. In embodiments, the enzyme is FDPS. In embodiments, when the enzyme is inhibited in the target cell, the target cell activates the GD T cell. In embodiments, the target cell is a cancer cell or a cell that has been infected with an infectious agent. In embodiments, the at least one encoded genetic element includes a microRNA or a shRNA.

In embodiments, the at least one encoded genetic element includes a shRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with GTCCTGGAGTACAATGC-CATTCTCGAGAATGGCATTGTACTCCAGGACTTTTT (SEQ ID NO: 1); GCAGGATTTCGTTCAGCACTTCTC-GAGAAGTGCTGAACGAA ATCCTGCTTTTT (SEQ ID NO: 2); GCCATGTACATGGCAGGAATTCTCGAGAA TTCCTGCCATGTACATGGCTTTTT (SEQ ID NO: 3); or GCAGAAGGAGGCTGA GAAAGTCTCGAGACTT-TCTCAGCCTCCTTCTGCTTTTT (SEQ ID NO: 4). In a preferred embodiment, the shRNA includes GTCCTGGAG-TACAATGCCATTCTCGAG AATGGCATTGTACTCCA-GGACTTTTT (SEQ ID NO: 1); GCAGGATTTCGTTCA GCACTTCTCGAGAAGTGCTGAACGAAATCCTGC-TTTTT (SEQ ID NO: 2); GCCA TGTACATGGCAGGAAT-TCTCGAGAATTCCTGCCATGTACATGGCTTTTT (SEQ ID NO: 3); or GCAGAAGGAGGCTGAGAAAGTCTC-GAGACTTTCTCAGCCTCCTT CTGCTTTTT (SEQ ID NO: 4).

In another aspect, the at least one encoded genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with AAGGTATATTGCTGT-TGACAGTGAGCGACACTTTCTCAGCCTCCTTCT-GCGTGAA GCCACAGATGGCAGAAGGAGGCTGAG-AAAGTGCTGCCTACTGCCTCGGACTTCA AGGGGCT (SEQ ID NO: 5); AAGGTATATTGCTGTTGACAGT-GAGCGACACT TTCTCAGCCTCCTTCTGCGTGAA-GCCACAGATGGCAGAAGGCTGAGAAAGTGCT GCCTACTGCCTCGGACTTCAAGGGGCT (SEQ ID NO: 6); TGCTGTTGACAGTG AGCGACTTTCTCAGCCTC-CTTCTGCGTGAAGCCACAGATGGCAGAAGGAG-GCTG AGAAAGTTGCCTACTGCCTCGGA (SEQ ID NO: 7); CCTGGAGGCTTGCTGAAG GCTGTATGCT-GACTTTCTCAGCCTCCTTCTGCTTTTGGCCACTGA-CTGAGCAGAAG GGCTGAGAAAGTCAGGACACAA-GGCCTGTTACTAGCACTCA (SEQ ID NO: 8); CATCTC-CATGGCTGTACCACCTTGTCGGGACTTTCTCAGC-CTCCTTCTGCCTGTTG AATCTCATGGCAGAAGGAG-GCGAGAAAGTCTGACATTTTGGTATCTTTCATCTGA CCA (SEQ ID NO: 9); or GGGCCTGGCTCGAGCA-GGGGGCGAGGGATACTTTCT CAGCCTCCTTCT-GCTGGTCCCCTCCCCGCAGAAGGAGGCTGAGAA-AGTCCTTCCC TCCCAATGACCGCGTCTTCGTCG (SEQ ID NO: 10). In a preferred embodiment, the microRNA includes AAGGTATATTGCTGTTGACAGTGAGC-GACACTTTCTCAGCCT CCTTCTGCGTGAAGCCAC-AGATGGCAGAAGGAGGCTGAGAAAGTGCTGC-CTACT GCCTCGGACTTCAAGGGGCT (SEQ ID NO: 5); AAGGTATATTGCTGTTGACAGT GAGCGA-CACTTTCTCAGCCTCCTTCTGCGTGAAGCCACA-GATGGCAGAAGGGCTG AGAAAGTGCTGCCTACT-GCCTCGGACTTCAAGGGGCT (SEQ ID NO: 6); TGCTG TTGACAGTGAGCGACTTTCTCAGCCTCCT-TCTGCGTGAAGCCACAGATGGCAGAA GGAGGCT-GAGAAAGTTGCCTACTGCCTCGGA (SEQ ID NO: 7); CCTGGAGGCT TGCTGAAGGCTGTATGCT-GACTTTCTCAGCCTCCTTCTGCTTTTGGCCACT-GACTG AGCAGAAGGGCTGAGAAAGTCAGGACA-CAAGGCCTGTTACTAGCACTCA (SEQ ID NO: 8); CATCTCCATGGCTGTACCACCTTGTCGGGACT-TTCTCAGCCTCCTT CTGCCTGTTGAATCTCATG-GCAGAAGGAGGCGAGAAAGTCTGACATTTTGG-TATC TTTCATCTGACCA (SEQ ID NO: 9); or GGGC-CTGGCTCGAGCAGGGGGCGAGGG ATACT-TTCTCAGCCTCCTTCTGCTGGTCCCCTCCCCGCA-GAAGGAGGCTGAGAAA GTCCTTCCCTCCCAAT-GACCGCGTCTTCGTCG (SEQ ID NO: 10).

In another aspect, the target cell is also contacted with an aminobisphosphonate drug. In a preferred embodiment, the aminobisphosphonate drug is zoledronic acid.

In another aspect, a method of treating cancer in a subject is provided. The method includes administering to the subject a therapeutically-effective amount of a viral delivery system encoding at least one genetic element. In embodiments, the at least one encoded genetic element includes a small RNA capable of inhibiting production of an enzyme involved in the mevalonate pathway. In further embodiments, when the enzyme is inhibited in a cancer cell in the presence of a GD T cell, the cancer cell activates the GD T cell, to thereby treat the cancer. In embodiments, the enzyme is FDPS. In embodiments, the at least one encoded genetic element includes a microRNA or a shRNA.

In another aspect, a method of treating an infectious disease in a subject is provided. The method includes administering to the subject a therapeutically-effective amount of a viral delivery system encoding at least one genetic element. In embodiments, the at least one encoded genetic element includes a small RNA capable of inhibiting production of an enzyme involved in the mevalonate pathway. In further embodiments, when the enzyme is inhibited in a cell that is infected with an infectious agent and is in the presence of a GD T cell, the infected cell activates the GD T cell, to thereby treat the infected cell, and the infectious disease. In embodiments, the enzyme is FDPS. In embodiments, the at least one encoded genetic element includes a microRNA or a shRNA.

In embodiments, the at least one encoded genetic element includes a shRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 1; SEQ ID NO: 2; SEQ ID NO: 3; or SEQ ID NO: 4. In a preferred embodiment, the shRNA includes SEQ ID NO: 1; SEQ ID NO: 2; SEQ ID NO: 3; or SEQ ID NO: 4.

In other embodiments, the at least one encoded genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 5; SEQ ID NO: 6; SEQ ID NO: 7; SEQ ID NO: 8; SEQ ID NO: 9; or SEQ ID NO: 10. In a preferred embodiment, the microRNA includes SEQ ID NO: 5; SEQ ID NO: 6; SEQ ID NO: 7; SEQ ID NO: 8; SEQ ID NO: 9; or SEQ ID NO: 10.

In another aspect, a viral vector comprising at least one encoded genetic element is provided. The at least one encoded genetic element includes a small RNA capable of inhibiting production of an enzyme involved in the mevalonate pathway. In embodiments, the enzyme involved in the mevalonate pathway is farnesyl diphosphate synthase (FDPS). In embodiments, the at least one encoded genetic element includes a microRNA or a shRNA.

In another aspect, the at least one encoded genetic element includes a shRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 1; SEQ ID NO: 2; SEQ ID NO: 3; or SEQ ID NO: 4. In a preferred embodiment, the shRNA includes SEQ ID NO: 1; SEQ ID NO: 2; SEQ ID NO: 3; or SEQ ID NO: 4.

In another aspect, the at least one encoded genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 5; SEQ ID NO: 6; SEQ ID NO: 7; SEQ ID NO: 8; SEQ ID NO: 9; or SEQ ID NO: 10. In a preferred embodiment, the microRNA includes SEQ ID NO: 5; SEQ ID NO: 6; SEQ ID NO: 7; SEQ ID NO: 8; SEQ ID NO: 9; or SEQ ID NO: 10.

In embodiments, the viral vector includes any vector that can effectively transduce the small RNA. In embodiments, the viral vector is a lentiviral vector. In other embodiments, the viral vector is an adeno-associated virus (AAV) vector.

In another aspect, the viral vector includes a second encoded genetic element. In embodiments, the second genetic element includes at least one cytokine or chemokine. In embodiments, the at least one cytokine is selected from the group consisting of: IL-18, TNF-α, interferon-γ, IL-1, IL-2, IL-15, IL-17, and IL-12. In embodiments, the at least one chemokine is a CC chemokine, CXC chemokine, c CX3 chemokine or a XC chemokine. In a further embodiment, the at least one chemokine is the CC chemokine, RANTES.

In another aspect, a lentiviral vector system for expressing a lentiviral particle is provided. The system includes a lentiviral vector, at least one envelope plasmid for expressing an envelope protein optimized for infecting a cell; and at least one helper plasmid for expressing gag, pol, and rev genes. When the lentiviral vector, the at least one envelope plasmid, and the at least one helper plasmid are transfected into a packaging cell, a lentiviral particle is produced by the packaging cell. In embodiments, the lentiviral particle is capable of infecting a targeting cell, and inhibiting an enzyme involved in the mevalonate pathway within the target cell. In embodiments, the enzyme involved in the mevalonate pathway is FDPS. In embodiments, the lentiviral vector system includes a first helper plasmid for expressing the gag and pol genes, and a second helper plasmid for expressing the rev gene. In embodiments, the envelope protein is preferably optimized for infecting a target cell. In embodiments, the target cell is a cancer cell. In other embodiments, the target cell is a cell that is infected with an infectious disease.

Cancer

The compositions and methods provided herein are used to treat cancer. A cell, tissue, or target may be a cancer cell, a cancerous tissue, harbor cancerous tissue, or be a subject or patient diagnosed or at risk of developing a disease or condition. In certain aspects, a cell may be an epithelial, an endothelial, a mesothelial, a glial, a stromal, or a mucosal cell. The cancer cell population can include, but is not limited to a brain, a neuronal, a blood, an endometrial, a meninges, an esophageal, a lung, a cardiovascular, a liver, a lymphoid, a breast, a bone, a connective tissue, a fat, a retinal, a thyroid, a glandular, an adrenal, a pancreatic, a stomach, an intestinal, a kidney, a bladder, a colon, a prostate, a uterine, an ovarian, a cervical, a testicular, a splenic, a skin, a smooth muscle, a cardiac muscle, or a striated muscle cell, can also include a cancer cell population from any of the foregoing, and can be associated with one or more of carcinomas, sarcomas, myelomas, leukemias, lymphomas, mixed types or mixtures of the foregoing. In still a further aspect cancer includes, but is not limited to astrocytoma, acute myeloid leukemia, anaplastic large cell lymphoma, acute lymphoblastic leukemia, angiosarcoma, B-cell lymphoma, Burkitt's lymphoma, breast carcinoma, bladder carcinoma, carcinoma of the head and neck, cervical carcinoma, chronic lymphoblastic leukemia, chronic myeloid leukemia, colorectal carcinoma, endometrial carcinoma, esophageal squamous cell carcinoma, Ewing's sarcoma, fibrosarcoma, glioma, glioblastoma, gastrinoma, gastric carcinoma, hepatoblastoma, hepatocellular carcinoma, Kaposi's sarcoma, Hodgkin lymphoma, laryngeal squamous cell carcinoma, larynx carcinoma, leukemia, leiomyosarcoma, lipoma, liposarcoma, melanoma, mantle cell lymphoma, medulloblastoma, mesothelioma, myxofibrosarcoma, myeloid leukemia, mucosa-associated lymphoid tissue B cell lymphoma, multiple myeloma, high-risk myelodysplastic syndrome, nasopharyngeal carcinoma, neuroblastoma, neurofibroma, high-grade non-Hodgkin lymphoma, non-Hodgkin lymphoma, lung carcinoma, non-small cell lung carcinoma, ovarian carcinoma, oesophageal carcinoma, osteosarcoma, pancreatic carcinoma, pheochromocytoma, prostate carcinoma, renal cell carcinoma, retinoblastoma, rhabdomyosarcoma, salivary gland tumor, Schwanomma, small cell lung cancer, squamous cell carcinoma of the head and neck, testicular tumor, thyroid carcinoma, urothelial carcinoma, and Wilm's tumor.

The compositions and methods provided herein are also used to treat NSCLC (non-small cell lung cancer), pediatric malignancies, cervical and other tumors caused or promoted by human papilloma virus (HPV), melanoma, Barrett's esophagus (pre-malignant syndrome), adrenal and skin cancers and auto immune, neoplastic cutaneous diseases.

Infectious Diseases

The compositions and methods disclosed herein can be used to treat infectious diseases. The term "infectious disease" includes any disease that is caused by an infectious agent. An "infectious agent" includes any exogenous pathogen including, without limitation, bacteria, fungi, viruses, mycoplasma, and parasites. Infectious agents that may be treated with compositions provided for in this disclosure include any art-recognized infectious organisms that cause pathogenesis in an animal, including such organisms as bacteria that are gram-negative or gram-positive cocci or bacilli, DNA and RNA viruses, including, but not limited to, DNA viruses such as papilloma viruses, parvoviruses, adenoviruses, herpesviruses and vaccinia viruses, and RNA viruses, such as arenaviruses, coronaviruses, rhinoviruses, respiratory syncytial viruses, influenza viruses, picornaviruses, paramyxoviruses, reoviruses, retroviruses, and rhabdoviruses. Examples of fungi that may be treated with the compositions and methods of the disclosure include fungi that grow as molds or are yeast like, including, for example, fungi that cause diseases such as ringworm, histoplasmosis, blastomycosis, aspergillosis, cryptococcosis, sporotrichosis, coccidioidomycosis, paracoccidio-idomycosis, and candidiasis. Compositions and methods provided for herein may be utilized to treat parasitic infections including, but not limited to, infections caused by somatic tapeworms, blood flukes, tissue roundworms, ameba, and *Plasmodium, Trypanosoma, Leishmania,* and *Toxoplasma* species.

Methods of GD T Cell Activation

Provided herein are compositions and methods for activating GD T cells in an individual, as well as methods for treating tumors and infectious diseases. For instance, in embodiments, the compositions and methods provided herein can be used in methods to treat all known cancers because activated GD T cells comprise a natural mechanism for immune surveillance of tumors (See for e.g.: Pauza et al. 2014 *Frontiers in Immunol.* 5:687). Likewise, in embodiments, the compositions and methods provided herein can be used to treat infectious diseases, including but not limited to flavivirus, influenza virus, human retrovirus, mycobacteria, plasmodia and a variety of other viral, fungal and bacterial infections. (See for e.g.: Pauza and Cairo, 2015 *Cell Immunol.* 296(1).

In general, a vector system is administered to an individual to transfect or transduce a target cell population with the disclosed constructs for decreasing expression of FDPS and, in other embodiments, increasing expression of chemokines or cytokines. Administration and transfection/transduction can occur in vivo or ex vivo, with the transfected cells later administered back into the subject in the latter scenario.

Administration of the disclosed vectors and transfection or transduction of the disclosed constructs into a subject's cells result in decreased expression of FDPS, increased expression of cytokines or chemokines, accumulation of IPP and in many cases, reduced growth rates for genetically modified tumor cells. All of these features work together to activate and co-localize GD T cells to the site of a tumor or infection.

The disclosed methods can also increase the capacity of NK cells to recognize and destroy tumor cells and/or infected cells. Crosstalk between GD T cells and NK cells is an important aspect of regulating the immune and inflammatory responses. Further, GD T cells are known to trigger dendritic cell maturation, recruit B cells and macrophages, and participate in a variety of cytolytic activities, such as secretion of interferon-γ and TNF-α.

In embodiments, the disclosed compositions and methods provided herein comprise a form of gene therapy for activating GD T cells at the site of tumor or infectious disease pathology. In an aspect, the compositions and methods provided herein activate GD T cells and support their proliferation, differentiation, and functional capacities by promoting the production of specific cytokines needed for cytolytic activity capable of killing cancer cells or treating infectious diseases.

In embodiments the gene therapy sequences (e.g., FDPS shRNAs) are carried by therapeutic vectors, including but not limited to viral vectors such as lentiviruses or adeno-associated viruses, although other viral vectors can also be suitable. Gene therapy constructs may also be delivered in the form of DNA or RNA, including but not limited to plasmid forms. In embodiments, the disclosed gene therapy constructs may also be delivered in the form of protein-nucleic acid complexes or lipid nucleic acid complexes and mixtures of these formulations. For instance, a protein-nucleic acid complex can comprise nucleic acids of interest in a complex with cationic peptides such as lysine and arginine. Lipid-nucleic acids complexes can comprise lipid emulsions, micelles, liposomes, and/or mixtures of neutral and cationic lipids such as DOTMA, DOSPA, DOTAP, and DMRIE.

In embodiments, therapeutic vectors may comprise a single construct or at least two, at least three, at least four, or at least five different constructs. When more than one construct is present in a vector the constructs may be identical, or they may be different. For instance, the constructs may vary in terms of their promoters, the presence or absence of an integrating elements, and/or their sequences. In some embodiments, a therapeutic vector will comprise at least one construct that encodes a small RNA capable of knocking down the expression of FDPS. In embodiments, the therapeutic vector will also encode a specific cytokine(s) and/or chemokine(s), including but not limited to TNF-α, interferon-γ, IL-1, IL-2, IL-15, IL-17, IL-18 or IL-12. In some embodiments, a single construct may encode both small RNAs capable of knocking down the expression of FDPS and specific cytokines or chemokines, including but not limited to TNF-α, interferon-γ, IL-1, IL-2, IL-15, IL-17, IL-18 or IL-12.

In embodiments, viral vectors may introduce nucleic acid constructs that become integrated into the host chromosome. Alternately, transient delivery vectors may be used to prevent chromosomal integration and limit the lifespan of gene therapy constructs.

In embodiments, the disclosed constructs and vectors comprise short homology region RNA ("shRNA"), micro RNA ("miRNA"), or siRNA capable of reducing or knocking down expression of FDPS and/or geranyl pyrophosphate synthase ("GPPS") and/or farnesyl transferase ("FT") genes. By down regulating these genes, which control steroid and isoprenoid synthesis, isopentenyl pyrophosphate ("IPP") levels are elevated. Elevation and accumulation of IPP is a known mechanism for increasing GD T cells activation. Further, down regulation of these pyrophosphate synthase genes removes an important negative regulator of inflammasome function that in turn results in increased expression of cytokines that are important for GD T cell activation and effector cell function.

In embodiments, the disclosed constructs are regulated by specific promoters that are capable of producing interleukin-2 and/or interleukin-15 to sustain GD T cell proliferation. In addition, the disclosed constructs may be regulated by specific promoters that are capable of producing interleukin-1 beta and/or interleukin-18 and/or interferon-gamma required for GD T cell differentiation and acquisition of all effector cell function. Desirable effector cell functions include the capacity for direct cytotoxic cell killing of tumors and/or infected cells, secretion of beneficial cytokines and/or chemokines, increased expression of NK receptors required to recognize cancerous or infected cells, and increased expression of Fc receptors needed to bind targeting antibodies in order to co-localize GD T cells with cancerous or infected cell targets.

In embodiments, the disclosed methods activate GD T cells, resulting in the indirect effect of increasing the capacity for NK cells to attack and destroy cancerous cells, tumors, or infected cells. The activation of NK cells requires GD T cells that are stimulated to proliferate and differentiate, and to express 4-1BBL costimulatory ligand needed to engage the 4-1BB costimulatory receptor on NK cells. This form of crosstalk is known as an important mechanism for activating NK cells and is achieved here through the action of the disclosed methods and compositions.

In another aspect, crosstalk between GD T cells and NK cells is an important mechanism for eliminating inflammatory dendritic cells that accumulate in diseased tissues. Alone, neither GD T cells nor NK cells are capable of destroying dendritic cells, but once the aforementioned crosstalk interactions have occurred, NK cells are altered to become cytotoxic against inflammatory dendritic cells. This immuno-regulatory mechanism depends on strong activation and proliferation of GD T cells.

In embodiments, the disclosed methods for activation of GD T cells further comprise a step of suppressing pathologic inflammatory responses that may include cellular proliferation leading to atherosclerosis, chronic immune activation that stimulates tumor growth, autoimmune diseases including psoriasis and other presentations in the epidermis, inflammatory diseases of the central nervous system, and arthritis and other diseases of unregulated immune responses.

In embodiments, therapeutic vectors are administered concurrently with aminobisphosphonate (ABP) drugs to achieve synergistic activation of gamma delta T cells. The synergism can allow alternate, modified or reduced doses of ABP and may decrease adverse reactions to ABP including acute inflammatory responses and chronic diseases.

Constructs for GD T Cell Activation

Inhibition of FDPS results in IPP accumulation, resulting in activation of Vδ2+ GD T cells and expression of IL-18, which is also important in activating GD T cells. Inhibition of farnesyl transferase results in decreased prenylation of proteins. The disclosed constructs can be transfected or transduced into specific target cells, like tumor cells or infected cells, where they can express RNA sequences (i.e., siRNA, shRNA or microRNA) that will inhibit translation of FDPS as well as encode and express cytotoxic cytokines or chemokines.

Disclosed herein are constructs for decreasing expression of FDPS and/or FT, increasing expression of cytokines, and increasing expression of chemokines including RANTES. For instance, in some embodiments the constructs may encode for interferon-gamma, IL-1, IL-2, IL-15, IL-17, IL-18 or IL-12.

Expression of cytokines and chemokines, like those listed above, will result in localized cytotoxic destruction of tumor cells or cells infected with pathogenic organisms. Accordingly, expression of such constructs by a tumor cell or an infected cell will result in the unwanted cells assisting in its own destruction.

Likewise, if the disclosed constructs are expressed in a tumor cell or infected cell, decreasing the expression of FDPS and FT will result in activation and recruitment of GD T cells to the tumor site of site of cell infection. Increasing expression of RANTES will further attract GD T cells to intended tissue location. Because GD T cells can kill a broad range of tumors of epithelial origin as well as many leukemias and lymphomas, and are further able to produce high levels of the anti-tumor cytokine, IFNγ, recruitment of GD T cells to the site of a tumor can be a particularly effective means of inducing anti-tumor immunity.

Decreased expression of FDPS can be achieved via shRNA, microRNA, siRNA, or other means known in the art. For instance, shRNAs according to SEQ ID NOS: 1, 2, 3, or 4, or variants thereof can be used in the disclosed constructs and methods, although this example is not limiting. The coding regions for RNAs to decrease expression of FDPS and FT and the coding regions of cytokine and chemokines may be in the same construct or on different constructs.

The classical approach for the production of recombinant polypeptides or gene regulatory molecules including small RNA is the use of stable expression constructs. These constructs are based upon chromosomal integration of a transduced expression plasmid (or at least a portion thereof) into the genome of the host cell, short-duration plasmid transfection, or non-integrating viral vectors also with limited half-life. The sites of gene integration are generally random, and the number and ratio of genes integrating at any particular site are often unpredictable; likewise, non-integrating plasmids or viral vectors also generate nuclear DNA but these species usually lack sequences required for DNA replication and continuous maintenance. Thus, constructs that rely on chromosomal integration result in permanent maintenance of the recombinant gene that may exceed the therapeutic interval.

An alternative to stable expression constructs for gene expression are transient expression constructs. The expression of the latter gene expression construct is based on non-integrated plasmids, and hence the expression is typically lost as the cell undergoes division or the plasmid vectors are destroyed by endogenous nucleases.

The disclosed constructs are preferably episomal constructs that are transiently expressed. Episomal constructs are degraded or diluted over time such that they do not make permanent changes to a subject's genome, nor are they incorporated into the chromosome of a target cell. The process of episomal replication typically incorporates both host cell replication machinery and viral trans-acting factors.

Avoiding chromosomal integration reduces certain barriers to in vivo gene delivery. However, even integration-defective constructs can have a background frequency of integration, and any DNA molecule can find rare homologies to recombine with host sequences; but these rates of integration are exceptionally rare and generally not clinically significant.

Thus, in some embodiments, the disclosed vectors support active gene and/or small RNA delivery over a period of about 1, about 2, about 3, about 4, about 5, about 6, about 7, about 8, about 9, about 10, about 11, or about 12 weeks. In some embodiments, the disclosed vectors support active gene and/or small RNA delivery over a period of about 1 month, 2 months, 3 months, 4 months, 5 months, 6 months, 7 months, 8 months, 9 months, 10 months, 11 months, 12 months, or longer. Any combination of these time periods can also be used in the methods of the invention, e.g., 1 month and 1 week, or 3 months and 2 weeks.

However, in some embodiments, the constructs comprise integrating elements that depend on a retroviral integrase gene, such that the construct becomes integrated into the subject's chromosome. Retrotransposition and transposition are additional examples of mechanisms whereby mobile genetic elements become integrated or inserted into the chromosome. Plasmids may become integrated into the chromosome by recombination, and gene editing technologies including CRISPR and TALEN utilize guide RNA sequences and alter chromosomal loci by gene conversion mechanisms.

Constructs may comprise specific promoters for expressing cytokines involved in the maintenance of GD T cells (i.e. IL-2, IL-7, IL-17, and IL-15). For example, promoters that may be incorporated into the disclosed constructs include but are not limited to TATA-box promoters, CpG-box promoters, CCAAT-box promoters, TTGACA-box promoters, BRE-box promoters, INR-box promoters, AT-based promoters, CG-based promoters, ATCG-compact promoters, ATCG-balanced promoters, ATCG-middle promoters, ATCG-less promoters, AT-less promoters, CG-less promoters, AT-spike promoters, and CG-spike promoters. See Gagniuc and Ionescu-Tirgoviste, *Eukaryotic genomes may exhibit up to* 10 *generic classes of gene promoters*, BMC GENOMICS 13:512 (2012).

Therapeutic Vectors

The construct can be delivered via known transfection and/or transduction vectors, including but not limited to lentiviral vectors, adeno-associated virus, poxvirus, herpesvirus vectors, protein and/or lipid complexes, liposomes, micelles, and the like.

Viral vectors can be preferentially targeted to cell types that are useful for the disclosed methods (i.e., tumor cells or myeloid cells). Viral vectors can be used to transduce genes into target cells owing to specific virus envelope-host cell receptor interactions and viral mechanisms for gene expression. As a result, viral vectors have been used as vehicles for the transfer of genes into many different cell types including whole embryos, fertilized eggs, isolated tissue samples, tissue targets in situ, and cultured cell lines. The ability to introduce and express foreign genes in a cell is useful for the study of gene expression, and the elucidation of cell lineages as well as providing the potential for therapeutic interventions such as gene therapy, somatic cell reprogramming of induced pluripotent stem cells, and various types of immunotherapy. Viral components from viruses like Papovaviridae (e.g. bovine papillomavirus or BPV) or Herpesviridae (e.g. Epstein Barr Virus or EBV) or Hepadnaviridae (e.g. Hepatitis B Virus or HBV) or pox vectors including vaccinia may be used in the disclosed vectors.

Lentiviral vectors are a preferred type of vector for the disclosed compositions and methods, although the disclosure is not specifically limited to lentiviral vectors. Lentivirus is a genus of viruses that can deliver a significant amount of viral nucleic acid into a host cell. Lentiviruses are characterized as having a unique ability to infect/transduce non-dividing cells, and following transduction, lentiviruses integrate their nucleic acid into the host cell's chromosomes.

Infectious lentiviruses have three main genes coding for the virulence proteins gag, pol, and env, and two regulatory genes including tat and rev. Depending on the specific serotype and virus, there may be additional accessory genes that code for proteins involved in regulation, synthesis, and/or processing viral nucleic acids and other replicative functions.

Moreover, lentiviruses contain long terminal repeat (LTR) regions, which may be approximately 600 nt long. LTRs may be segmented into U3, R, and U5 regions. LTRs can mediate integration of retroviral DNA into the host chromosome via the action of integrase. Alternatively, without functioning integrase, the LTRs may be used to circularize the viral nucleic acid.

Viral proteins involved in early stages of lentivirus replication include reverse transcriptase and integrase. Reverse transcriptase is the virally encoded, RNA-dependent DNA polymerase. The enzyme uses a viral RNA genome as a template for the synthesis of a complementary DNA copy. Reverse transcriptase also has RNaseH activity for destruction of the RNA-template. Integrase binds both the viral cDNA generated by reverse transcriptase and the host DNA. Integrase processes the LTR before inserting the viral genome into the host DNA. Tat acts as a trans-activator during transcription to enhance initiation and elongation. The rev responsive element acts post-transcriptionally, regulating mRNA splicing and transport to the cytoplasm.

Viral vectors, in general, comprise glycoproteins and the various glycoproteins may provide specific affinities. For instance, VSVG peptides can increase transfection into myeloid cells. Alternatively, viral vectors can also have targeting moieties, such as antibodies, attached to their shell peptides. Targeting antibodies can be specific for antigens that are overexpressed on a tumor, for instance, like HER-2, PSA, CEA, M2-PK, and CA19-9.

Other viral vector specificities are also known in the art and can be used to target particular populations of cells. For example, poxvirus vectors target to macrophages and dendritic cells.

Lentiviral Vector System

A lentiviral virion (particle) is expressed by a vector system encoding the necessary viral proteins to produce a virion (viral particle). There is at least one vector containing a nucleic acid sequence encoding the lentiviral poi proteins necessary for reverse transcription and integration, operably linked to a promoter. In another embodiment, the pol proteins are expressed by multiple vectors. There is also a vector containing a nucleic acid sequence encoding the lentiviral gag proteins necessary for forming a viral capsid operably linked to a promoter. In an embodiment, this gag nucleic acid sequence is on a separate vector than at least some of the poi nucleic acid sequence. In another embodiment, the gag nucleic acid is on a separate vector from all the poi nucleic acid sequences that encode pol proteins.

Numerous modifications can be made to the vectors, which are used to create the particles to further minimize the chance of obtaining wild type revertants. These include, but are not limited to deletions of the U3 region of the LTR, tat deletions and matrix (MA) deletions.

The gag, poi and env vector(s) do not contain nucleotides from the lentiviral genome that package lentiviral RNA, referred to as the lentiviral packaging sequence.

The vector(s) forming the particle preferably do not contain a nucleic acid sequence from the lentiviral genome that expresses an envelope protein. Preferably, a separate vector that contains a nucleic acid sequence encoding an envelope protein operably linked to a promoter is used. This env vector also does not contain a lentiviral packaging sequence. In one embodiment the env nucleic acid sequence encodes a lentiviral envelope protein.

In another embodiment the envelope protein is not from the lentivirus, but from a different virus. The resultant particle is referred to as a pseudotyped particle. By appropriate selection of envelopes one can "infect" virtually any cell. For example, one can use an env gene that encodes an envelope protein that targets an endocytic compartment such as that of the influenza virus. VSV-G, alpha viruses (Semliki forest virus, Sindbis virus), arenaviruses (lymphocytic choriomeningitis virus), flaviviruses (tick-borne encephalitis virus, Dengue virus, hepatitis C virus, GB virus), rhabdoviruses (vesicular stomatitis virus, rabies virus), paramyxoviruses (mumps or measles) and orthomyxoviruses (influenza virus). Other envelopes that can preferably be used include those from Moloney Leukemia. Virus such as MLV-E, MLV-A and GALV. These latter envelopes are particularly preferred where the host cell is a primary cell. Other envelope proteins can be selected depending upon the desired host cell. For example, targeting specific receptors such as a dopamine receptor can be used for brain delivery. Another target can be vascular endothelium. These cells can be targeted using a filovirus envelope. For example, the GP of Ebola, which by post-transcriptional modification become the GP, and $GP_2$ glycoproteins. In another embodiment, one can use different lentiviral capsids with a pseudotyped envelope (for example, FIV or SHIV [U.S. Pat. No. 5,654, 195]). A SHIV pseudotyped vector can readily be used in animal models such as monkeys.

As detailed herein, a lentiviral vector system typically includes at least one helper plasmid comprising at least one of a gag, pol, or rev gene. Each of the gag, pol and rev genes may be provided on individual plasmids, or one or more genes may be provided together on the same plasmid. In one embodiment, the gag, pol, and rev genes are provided on the same plasmid (e.g., FIG. 2). In another embodiment, the gag and pol genes are provided on a first plasmid and the rev gene is provided on a second plasmid (e.g., FIG. 3). Accordingly, both 3-vector and 4-vector systems can be used to produce a lentivirus as described in the Examples section and elsewhere herein. The therapeutic vector, the envelope plasmid and at least one helper plasmid are transfected into a packaging cell line. A non-limiting example of a packaging cell line is the 293T/17 HEK cell line. When the therapeutic vector, the envelope plasmid, and at least one helper plasmid are transfected into the packaging cell line, a lentiviral particle is ultimately produced.

In another aspect, a lentiviral vector system for expressing a lentiviral particle is disclosed. The system includes a lentiviral vector as described herein; an envelope plasmid for expressing an envelope protein optimized for infecting a cell; and at least one helper plasmid for expressing gag, pol, and rev genes, wherein when the lentiviral vector, the envelope plasmid, and the at least one helper plasmid are transfected into a packaging cell line, a lentiviral particle is produced by the packaging cell line, wherein the lentiviral particle is capable of inhibiting production of chemokine receptor CCR5 or targeting an HIV RNA sequence.

In another aspect, and as detailed in FIG. 2, the lentiviral vector, which is also referred to herein as a therapeutic vector, can include the following elements: hybrid 5' long terminal repeat (RSV/5' LTR) (SEQ ID NOS: 11-12), Psi sequence (RNA packaging site) (SEQ ID NO: 13), RRE (Rev-response element) (SEQ ID NO: 14), cPPT (polypurine tract) (SEQ ID NO: 15), H1 promoter (SEQ ID NO: 16), FDPS shRNA (SEQ ID NOS: 1, 2, 3, 4), Woodchuck Post-Transcriptional Regulatory Element (WPRE) (SEQ ID NO: 17), and 3' Delta LTR (SEQ ID NO: 18). In another aspect, sequence variation, by way of substitution, deletion, addition, or mutation can be used to modify the sequences references herein.

In another aspect, and as detailed herein, a helper plasmid has been designed to include the following elements: CAG promoter (SEQ ID NO: 19); HIV component gag (SEQ ID NO: 20); HIV component pol (SEQ ID NO: 21); HIV Int (SEQ ID NO: 22); HIV RRE (SEQ ID NO: 23); and HIV Rev (SEQ ID NO: 24). In another aspect, the helper plasmid may be modified to include a first helper plasmid for expressing the gag and pol genes, and a second and separate plasmid for expressing the rev gene. In another aspect, sequence variation, by way of substitution, deletion, addition, or mutation can be used to modify the sequences references herein.

In another aspect, and as detailed herein, an envelope plasmid has been designed to include the following elements being from left to right: RNA polymerase II promoter (CMV) (SEQ ID NO: 25) and vesicular stomatitis virus G glycoprotein (VSV-G) (SEQ ID NO: 26). In another aspect, sequence variation, by way of substitution, deletion, addition, or mutation can be used to modify the sequences references herein.

In another aspect, the plasmids used for lentiviral packaging can be modified with similar elements and the intron sequences could potentially be removed without loss of vector function. For example, the following elements can replace similar elements in the plasmids that comprise the packaging system: Elongation Factor-1 (EF-1), phosphoglycerate kinase (PGK), and ubiquitin C (UbC) promoters can replace the CMV or CAG promoter. SV40 poly A and bGH poly A can replace the rabbit beta globin poly A. The HIV sequences in the helper plasmid can be constructed from different HIV strains or clades. The VSV-G glycoprotein can be substituted with membrane glycoproteins from feline endogenous virus (RD114), gibbon ape leukemia virus (GALV), Rabies (FUG), lymphocytic choriomeningitis virus (LCMV), influenza A fowl plague virus (FPV), Ross River alphavirus (RRV), murine leukemia virus 10A1 (MLV), or Ebola virus (EboV).

Of note, lentiviral packaging systems can be acquired commercially (e.g., Lenti-vpak packaging kit from OriGene Technologies, Inc., Rockville, Md.), and can also be designed as described herein. Moreover, it is within the skill of a person skilled in the art to substitute or modify aspects of a lentiviral packaging system to improve any number of relevant factors, including the production efficiency of a lentiviral particle.

Doses and Dosage Forms

The disclosed vectors allow for short, medium, or long-term expression of genes or sequences of interest and episomal maintenance of the disclosed vectors. Accordingly, dosing regimens may vary based upon the condition being treated and the method of administration.

In one embodiment, transduction vectors may be administered to a subject in need in varying doses. Specifically, a subject may be administered about $\geq 10^6$ infectious doses (where 1 dose is needed on average to transduce 1 target cell). More specifically, a subject may be administered about $\geq 10^7$, about $\geq 10^8$, about $\geq 10^9$, or about $\geq 10^{10}$ infectious doses, or any number of doses in-between these values. Upper limits of transduction vector dosing will be determined for each disease indication and will depend on toxicity/safety profiles for each individual product or product lot.

Additionally, a vector of the present disclosure may be administered periodically, such as once or twice a day, or any other suitable time period. For example, vectors may be administered to a subject in need once a week, once every other week, once every three weeks, once a month, every other month, every three months, every six months, every nine months, once a year, every eighteen months, every two years, every thirty months, or every three years.

In one embodiment, the disclosed vectors are administered as a pharmaceutical composition. In some embodiments, the pharmaceutical composition comprising the disclosed vectors can be formulated in a wide variety of dosage forms, including but not limited to nasal, pulmonary, oral, topical, or parenteral dosage forms for clinical application. Each of the dosage forms can comprise various solubilizing agents, disintegrating agents, surfactants, fillers, thickeners, binders, diluents such as wetting agents or other pharmaceutically acceptable excipients. The pharmaceutical composition comprising a vector can also be formulated for injection, insufflation, infusion, or intradermal exposure. For instance, an injectable formulation may comprise the disclosed vectors in an aqueous or non-aqueous solution at a suitable pH and tonicity.

The disclosed vectors may be administered to a subject via direct injection into a tumor site or at a site of infection. In some embodiments, the vectors can be administered systemically. In some embodiments, the vectors can be administered via guided cannulation to tissues immediately surrounding the sites of tumor or infection.

The disclosed vector compositions can be administered using any pharmaceutically acceptable method, such as intranasal, buccal, sublingual, oral, rectal, ocular, parenteral (intravenously, intradermally, intramuscularly, subcutaneously, intraperitoneally), pulmonary, intravaginal, locally administered, topically administered, topically administered after scarification, mucosally administered, via an aerosol, in semi-solid media such as agarose or gelatin, or via a buccal or nasal spray formulation.

Further, the disclosed vector compositions can be formulated into any pharmaceutically acceptable dosage form, such as a solid dosage form, tablet, pill, lozenge, capsule, liquid dispersion, gel, aerosol, pulmonary aerosol, nasal aerosol, ointment, cream, semi-solid dosage form, a solution, an emulsion, and a suspension. Further, the composition may be a controlled release formulation, sustained release formulation, immediate release formulation, or any combination thereof. Further, the composition may be a transdermal delivery system.

In some embodiments, the pharmaceutical composition comprising a vector can be formulated in a solid dosage form for oral administration, and the solid dosage form can be powders, granules, capsules, tablets or pills. In some embodiments, the solid dosage form can include one or more excipients such as calcium carbonate, starch, sucrose, lactose, microcrystalline cellulose or gelatin. In addition, the solid dosage form can include, in addition to the excipients, a lubricant such as talc or magnesium stearate. In some embodiments, the oral dosage form can be immediate release, or a modified release form. Modified release dosage forms include controlled or extended release, enteric release, and the like. The excipients used in the modified release dosage forms are commonly known to a person of ordinary skill in the art.

In a further embodiment, the pharmaceutical composition comprising a vector can be formulated as a sublingual or buccal dosage form. Such dosage forms comprise sublingual tablets or solution compositions that are administered under the tongue and buccal tablets that are placed between the cheek and gum.

In some embodiments, the pharmaceutical composition comprising a vector can be formulated as a nasal dosage form. Such dosage forms of the present invention comprise solution, suspension, and gel compositions for nasal delivery.

In some embodiments, the pharmaceutical composition comprising a vector can be formulated in a liquid dosage form for oral administration, such as suspensions, emulsions or syrups. In some embodiments, the liquid dosage form can include, in addition to commonly used simple diluents such as water and liquid paraffin, various excipients such as humectants, sweeteners, aromatics or preservatives. In particular embodiments, the composition comprising vectors can be formulated to be suitable for administration to a pediatric patient.

In some embodiment, the pharmaceutical composition can be formulated in a dosage form for parenteral administration, such as sterile aqueous solutions, suspensions, emulsions, non-aqueous solutions or suppositories. In some embodiments, the solutions or suspensions can include propyleneglycol, polyethyleneglycol, vegetable oils such as olive oil or injectable esters such as ethyl oleate.

The dosage of the pharmaceutical composition can vary depending on the patient's weight, age, gender, administration time and mode, excretion rate, and the severity of disease.

In some embodiments, the treatment of cancer is accomplished by guided direct injection of the disclosed vector constructs into tumors, using needle, or intravascular cannulation. In some embodiments, the disclosed vectors are administered into the cerebrospinal fluid, blood or lymphatic circulation by venous or arterial cannulation or injection, intradermal delivery, intramuscular delivery or injection into a draining organ near the site of disease.

The following examples are given to illustrate the present invention. It should be understood, however, that the invention is not to be limited to the specific conditions or details described in these examples. All printed publications referenced herein are specifically incorporated by reference.

EXAMPLES

Example 1: Development of a Lentiviral Vector System

Figure 4:
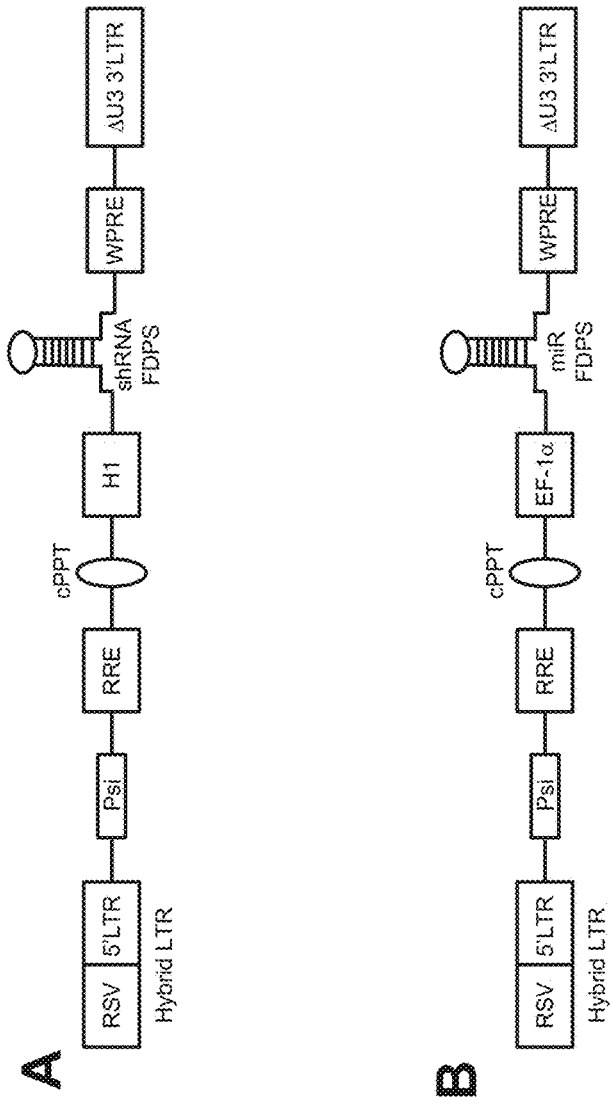
FIG. 4 depicts: (A) a linear map of a lentiviral vector expressing a FDPS shRNA targeting sequence; and (B) a linear map of a lentiviral vector expressing a synthetic microRNA with a FDPS targeting sequence.

A lentiviral vector system was developed as summarized in FIG. 4 (circularized form). Lentiviral particles were produced in 293T/17 HEK cells (purchased from American Type Culture Collection, Manassas, Va.) following transfection with the therapeutic vector, the envelope plasmid, and the helper plasmid. The transfection of 293T/17 HEK cells, which produced functional viral particles, employed the reagent Poly(ethylenimine) (PEI) to increase the efficiency of plasmid DNA uptake. The plasmids and DNA were initially added separately in culture medium without serum in a ratio of 3:1 (mass ratio of PEI to DNA). After 2-3 days, cell medium was collected and lentiviral particles were purified by high-speed centrifugation and/or filtration followed by anion-exchange chromatography. The concentration of lentiviral particles can be expressed in terms of transducing units/ml (TU/ml). The determination of TU was accomplished by measuring HIV p24 levels in culture fluids (p24 protein is incorporated into lentiviral particles), measuring the number of viral DNA copies per cell by quantitative PCR, or by infecting cells and using light (if the vectors encode luciferase or fluorescent protein markers).

Figure 2:
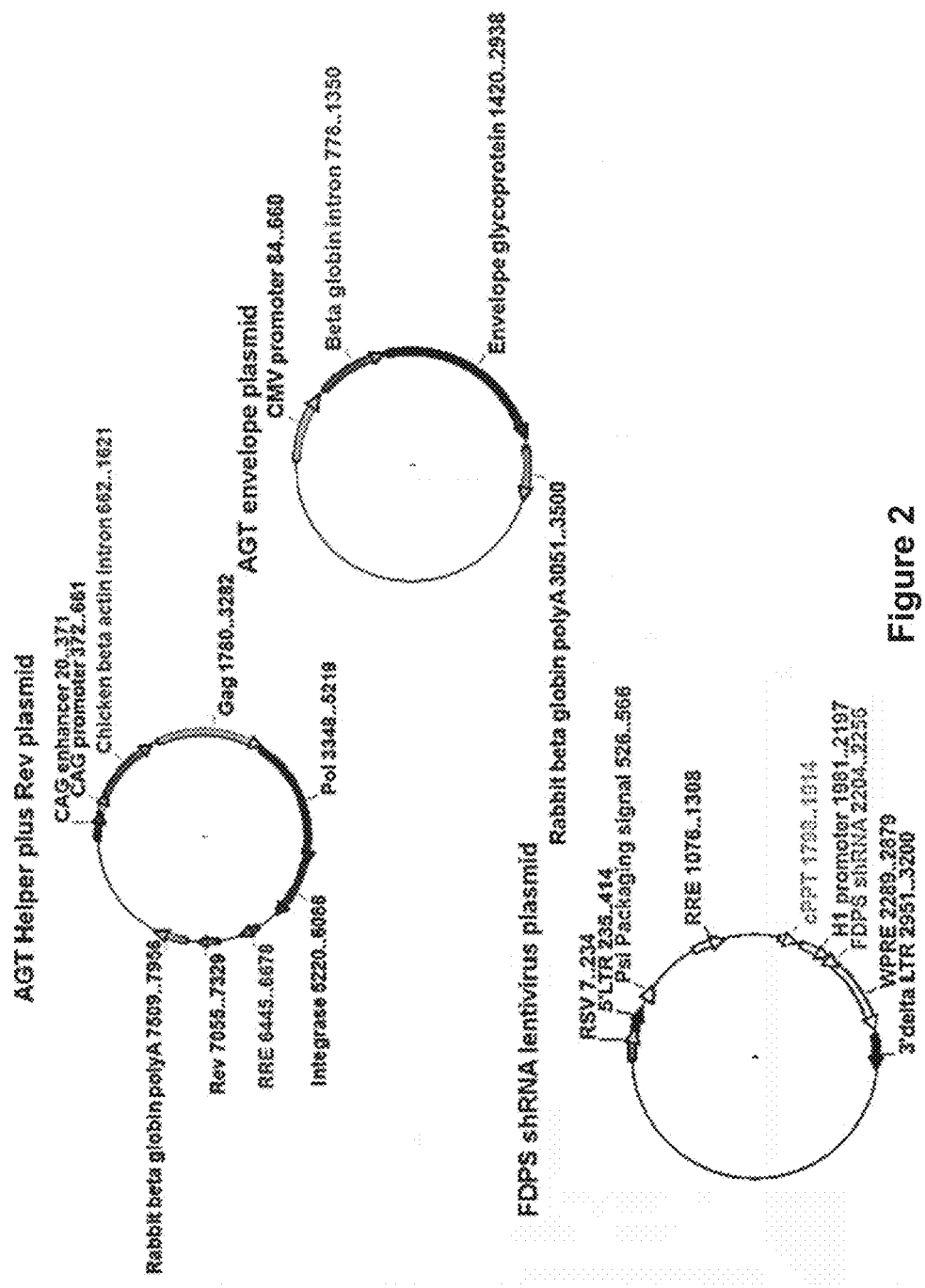
FIG. 2 depicts an exemplary 3-vector lentiviral vector system in a circularized form.

As mentioned above, a 3-vector system (i.e., a 2-vector lentiviral packaging system) was designed for the production of lentiviral particles. A schematic of the 3-vector system is shown in FIG. 2. Briefly, and with reference to FIG. 2, the top-most vector is a helper plasmid, which, in this case, includes Rev. The vector appearing in the middle of FIG. 2 is the envelope plasmid. The bottom-most vector is the therapeutic vector, as described herein.

Referring more specifically to FIG. 2, the Helper plus Rev plasmid includes a CAG enhancer (SEQ ID NO: 27); a CAG promoter (SEQ ID NO: 19); a chicken beta actin intron (SEQ ID NO: 28); a HIV gag (SEQ ID NO: 20); a HIV Pol (SEQ ID NO: 21); a HIV Int (SEQ ID NO: 22); a HIV RRE (SEQ ID NO: 23); a HIV Rev (SEQ ID NO: 24); and a rabbit beta globin poly A (SEQ ID NO: 29).

The Envelope plasmid includes a CMV promoter (SEQ ID NO: 25); a beta globin intron (SEQ ID NO: 30); a VSV-G (SEQ ID NO: 28); and a rabbit beta globin poly A (SEQ ID NO: 31).

Synthesis of a 2-Vector Lentiviral Packaging System Including Helper (Plus Rev) and Envelope Plasmids.

Materials and Methods:

Construction of the Helper Plasmid:

The helper plasmid was constructed by initial PCR amplification of a DNA fragment from the pNL4-3 HIV plasmid (NIH Aids Reagent Program) containing Gag, Pol, and Integrase genes. Primers were designed to amplify the fragment with EcoRI and NotI restriction sites which could be used to insert at the same sites in the pCDNA3 plasmid (Invitrogen). The forward primer was (5'-TAAGCAGAATTC ATGAATTTGCCAGGAAGAT-3') (SEQ ID NO: 32) and reverse primer was (5'-CCATACAATGAATGGACACTAGGCGGCCGCACGAAT-3') (SEQ ID NO: 33).

The sequence for the Gag, Pol, Integrase fragment was as follows:

(SEQ ID NO: 34)
GAATTCATGAATTTGCCAGGAAGATGGAAACCAAAAATGATAGGGGGAAT

TGGAGGTTTTATCAAAGTAAGACAGTATGATCAGATACTCATAGAAATCT

GCGGACATAAAGCTATAGGTACAGTATTAGTAGGACCTACACCTGTCAAC

ATAATTGGAAGAAATCTGTTGACTCAGATTGGCTGCACTTTAAATTTTCC

CATTAGTCCTATTGAGACTGTACCAGTAAAATTAAAGCCAGGAATGGATG

GCCCAAAAGTTAAACAATGGCCATTGACAGAAGAAAAAATAAAAGCATTA

GTAGAAATTTGTACAGAAATGGAAAAGGAAGGAAAAATTTCAAAAATTGG

GCCTGAAAATCCATACAATACTCCAGTATTTGCCATAAAGAAAAAAGACA

GTACTAAATGGAGAAAATTAGTAGATTTCAGAGAACTTAATAAGAGAACT

CAAGATTTCTGGGAAGTTCAATTAGGAATACCACATCCTGCAGGGTTAAA

ACAGAAAAAATCAGTAACAGTACTGGATGTGGGCGATGCATATTTTTCAG

TTCCCTTAGATAAAGACTTCAGGAAGTATACTGCATTTACCATACCTAGT

ATAAACAATGAGACACCAGGGATTAGATATCAGTACAATGTGCTTCCACA

GGGATGGAAAGGATCACCAGCAATATTCCAGTGTAGCATGACAAAAATCT

TAGAGCCTTTTAGAAAACAAAATCCAGACATAGTCATCTATCAATACATG

GATGATTTGTATGTAGGATCTGACTTAGAAATAGGGCAGCATAGAACAAA

AATAGAGGAACTGAGACAACATCTGTTGAGGTGGGGATTTACCACACCAG

ACAAAAAACATCAGAAAGAACCTCCATTCCTTTGGATGGGTTATGAACTC

CATCCTGATAAATGGACAGTACAGCCTATAGTGCTGCCAGAAAAGGACAG

CTGGACTGTCAATGACATACAGAAATTAGTGGGAAAATTGAATTGGGCAA

GTCAGATTTATGCAGGGATTAAAGTAAGGCAATTATGTAAACTTCTTAGG

GGAACCAAAGCACTAACAGAAGTAGTACCACTAACAGAAGAAGCAGAGCT

AGAACTGGCAGAAAACAGGGAGATTCTAAAAGAACCGGTACATGGAGTGT

ATTATGACCCATCAAAAGACTTAATAGCAGAAATACAGAAGCAGGGGCAA

GGCCAATGGACATATCAAATTTATCAAGAGCCATTTAAAAATCTGAAAAC

AGGAAAGTATGCAAGAATGAAGGGTGCCCACACTAATGATGTGAAACAAT

TAACAGAGGCAGTACAAAAAATAGCCACAGAAAGCATAGTAATATGGGGA

AAGACTCCTAAATTTAAATTACCCATACAAAAGGAAACATGGGAAGCATG

GTGGACAGAGTATTGGCAAGCCACCTGGATTCCTGAGTGGGAGTTTGTCA

ATACCCCTCCCTTAGTGAAGTTATGGTACCAGTTAGAGAAAGAACCCATA

ATAGGAGCAGAAACTTTCTATGTAGATGGGGCAGCCAATAGGGAAACTAA

ATTAGGAAAAGCAGGATATGTAACTGACAGAGGAAGACAAAAAGTTGTCC

CCCTAACGGACACAACAAATCAGAAGACTGAGTTACAAGCAATTCATCTA

GCTTTGCAGGATTCGGGATTAGAAGTAAACATAGTGACAGACTCACAATA

TGCATTGGGAATCATTCAAGCACAACCAGATAAGAGTGAATCAGAGTTAG

TCAGTCAAATAATAGAGCAGTTAATAAAAAAGGAAAAAGTCTACCTGGCA

TGGGTACCAGCACACAAAGGAATTGGAGGAAATGAACAAGTAGATAAATT

GGTCAGTGCTGGAATCAGGAAAGTACTATTTTTAGATGGAATAGATAAGG

CCCAAGAAGAACATGAGAAATATCACAGTAATTGGAGAGCAATGGCTAGT

GATTTTAACCTACCACCTGTAGTAGCAAAAGAAATAGTAGCCAGCTGTGA

TAAATGTCAGCTAAAAGGGGAAGCCATGCATGGACAAGTAGACTGTAGCC

CAGGAATATGGCAGCTAGATTGTACACATTTAGAAGGAAAAGTTATCTTG

GTAGCAGTTCATGTAGCCAGTGGATATATAGAAGCAGAAGTAATTCCAGC

AGAGACAGGGCAAGAAACAGCATACTTCCTCTTAAAATTAGCAGGAAGAT

GGCCAGTAAAAACAGTACATACAGACAATGGCAGCAATTTCACCAGTACT

ACAGTTAAGGCCGCCTGTTGGTGGGCGGGGATCAAGCAGGAATTTGGCAT

```
TCCCTACAATCCCCAAAGTCAAGGAGTAATAGAATCTATGAATAAAGAAT
TAAAGAAAATTATAGGACAGGTAAGAGATCAGGCTGAACATCTTAAGACA
GCAGTACAAATGGCAGTATTCATCCACAATTTTAAAAGAAAAGGGGGAT
TGGGGGGTACAGTGCAGGGGAAAGAATAGTAGACATAATAGCAACAGACA
TACAAACTAAAGAATTACAAAAACAAATTACAAAAATTCAAAATTTTCGG
GTTTATTACAGGGACAGCAGAGATCCAGTTTGGAAAGGACCAGCAAAGCT
CCTCTGGAAAGGTGAAGGGGCAGTAGTAATACAAGATAATAGTGACATAA
AAGTAGTGCCAAGAAGAAAAGCAAAGATCATCAGGGATTATGGAAAACAG
ATGGCAGGTGATGATTGTGTGGCAAGTAGACAGGATGAGGATTAA
```

Next, a DNA fragment containing the Rev, RRE, and rabbit beta globin poly A sequence with XbaI and XmaI flanking restriction sites was synthesized by MWG Operon. The DNA fragment was then inserted into the plasmid at the XbaI and XmaI restriction sites The DNA sequence was as follows:

```
                                          (SEQ ID NO: 35)
TCTAGAATGGCAGGAAGAAGCGGAGACAGCGACGAAGAGCTCATCAGAAC
AGTCAGACTCATCAAGCTTCTCTATCAAAGCAACCCACCTCCCAATCCCG
AGGGGACCCGACAGGCCCGAAGGAATAGAAGAAGAAGGTGGAGAGAGAGA
CAGAGACAGATCCATTCGATTAGTGAACGGATCCTTGGCACTTATCTGGG
ACGATCTGCGGAGCCTGTGCCTCTTCAGCTACCACCGCTTGAGAGACTTA
CTCTTGATTGTAACGAGGATTGTGGAACTTCTGGGACGCAGGGGGTGGGA
AGCCCTCAAATATTGGTGGAATCTCCTACAATATTGGAGTCAGGAGCTAA
AGAATAGAGGAGCTTTGTTCCTTGGGTTCTTGGGAGCAGCAGGAAGCACT
ATGGGCGCAGCGTCAATGACGCTGACGGTACAGGCCAGACAATTATTGTC
TGGTATAGTGCAGCAGCAGAACAATTTGCTGAGGGCTATTGAGGCGCAAC
AGCATCTGTTGCAACTCACAGTCTGGGGCATCAAGCAGCTCCAGGCAAGA
ATCCTGGCTGTGGAAAGATACCTAAAGGATCAACAGCTCCTAGATCTTTT
TCCCTCTGCCAAAAATTATGGGGACATCATGAAGCCCCTTGAGCATCTGA
CTTCTGGCTAATAAAGGAAATTTATTTTCATTGCAATAGTGTGTTGGAAT
TTTTTGTGTCTCTCACTCGGAAGGACATATGGGAGGGCAAATCATTTAAA
ACATCAGAATGAGTATTTGGTTTAGAGTTTGGCAACATATGCCATATGCT
GGCTGCCATGAACAAAGGTGGCTATAAAGAGGTCATCAGTATATGAAACA
GCCCCCTGCTGTCCATTCCTTATTCCATAGAAAAGCCTTGACTTGAGGTT
AGATTTTTTTTATATTTTGTTTTGTGTTATTTTTTTCTTTAACATCCCTA
AAATTTTCCTTACATGTTTTACTAGCCAGATTTTTCCTCCTCTCCTGACT
ACTCCCAGTCATAGCTGTCCCTCTTCTCTTATGAAGATCCCTCGACCTGC
AGCCCAAGCTTGGCGTAATCATGGTCATAGCTGTTTCCTGTGTGAAATTG
TTATCCGCTCACAATTCCACACAACATACGAGCCGGAAGCATAAAGTGTA
AAGCCTGGGGTGCCTAATGAGTGAGCTAACTCACATTAATTGCGTTGCGC
TCACTGCCCGCTTTCCAGTCGGGAAACCTGTCGTGCCAGCGGATCCGCAT
CTCAATTAGTCAGCAACCATAGTCCCGCCCCTAACTCCGCCCATCCCGCC
CCTAACTCCGCCCAGTTCCGCCCATTCTCCGCCCCATGGCTGACTAATTT
TTTTTATTTATGCAGAGGCCGAGGCCGCCTCGGCCTCTGAGCTATTCCAG
AAGTAGTGAGGAGGCTTTTTTGGAGGCCTAGGCTTTTGCAAAAAGCTAAC
TTGTTTATTGCAGCTTATAATGGTTACAAATAAAGCAATAGCATCACAAA
TTTCACAAATAAAGCATTTTTTTCACTGCATTCTAGTTGTGGTTTGTCCA
AACTCATCAATGTATCTTATCAGCGGCCGCCCCGGG
```

Finally, the CMV promoter of pCDNA3.1 was replaced with the CAG enhancer/promoter plus a chicken beta actin intron sequence. A DNA fragment containing the CAG enhancer/promoter/intron sequence with MluI and EcoRI flanking restriction sites was synthesized by MWG Operon. The DNA fragment was then inserted into the plasmid at the MluI and EcoRI restriction sites. The DNA sequence was as follows:

```
                                          (SEQ ID NO: 36)
ACGCGTTAGTTATTAATAGTAATCAATTACGGGGTCATTAGTTCATAGCC
CATATATGGAGTTCCGCGTTACATAACTTACGGTAAATGGCCCGCCTGGC
TGACCGCCCAACGACCCCCGCCCATTGACGTCAATAATGACGTATGTTCC
CATAGTAACGCCAATAGGGACTTTCCATTGACGTCAATGGGTGGACTATT
TACGGTAAACTGCCCACTTGGCAGTACATCAAGTGTATCATATGCCAAGT
ACGCCCCCTATTGACGTCAATGACGGTAAATGGCCCGCCTGGCATTATGC
CCAGTACATGACCTTATGGGACTTTCCTACTTGGCAGTACATCTACGTAT
TAGTCATCGCTATTACCATGGTCGAGGTGAGCCCCACGTTCTGCTTCAC
TCTCCCCATCTCCCCCCCCTCCCCACCCCCAATTTTGTATTTATTTATTT
TTTAATTATTTTGTGCAGCGATGGGGGCGGGGGGGGGGGGCGCGCGCC
AGGCGGGGCGGGCGGGCGAGGGCGGGGCGGGGCGAGGCGGAGAGGTG
CGGCGGCAGCCAATCAGAGCGGCGCGCTCCGAAAGTTTCCTTTTATGGCG
AGGCGGCGGCGGCGGCGGCCCTATAAAAAGCGAAGCGCGCGGCGGGCGGG
AGTCGCTGCGTTGCCTTCGCCCCGTGCCCCGCTCCGCGCCGCCTCGCGCC
GCCCGCCCCGGCTCTGACTGACCGCGTTACTCCCACAGGTGAGCGGGCGG
GACGGCCCTTCTCCTCCGGGCTGTAATTAGCGCTTGGTTTAATGACGGCT
CGTTTCTTTTCTGTGGCTGCGTGAAAGCCTTAAAGGGCTCCGGGAGGGCC
CTTTGTGCGGGGGGAGCGGCTCGGGGGGTGCGTGCGTGTGTGTGCGT
GGGGAGCGCCGCGTGCGGCCCGCGCTGCCCGGCGGCTGTGAGCGCTGCGG
GCGCGGCGCGGGCTTTGTGCGCTCCGCGTGTGCGCGAGGGGAGCGCGGC
CGGGGGCGGTGCCCCGCGGTGCGGGGGGCTGCGAGGGGAACAAAGGCTG
CGTGCGGGGTGTGTGCGTGGGGGGGTGAGCAGGGGGTGTGGGCGCGGCGG
TCGGGCTGTAACCCCCCCTGCACCCCCCTCCCCGAGTTGCTGAGCACGG
CCCGGCTTCGGGTGCGGGCTCCGTGCGGGGCGTGGCGCGGGCTCGCCG
TGCCGGGCGGGGGTGGCGGCAGGTGGGGGTGCCGGGCGGGCGGGGCCG
CCTCGGGCCGGGAGGGCTCGGGGAGGGGCGCGGCGGCCCCGGAGCGCC
GGCGGCTGTCGAGGCGCGGCGAGCCGCAGCCATTGCCTTTTATGGTAATC
GTGCGAGAGGGCGCAGGGACTTCCTTTGTCCCAAATCTGGCGGAGCCGAA
```

```
ATCTGGGAGGCGCCGCCGCACCCCCTCTAGCGGGCGCGGGCGAAGCGGTG

CGGCGCCGGCAGGAAGGAAATGGGCGGGGAGGGCCTTCGTCGTCGCCGC

GCCGCCGTCCCCTTCTCCATCTCCAGCCTCGGGGCTGCCGCAGGGGACG

GCTGCCTTCGGGGGGGACGGGGCAGGGCGGGGTTCGGCTTCTGGCGTGTG

ACCGGCGGGAATTC
```

Construction of the VSV-G Envelope Plasmid:

The vesicular stomatitis Indiana virus glycoprotein (VSV-G) sequence was synthesized by MWG Operon with flanking EcoRI restriction sites. The DNA fragment was then inserted into the pCDNA3.1 plasmid (Invitrogen) at the EcoRI restriction site and the correct orientation was determined by sequencing using a CMV specific primer. The DNA sequence was as follows:

```
                                          (SEQ ID NO: 37)
GAATTCATGAAGTGCCTTTTGTACTTAGCCTTTTTATTCATTGGGGTGAA

TTGCAAGTTCACCATAGTTTTTCCACACAACCAAAAAGGAAACTGGAAAA

ATGTTCCTTCTAATTACCATTATTGCCCGTCAAGCTCAGATTTAAATTGG

CATAATGACTTAATAGGCACAGCCTTACAAGTCAAAATGCCCAAGAGTCA

CAAGGCTATTCAAGCAGACGGTTGGATGTGTCATGCTTCCAAATGGGTCA

CTACTTGTGATTTCCGCTGGTATGGACCGAAGTATATAACACATTCCATC

CGATCCTTCACTCCATCTGTAGAACAATGCAAGGAAAGCATTGAACAAAC

GAAACAAGGAACTTGGCTGAATCCAGGCTTCCCTCCTCAAAGTTGTGGAT

ATGCAACTGTGACGGATGCCGAAGCAGTGATTGTCCAGGTGACTCCTCAC

CATGTGCTGGTTGATGAATACACAGGAGAATGGGTTGATTCACAGTTCAT

CAACGGAAAATGCAGCAATTACATATGCCCCACTGTCCATAACTCTACAA

CCTGGCATTCTGACTATAAGGTCAAAGGGCTATGTGATTCTAACCTCATT

TCCATGGACATCACCTTCTTCTCAGAGGACGGAGAGCTATCATCCCTGGG

AAAGGAGGGCACAGGGTTCAGAAGTAACTACTTTGCTTATGAAACTGGAG

GCAAGGCCTGCAAAATGCAATACTGCAAGCATTGGGGAGTCAGACTCCCA

TCAGGTGTCTGGTTCGAGATGGCTGATAAGGATCTCTTTGCTGCAGCCAG

ATTCCCTGAATGCCCAGAAGGGTCAAGTATCTCTGCTCCATCTCAGACCT

CAGTGGATGTAAGTCTAATTCAGGACGTTGAGAGGATCTTGGATTATTCC

CTCTGCCAAGAAACCTGGAGCAAAATCAGAGCGGGTCTTCCAATCTCTCC

AGTGGATCTCAGCTATCTTGCTCCTAAAAACCCAGGAACCGGTCCTGCTT

TCACCATAATCAATGGTACCCTAAAATACTTTGAGACCAGATACATCAGA

GTCGATATTGCTGCTCCAATCCTCTCAAGAATGGTCGGAATGATCAGTGG

AACTACCACAGAAAGGGAACTGTGGGATGACTGGGCACCATATGAAGACG

TGGAAATTGGACCCAATGGAGTTCTGAGGACCAGTTCAGGATATAAGTTT

CCTTTATACATGATTGGACATGGTATGTTGGACTCCGATCTTCATCTTAG

CTCAAAGGCTCAGGTGTTCGAACATCCTCACATTCAAGACGCTGCTTCGC

AACTTCCTGATGATGAGAGTTTATTTTTTGGTGATACTGGGCTATCCAAA

AATCCAATCGAGCTTGTAGAAGGTTGGTTCAGTAGTTGGAAAAGCTCTAT

TGCCTCTTTTTTCTTTATCATAGGGTTAATCATTGGACTATTCTTGGTTC
```

```
                                          -continued
TCCGAGTTGGTATCCATCTTTGCATTAAATTAAAGCACACCAAGAAAAGA

CAGATTTATACAGACATAGAGATGAGAATTC
```

Figure 3:
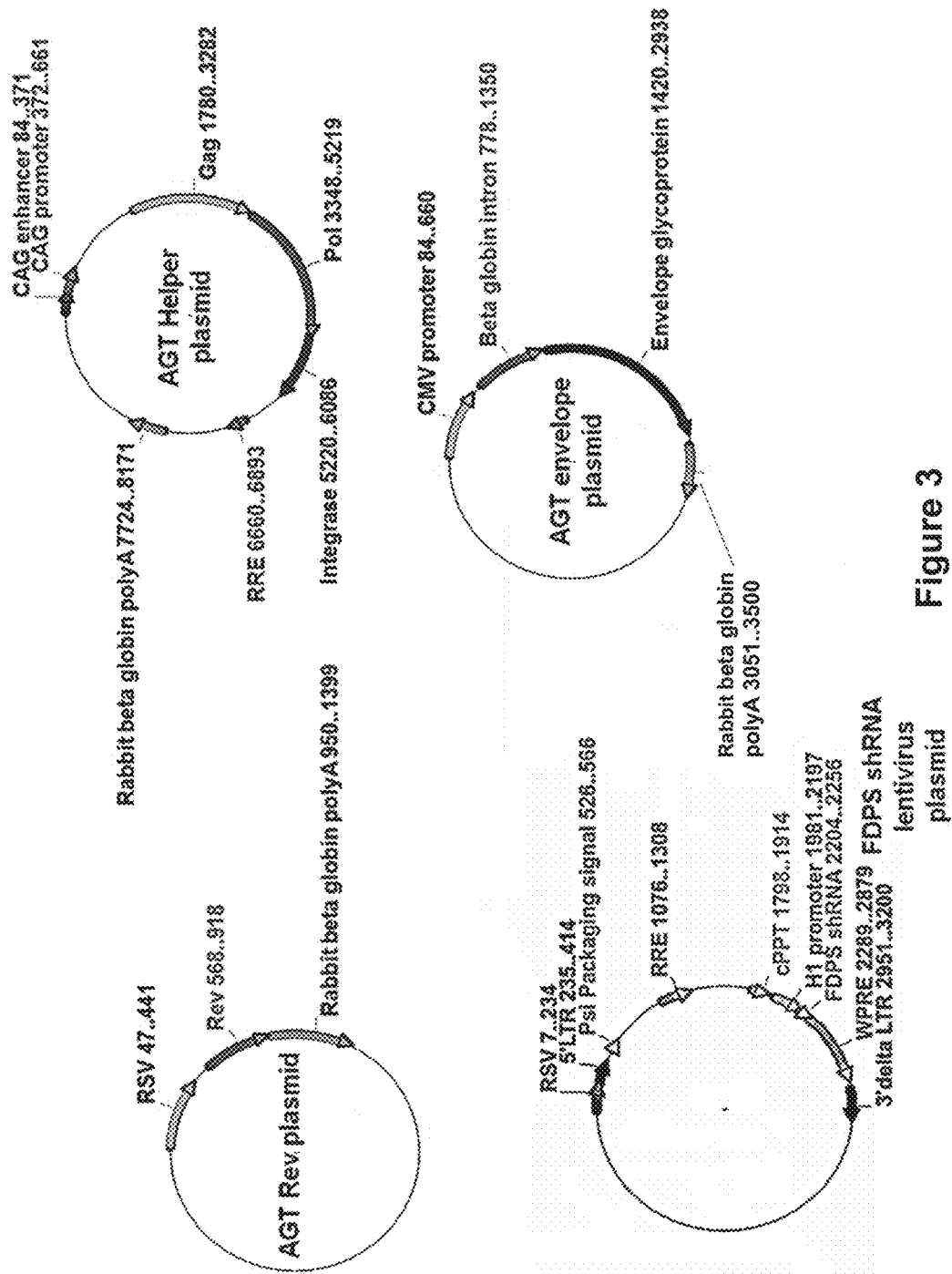
FIG. 3 depicts an exemplary 4-vector lentiviral vector system in a circularized form.

A 4-vector system (i.e., a 3-vector lentiviral packaging system) has also been designed and produced using the methods and materials described herein. A schematic of the 4-vector system is shown in FIG. 3. Briefly, and with reference to FIG. 3, the top-most vector is a helper plasmid, which, in this case, does not include Rev. The vector second from the top is a separate Rev plasmid. The vector second from the bottom is the envelope plasmid. The bottom-most vector is the previously described therapeutic vector.

Referring, in part, to FIG. 2, the Helper plasmid includes a CAG enhancer (SEQ ID NO: 27); a CAG promoter (SEQ ID NO: 19); a chicken beta actin intron (SEQ ID NO: 28); a HIV gag (SEQ ID NO: 20); a HIV Pol (SEQ ID NO: 21); a HIV Int (SEQ ID NO: 22); a HIV RRE (SEQ ID NO: 23); and a rabbit beta globin poly A (SEQ ID NO: 29).

The Rev plasmid includes a RSV promoter (SEQ ID NO: 38); a HIV Rev (SEQ ID NO: 39); and a rabbit beta globin poly A (SEQ ID NO: 29).

The Envelope plasmid includes a CMV promoter (SEQ ID NO: 25); a beta globin intron (SEQ ID NO: 30); a VSV-G (SEQ ID NO: 28); and a rabbit beta globin poly A (SEQ ID NO: 29).

Synthesis of a 3-Vector Lentiviral Packaging System Including Helper, Rev, and Envelope Plasmids.

Materials and Methods:

Construction of the Helper Plasmid without Rev:

The Helper plasmid without Rev was constructed by inserting a DNA fragment containing the RRE and rabbit beta globin poly A sequence. This sequence was synthesized by MWG Operon with flanking XbaI and XmaI restriction sites. The RRE/rabbit poly A beta globin sequence was then inserted into the Helper plasmid at the XbaI and XmaI restriction sites. The DNA sequence is as follows:

```
                                          (SEQ ID NO: 67)
TCTAGAAGGAGCTTTGTTCCTTGGGTTCTTGGGAGCAGCAGGAAGCACTA

TGGGCGCAGCGTCAATGACGCTGACGGTACAGGCCAGACAATTATTGTCT

GGTATAGTGCAGCAGCAGAACAATTTGCTGAGGGCTATTGAGGCGCAACA

GCATCTGTTGCAACTCACAGTCTGGGGCATCAAGCAGCTCCAGGCAAGAA

TCCTGGCTGTGGAAAGATACCTAAAGGATCAACAGCTCCTAGATCTTTTT

CCCTCTGCCAAAAATTATGGGGACATCATGAAGCCCCTTGAGCATCTGAC

TTCTGGCTAATAAAGGAAATTTATTTTCATTGCAATAGTGTGTTGGAATT

TTTTGTGTCTCTCACTCGGAAGGACATATGGGAGGGCAAATCATTTAAAA

CATCAGAATGAGTATTTGGTTTAGAGTTTGGCAACATATGCCATATGCTG

GCTGCCATGAACAAAGGTGGCTATAAAGAGGTCATCAGTATATGAAACAG

CCCCCTGCTGTCCATTCCTTATTCCATAGAAAAGCCTTGACTTGAGGTTA

GATTTTTTTATATTTTGTTTTGTGTTATTTTTTCTTTAACATCCCTAA

AATTTTCCTTACATGTTTTACTAGCCAGATTTTTCCTCCTCTCCTGACTA

CTCCCAGTCATAGCTGTCCCTCTTCTCTTATGAAGATCCCTCGACCTGCA

GCCCAAGCTTGGCGTAATCATGGTCATAGCTGTTTCCTGTGTGAAATTGT

TATCCGCTCACAATTCCACACAACATACGAGCCGGAAGCATAAAGTGTAA
```

-continued

```
AGCCTGGGGTGCCTAATGAGTGAGCTAACTCACATTAATTGCGTTGCGCT

CACTGCCCGCTTTCCAGTCGGGAAACCTGTCGTGCCAGCGGATCCGCATC

TCAATTAGTCAGCAACCATAGTCCCGCCCCTAACTCCGCCCATCCCGCCC

CTAACTCCGCCCAGTTCCGCCCATTCTCCGCCCCATGGCTGACTAATTTT

TTTTATTTATGCAGAGGCCGAGGCCGCCTCGGCCTCTGAGCTATTCCAGA

AGTAGTGAGGAGGCTTTTTTGGAGGCCTAGGCTTTTGCAAAAAGCTAACT

TGTTTATTGCAGCTTATAATGGTTACAAATAAAGCAATAGCATCACAAAT

TTCACAAATAAAGCATTTTTTTCACTGCATTCTAGTTGTGGTTTGTCCAA

ACTCATCAATGTATCTTATCACCCGGG
```

Construction of the Rev Plasmid:

The RSV promoter and HIV Rev sequence was synthesized as a single DNA fragment by MWG Operon with flanking MfeI and XbaI restriction sites. The DNA fragment was then inserted into the pCDNA3.1 plasmid (Invitrogen) at the MfeI and XbaI restriction sites in which the CMV promoter is replaced with the RSV promoter. The DNA sequence was as follows:

```
                                       (SEQ ID NO: 40)
CAATTGCGATGTACGGGCCAGATATACGCGTATCTGAGGGGACTAGGGTG

TGTTTAGGCGAAAAGCGGGGCTTCGGTTGTACGCGGTTAGGAGTCCCCTC

AGGATATAGTAGTTTCGCTTTTGCATAGGGAGGGGGAAATGTAGTCTTAT

GCAATACACTTGTAGTCTTGCAACATGGTAACGATGAGTTAGCAACATGC

CTTACAAGGAGAGAAAAAGCACCGTGCATGCCGATTGGTGGAAGTAAGGT

GGTACGATCGTGCCTTATTAGGAAGGCAACAGACAGGTCTGACATGGATT

GGACGAACCACTGAATTCCGCATTGCAGAGATAATTGTATTTAAGTGCCT

AGCTCGATACAATAAACGCCATTTGACCATTCACCACATTGGTGTGCACC

TCCAAGCTCGAGCTCGTTTAGTGAACCGTCAGATCGCCTGGACGCCAT

CCACGCTGTTTTGACCTCCATAGAAGACACCGGGACCGATCCAGCCTCCC

CTCGAAGCTAGCGATTAGGCATCTCCTATGGCAGGAAGAAGCGGAGACAG

CGACGAAGAACTCCTCAAGGCAGTCAGACTCATCAAGTTTCTCTATCAAA

GCAACCCACCTCCCAATCCCGAGGGGACCCGACAGGCCCGAAGGAATAGA

AGAAGAAGGTGGAGAGAGAGACAGAGACAGATCCATTCGATTAGTGAACG

GATCCTTAGCACTTATCTGGGACGATCTGCGGAGCCTGTGCCTCTTCAGC

TACCACCGCTTGAGAGACTTACTCTTGATTGTAACGAGGATTGTGGAACT

TCTGGGACGCAGGGGGTGGGAAGCCCTCAAATATTGGTGGAATCTCCTAC

AATATTGGAGTCAGGAGCTAAAGAATAGTCTAGA
```

The plasmids for the 2-vector and 3-vector packaging systems could be modified with similar elements and the intron sequences could potentially be removed without loss of vector function. For example, the following elements could replace similar elements in the 2-vector and 3-vector packaging system:

Promoters: Elongation Factor-1 (EF-1) (SEQ ID NO: 41), phosphoglycerate kinase (PGK) (SEQ ID NO: 42), and ubiquitin C (UbC) (SEQ ID NO: 43) can replace the CMV (SEQ ID NO: 25) or CAG promoter (SEQ ID NO: 19). These sequences can also be further varied by addition, substitution, deletion or mutation.

Poly A sequences: SV40 poly A (SEQ ID NO: 44) and bGH poly A (SEQ ID NO: 45) can replace the rabbit beta globin poly A (SEQ ID NO: 29). These sequences can also be further varied by addition, substitution, deletion or mutation.

HIV Gag, Pol, and Integrase sequences: The HIV sequences in the Helper plasmid can be constructed from different HIV strains or clades. For example, HIV Gag (SEQ ID NO: 20); HIV Pol (SEQ ID NO: 21); and HIV Int (SEQ ID NO: 22) from the Bal strain can be interchanged with the gag, pol, and int sequences contained in the helper/helper plus Rev plasmids as outlined herein. These sequences can also be further varied by addition, substitution, deletion or mutation.

Envelope: The VSV-G glycoprotein can be substituted with membrane glycoproteins from feline endogenous virus (RD114) (SEQ ID NO: 46), gibbon ape leukemia virus (GALV) (SEQ ID NO: 47), Rabies (FUG) (SEQ ID NO: 48), lymphocytic choriomeningitis virus (LCMV) (SEQ ID NO: 49), influenza A fowl plague virus (FPV) (SEQ ID NO: 50), Ross River alphavirus (RRV) (SEQ ID NO: 51), murine leukemia virus 10A1 (MLV) (SEQ ID NO: 52), or Ebola virus (EboV) (SEQ ID NO: 53). Sequences for these envelopes are identified in the sequence portion herein. Further, these sequences can also be further varied by addition, substitution, deletion or mutation.

In summary, the 3-vector versus 4-vector systems can be compared and contrasted, in part, as follows. The 3-vector lentiviral vector system contains: 1. Helper plasmid: HIV Gag, Pol, Integrase, and Rev/Tat; 2. Envelope plasmid: VSV-G/FUG envelope; and 3. Therapeutic vector: RSV 5'LTR, Psi Packaging Signal, Gag fragment, RRE, Env fragment, cPPT, WPRE, and 3'δ LTR. The 4-vector lentiviral vector system contains: 1. Helper plasmid: HIV Gag, Pol, and Integrase; 2. Rev plasmid: Rev; 3. Envelope plasmid: VSV-G/FUG envelope; and 4. Therapeutic vector: RSV 5'LTR, Psi Packaging Signal, Gag fragment, RRE, Env fragment, cPPT, WPRE, and 3'delta LTR. Sequences corresponding with the above elements are identified in the sequence listings portion herein.

Example 2: Development of a Lentiviral Vector that Expresses FDPS

The purpose of this Example was to develop an FDPS lentivirus vector.

Inhibitory RNA Design:

The sequence of *Homo sapiens* Farnesyl diphosphate synthase (FDPS) (NM_002004.3) mRNA was used to search for potential siRNA or shRNA candidates to knockdown FDPS levels in human cells. Potential RNA interference sequences were chosen from candidates selected by siRNA or shRNA design programs such as from GPP Web Portal hosted by the Broad Institute (http://portals.broadinstitute-.org/gpp/public/) or the BLOCK-iT RNAi Designer from Thermo Scientific (https://maidesigner.thermofisher.com/maiexpress/). Individual selected shRNA sequences were inserted into a lentiviral vector immediately 3 prime to a RNA polymerase III promoter such as H1 (SEQ ID NO: 16), U6 (SEQ ID NO: 54), or 7SK (SEQ ID NO: 55) to regulate shRNA expression. These lentivirus shRNA constructs were used to transduce cells and measure the change in specific mRNA levels. The shRNA most potent for reducing mRNA levels were embedded individually within a microRNA backbone to allow for expression by either the EF-1alpha or CMV RNA polymerase II promoters. The microRNA backbone was selected from mirbase.org. RNA sequences were also synthesized as synthetic siRNA oligonucleotides and introduced directly into cells without using a lentiviral vector.

Vector Construction:

For FDPS shRNA, oligonucleotide sequences containing BamHI and EcoRI restriction sites were synthesized by Eurofins MWG Operon. Overlapping sense and antisense oligonucleotide sequences were mixed and annealed during cooling from 70 degrees Celsius to room temperature. The lentiviral vector was digested with the restriction enzymes BamHI and EcoRI for one hour at 37 degrees Celsius. The digested lentiviral vector was purified by agarose gel electrophoresis and extracted from the gel using a DNA gel extraction kit from Thermo Scientific. The DNA concentrations were determined and vector to oligo (3:1 ratio) were mixed, allowed to anneal, and ligated. The ligation reaction was performed with T4 DNA ligase for 30 minutes at room temperature. 2.5 microliters of the ligation mix were added to 25 microliters of STBL3 competent bacterial cells. Transformation was achieved after heat-shock at 42 degrees Celsius. Bacterial cells were spread on agar plates containing ampicillin and drug-resistant colonies (indicating the presence of ampicillin-resistance plasmids) were recovered and expanded in LB broth. To check for insertion of the oligo sequences, plasmid DNA was extracted from harvested bacteria cultures with the Thermo Scientific DNA mini prep kit. Insertion of shRNA sequences in the lentiviral vector was verified by DNA sequencing using a specific primer for the promoter used to regulate shRNA expression. Using the following target sequences, exemplary shRNA sequences were determined to knock-down FDPS:

```
            (FDPS target sequence #1; SEQ ID NO: 56)
GTCCTGGAGTACAATGCCATT;

(FDPS shRNA sequence #1; SEQ ID NO: 1)
GTCCTGGAGTACAATGCCATTCTCGAGAATGGCATTGTACTCCAGGACTT

TTT;

(FDPS target sequence #2; SEQ ID NO: 57)
GCAGGATTTCGTTCAGCACTT;

(FDPS shRNA sequence #2; SEQ ID NO: 2)
GCAGGATTTCGTTCAGCACTTCTCGAGAAGTGCTGAACGAAATCCTGCTT

TTT;

(FDPS target sequence #3; SEQ ID NO: 58)
GCCATGTACATGGCAGGAATT;

(FDPS shRNA sequence #3; SEQ ID NO: 3)
GCCATGTACATGGCAGGAATTCTCGAGAATTCCTGCCATGTACATGGCTT

TTT;

(FDPS target sequence #4; SEQ ID NO: 59)
GCAGAAGGAGGCTGAGAAAGT;
and (FDPS shRNA sequence #4; SEQ ID NO: 4)
GCAGAAGGAGGCTGAGAAAGTCTCGAGACTTTCTCAGCCTCCTTCTGCTT

TTT.
``` shRNA sequences were then assembled into a synthetic microRNA (miR) under control of the EF-1 alpha promoter. Briefly, a miR hairpin sequences, such as miR30, miR21, or miR185 as detailed below, was obtained from mirbase.org. The 19-22mer shRNA target sequence was used to construct the synthetic miR sequence. The miR sequence was arranged as an anti-sense-target-sequence-hairpin loop sequence (specific for each microRNA)-sense target sequence.

The following miR sequences were developed:

```
                (miR30 FDPS sequence #1; SEQ ID NO: 5)
AAGGTATATTGCTGTTGACAGTGAGCGACACTTTCTCAGCCTCCTTCTGC

GTGAAGCCACAGATGGCAGAAGGAGGCTGAGAAAGTGCTGCCTACTGCCT

CGGACTTCAAGGGGCT (miR30 FDPS sequence #2; SEQ ID NO: 6)
AAGGTATATTGCTGTTGACAGTGAGCGACACTTTCTCAGCCTCCTTCTGC

GTGAAGCCACAGATGGCAGAAGGGCTGAGAAAGTGCTGCCTACTGCCTCG

GACTTCAAGGGGCT (miR30 FDPS sequence #3; SEQ ID NO: 7)
TGCTGTTGACAGTGAGCGACTTTCTCAGCCTCCTTCTGCGTGAAGCCACA

GATGGCAGAAGGAGGCTGAGAAAGTTGCCTACTGCCTCGGA (miR155 FDPS sequence #1; SEQ ID NO: 8)
CCTGGAGGCTTGCTGAAGGCTGTATGCTGACTTTCTCAGCCTCCTTCTGC

TTTTGGCCACTGACTGAGCAGAAGGGCTGAGAAAGTCAGGACACAAGGCC

TGTTACTAGCACTCA (miR21 FDPS sequence #1; SEQ ID NO: 9)
CATCTCCATGGCTGTACCACCTTGTCGGGACTTTCTCAGCCTCCTTCTGC

CTGTTGAATCTCATGGCAGAAGGAGGCGAGAAAGTCTGACATTTTGGTAT

CTTTCATCTGACCA (miR185 FDPS sequence #1; SEQ ID NO: 10)
GGGCCTGGCTCGAGCAGGGGGCGAGGGATACTTTCTCAGCCTCCTTCTGC

TGGTCCCCTCCCCGCAGAAGGAGGCTGAGAAAGTCCTTCCCTCCCAATGA

CCGCGTCTTCGTCG
```

Example 3—Knock-Down of FDPS for 3 Days in THP1 Monocytic Leukemia by shRNA #4

Figure 5:
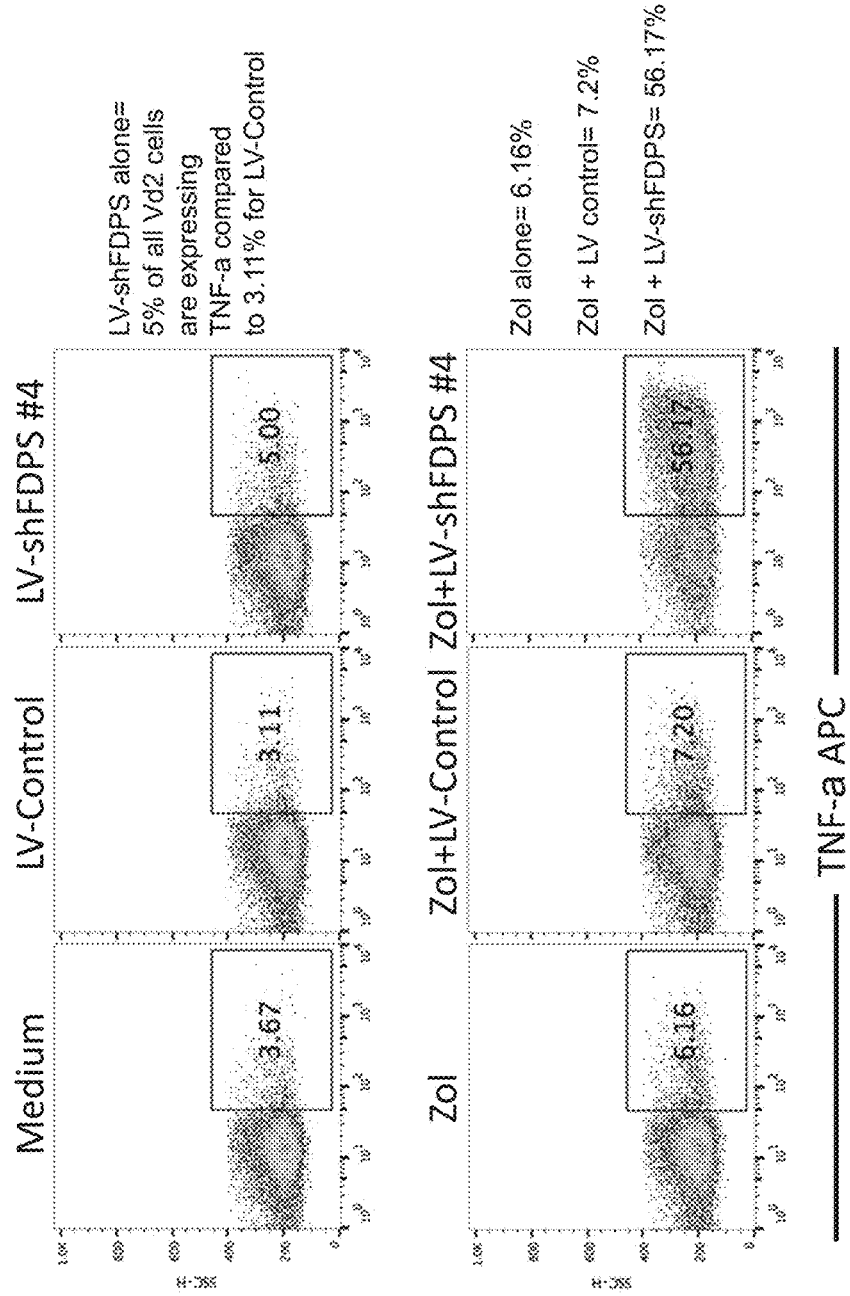
FIG. 5 depicts data demonstrating activation of Vδ2+ T cells THP-1 leukemia cells with a lentivirus expressing FDPS shRNA #4 (SEQ ID NO: 4), as described herein.

This Example illustrates that knock-down of FDPS in THP1 monocytic leukemia cells by lentiviral (LV)-expressing FDPS shRNA #4 stimulates TNF-α expression in gamma delta T cells, as shown in FIG. 5.

THP1 cells (1×10$^5$ cells) were transduced with LV-control or LV-FDPS shRNA #4 for 3 days. Two days after transduction, cells were treated with or without 1 μM zoledronic acid. After 24 hours, the transduced THP-1 cells were co-cultured with 5×10$^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 3.1% of TNF-α expressing Vγ9Vδ2 T cells and LV-FDPS shRNA #4 stimulated 5%. With zoledronic acid treatment, LV-control stimulated 7.2% of TNF-α expressing Vγ9Vδ2 T cells and LV-FDPS shRNA #4 stimulated 56.2%.

Example 4—Knock-Down of FDPS for 14 Days in THP1 Leukemia Cells by shRNA #4

Figure 6:
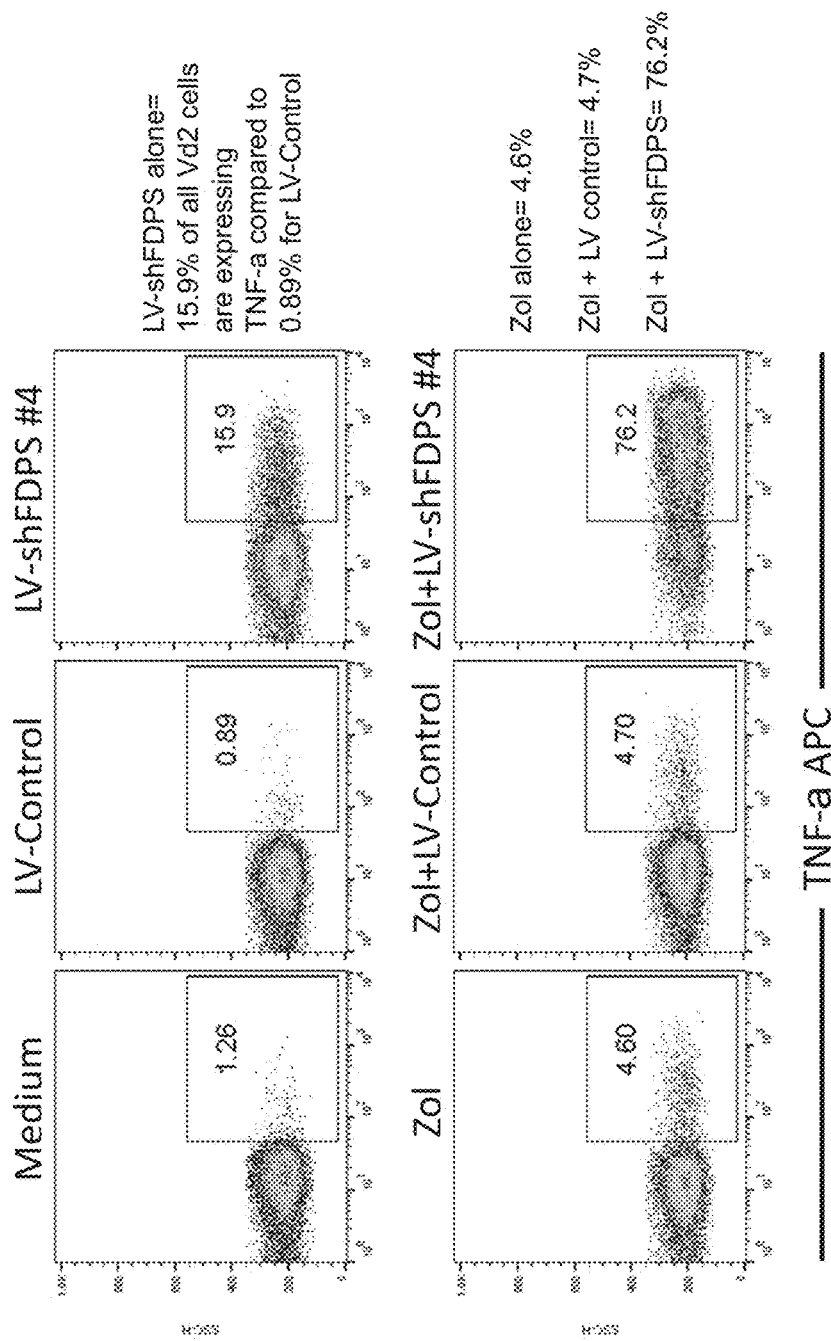
FIG. 6 depicts data demonstrating activation of Vδ2+ T cells by THP-1 leukemia cells with a lentivirus expressing FDPS shRNA #4 (SEQ ID NO: 4), as described herein.

This Example illustrates that Knock-down of FDPS for 14 days in THP1 leukemia cells by lentiviral (LV)-expressing FDPS shRNA #4 stimulates TNF-α expression in GD T cells, as shown in FIG. 6.

THP1 cells ($1\times10^5$ cells) were transduced with LV-control or LV-FDPS shRNA #4 for 14 days. Two days after transduction, cells were treated with or without 1 uM zoledronic acid. After 24 hours, the transduced THP-1 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 0.9% of TNF-α expressing Vγ9Vδ2 T cells and LV-FDPS shRNA #4 (SEQ ID NO: 4) stimulated 15.9%. With zoledronic acid treatment, LV-control stimulated 4.7% of TNF-α expressing Vγ9Vδ2 T cells and LV-FDPS shRNA #4 (SEQ ID NO: 4) stimulated 76.2%.

Example 5—Knock-Down of FDPS for 3 Days in PC3 Prostate Carcinoma Cells by shRNA #1

Figure 7:
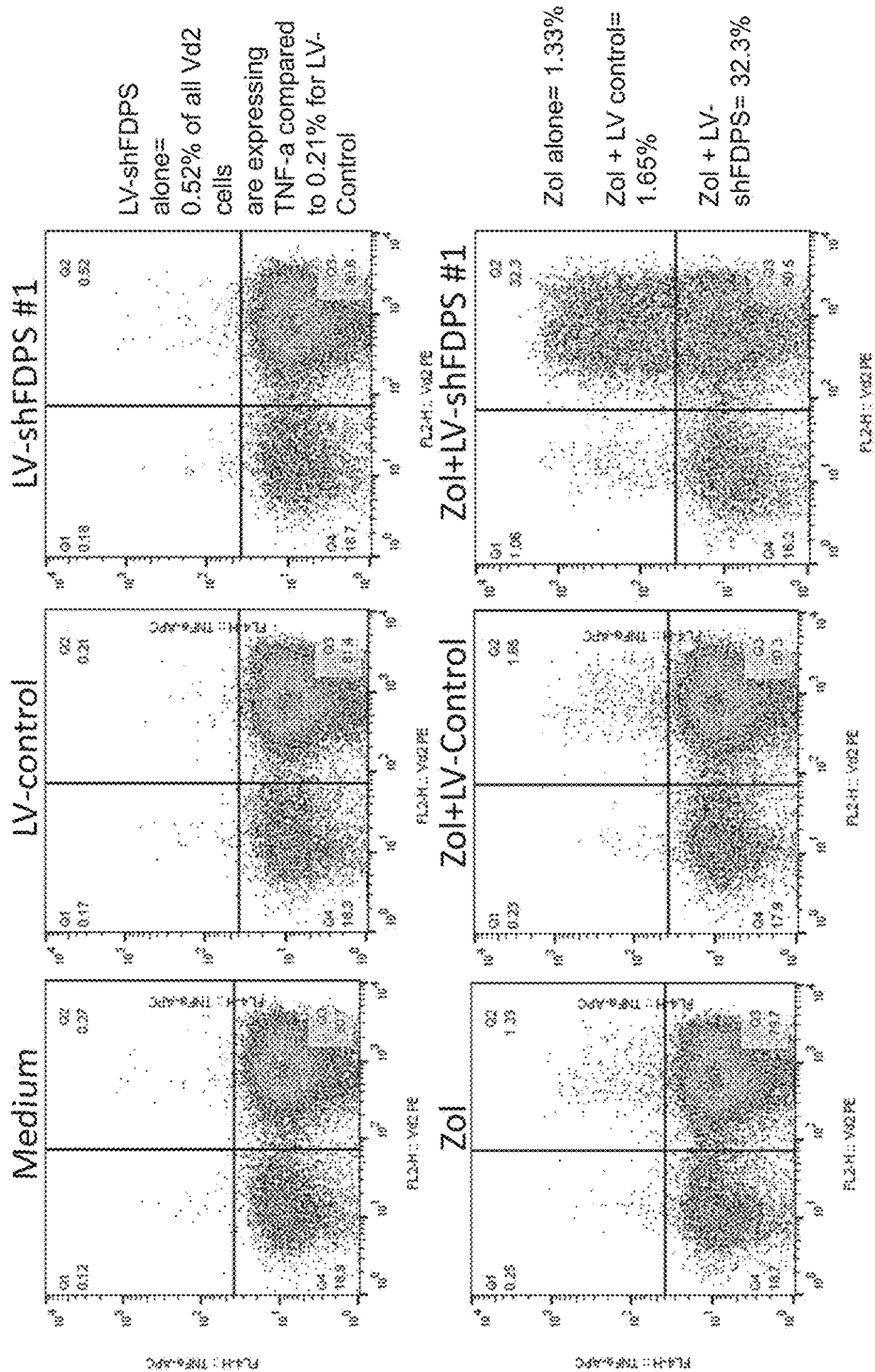
FIG. 7 depicts data demonstrating activation of Vδ2+ T cells by PC3 prostate carcinoma cells with a lentivirus expressing FDPS shRNA #1 (SEQ ID NO: 1), as described herein.

This Example illustrates that knock-down of FDPS for 3 days in PC3 prostate carcinoma cells by lentiviral (LV)-expressing FDPS shRNA #1 stimulates TNF-α expression in GD T cells, as shown in FIG. 7.

PC3 cells were transduced with LV-control or LV-FDPS shRNA #1 (SEQ ID NO: 1) for 3 days. Two days after transduction, cells were treated with or without 1 uM zoledronic acid. After 24 hours, the transduced PC3 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 0.2% of TNF-α expressing Vγ9Vδ2 T cells and LV-FDPS shRNA #1 stimulated 0.5%. With zoledronic acid treatment, LV-control stimulated 1.7% of TNF-α expressing Vγ9Vδ2 T cells and LV-FDPS shRNA #1 (SEQ ID NO: 1) stimulated 32.2%.

Example 6—Knock-Down of FDPS for 3 Days in PC3 Prostate Carcinoma Cells by shRNA #4

Figure 8:
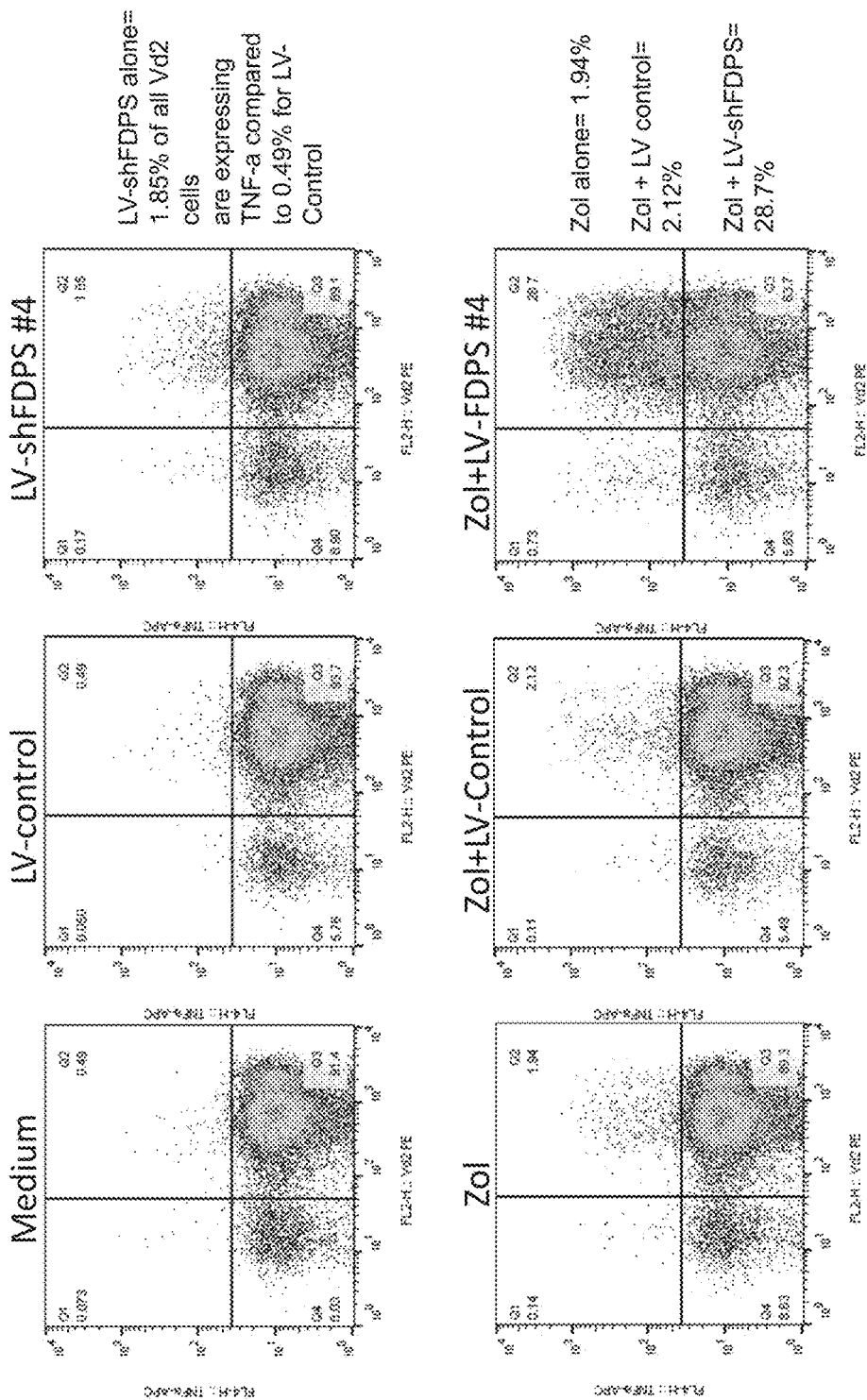
FIG. 8 depicts data demonstrating activation of Vδ2+ T cells by PC3 prostate carcinoma cells with a lentivirus expressing FDPS shRNA #4 (SEQ ID NO: 4), as described herein.

This Example illustrates that Knock-down of FDPS for 3 days in PC3 prostate carcinoma cells by lentiviral (LV)-expressing FDPS shRNA #4 stimulates TNF-α expression in GD T cells, as shown in FIG. 8.

PC3 cells were transduced with LV-control or LV-FDPS shRNA #4 (SEQ ID NO: 4) for 3 days. Two days after transduction, cells were treated with or without 1 uM zoledronic acid. After 24 hours, the transduced PC3 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 0.5% of TNF-α expressing Vγ9Vδ2 T cells and LV-FDPS shRNA #4 (SEQ ID NO: 4) stimulated 1.9%. With zoledronic acid treatment, LV-control stimulated 2.1% of TNF-α expressing Vγ9Vδ2 T cells and LV-FDPS shRNA #4 stimulated 28.7%.

Example 7—Knock-Down of FDPS for 3 Days in HepG2 Liver Carcinoma Cells by shRNA #1 and #4

Figure 9:
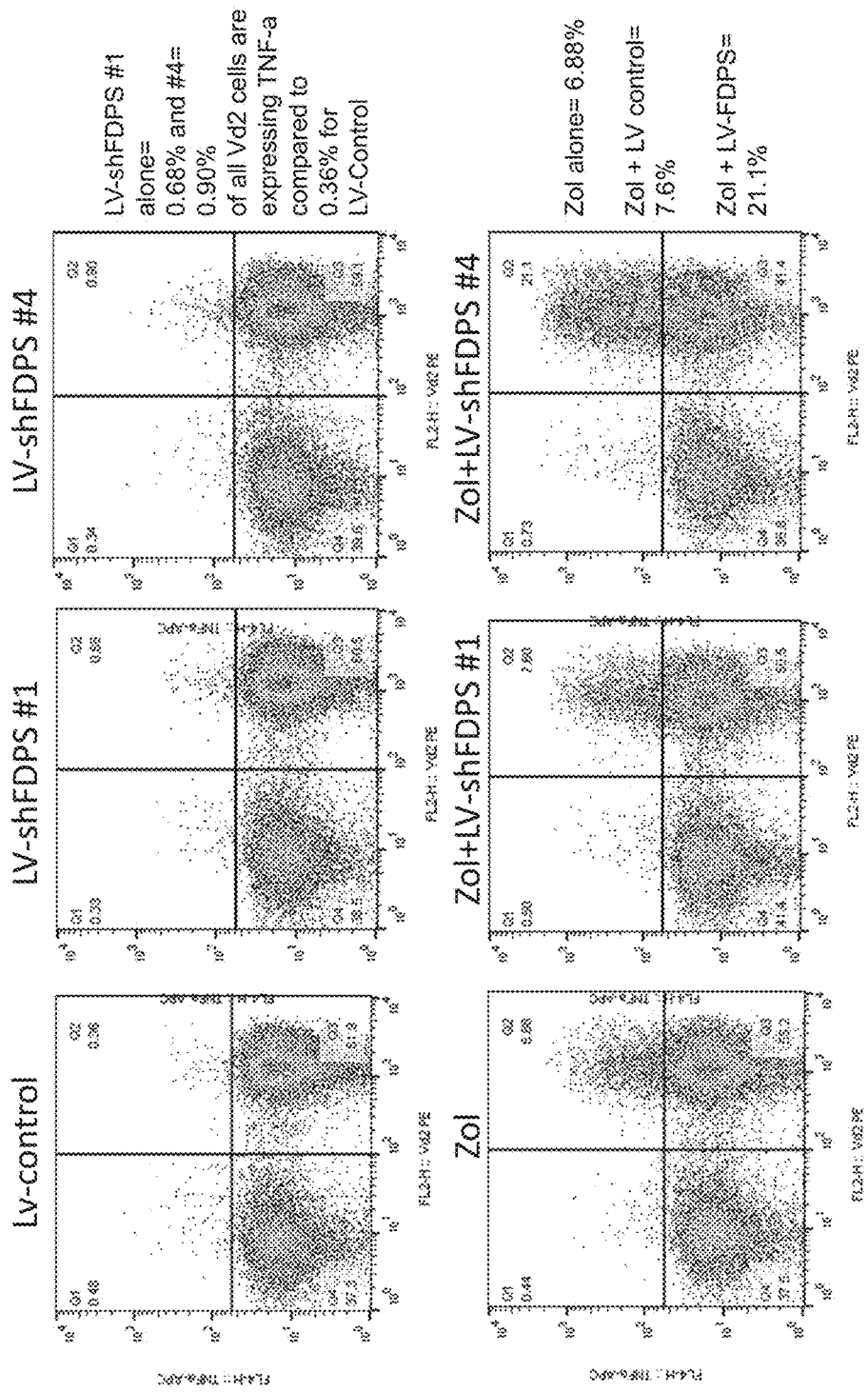
FIG. 9 depicts data demonstrating activation of Vδ2+ T cells by HepG2 carcinoma cells with a lentivirus expressing FDPS shRNA #1 (SEQ ID NO: 1) or FDPS shRNA #4 (SEQ ID NO: 4), as described herein.

This Example illustrates that Knock-down of FDPS for 3 days in HepG2 liver carcinoma cells by lentiviral (LV)-expressing FDPS shRNA #1 (SEQ ID NO: 1) and shRNA#4 (SEQ ID NO: 4) stimulates TNF-α expression in GD T cells, as shown in FIG. 9.

HepG2 cells were transduced with LV-control, LV-FDPS shRNA #1 (SEQ ID NO: 1), or LV-FDPS shRNA #4 (SEQ ID NO: 4) for 3 days. Two days after transduction, cells were treated with or without 1 uM zoledronic acid. After 24 hours, the transduced HepG2 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 0.4% of TNF-α expressing Vγ9Vδ2 T cells and LV-FDPS shRNA #1 (SEQ ID NO: 1) and #4 (SEQ ID NO: 4) stimulated 0.7% and 0.9%, respectively. With zoledronic acid treatment, LV-control stimulated 6.9% of TNF-α expressing Vγ9Vδ2 T cells and LV-FDPS shRNA #1 and #4 stimulated 7.6% and 21.1%, respectively.

Example 8—Knock-Down of FDPS for 3 Days in THP1 Leukemia by microRNA-30

Figure 10:
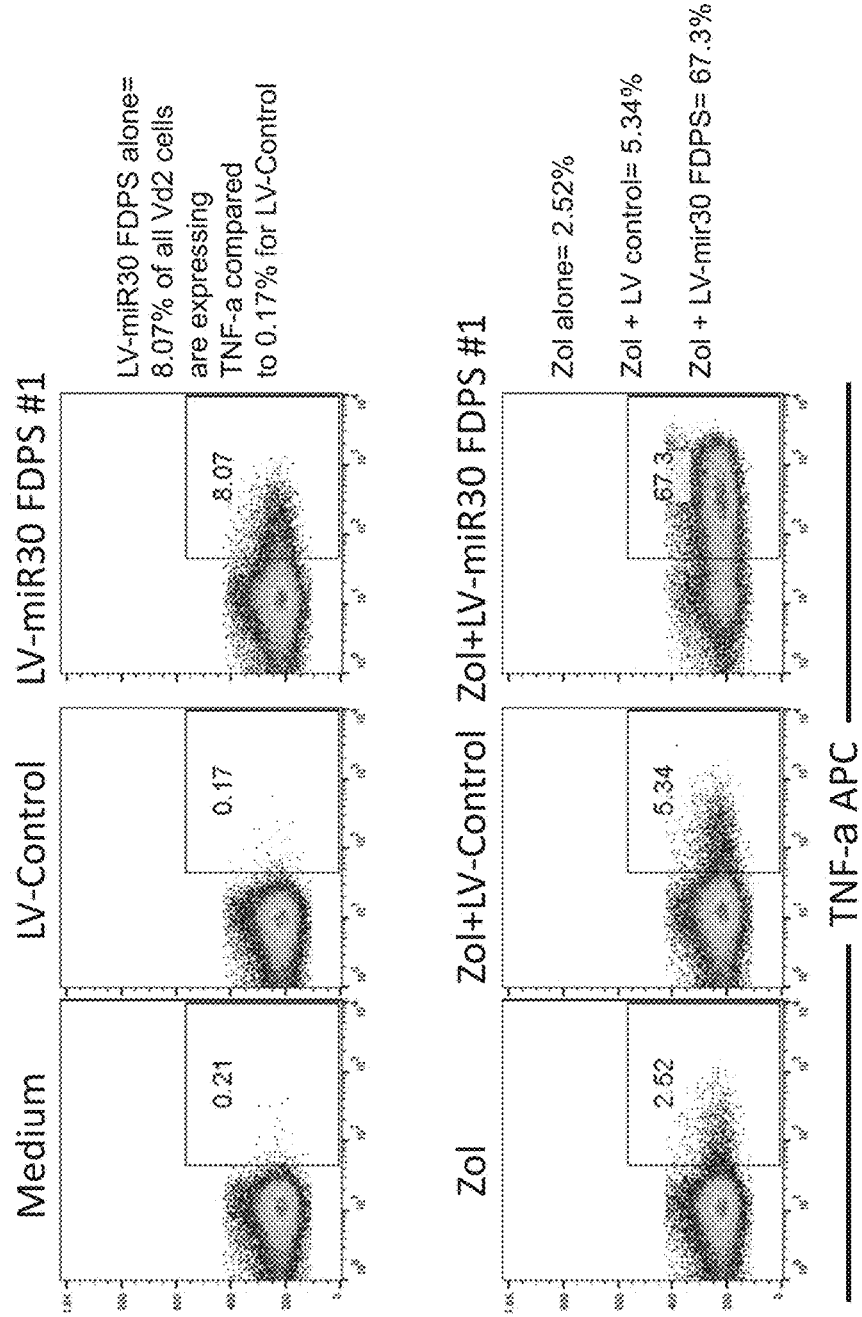
FIG. 10 depicts data demonstrating activation of Vδ2+ T cells by THP-1 leukemia cells with a lentivirus expressing miR30 FDPS #1 (SEQ ID NO: 5), as described herein.

This Example illustrates that Knock-down of FDPS for 3 days in THP1 leukemia cells by lentiviral (LV)-expressing FDPS-targeted synthetic microRNA-30 stimulates TNF-α expression in gamma delta T cells, as shown in FIG. 10.

THP1 cells ($1\times10^5$ cells) were transduced with LV-control or LV-miR30 FDPS #1 (SEQ ID NO: 5) for 3 days. Two days after transduction, cells were treated with or without 1 uM zoledronic acid. After 24 hours, the transduced THP-1 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 0.2% of TNF-α expressing Vγ9Vδ2 T cells and LV-miR30 FDPS stimulated 8.1%. With zoledronic acid treatment, LV-control stimulated 5.3% of TNF-α expressing Vγ9Vδ2 T cells and LV-miR30 FDPS #1 (SEQ ID NO: 5) stimulated 67.3%.

Example 9: E:T Ratios Resulting from Mixture of THP-1 Cells, Cultured Human GD T Cells, and/or Zometa (Zol)

Figure 11:
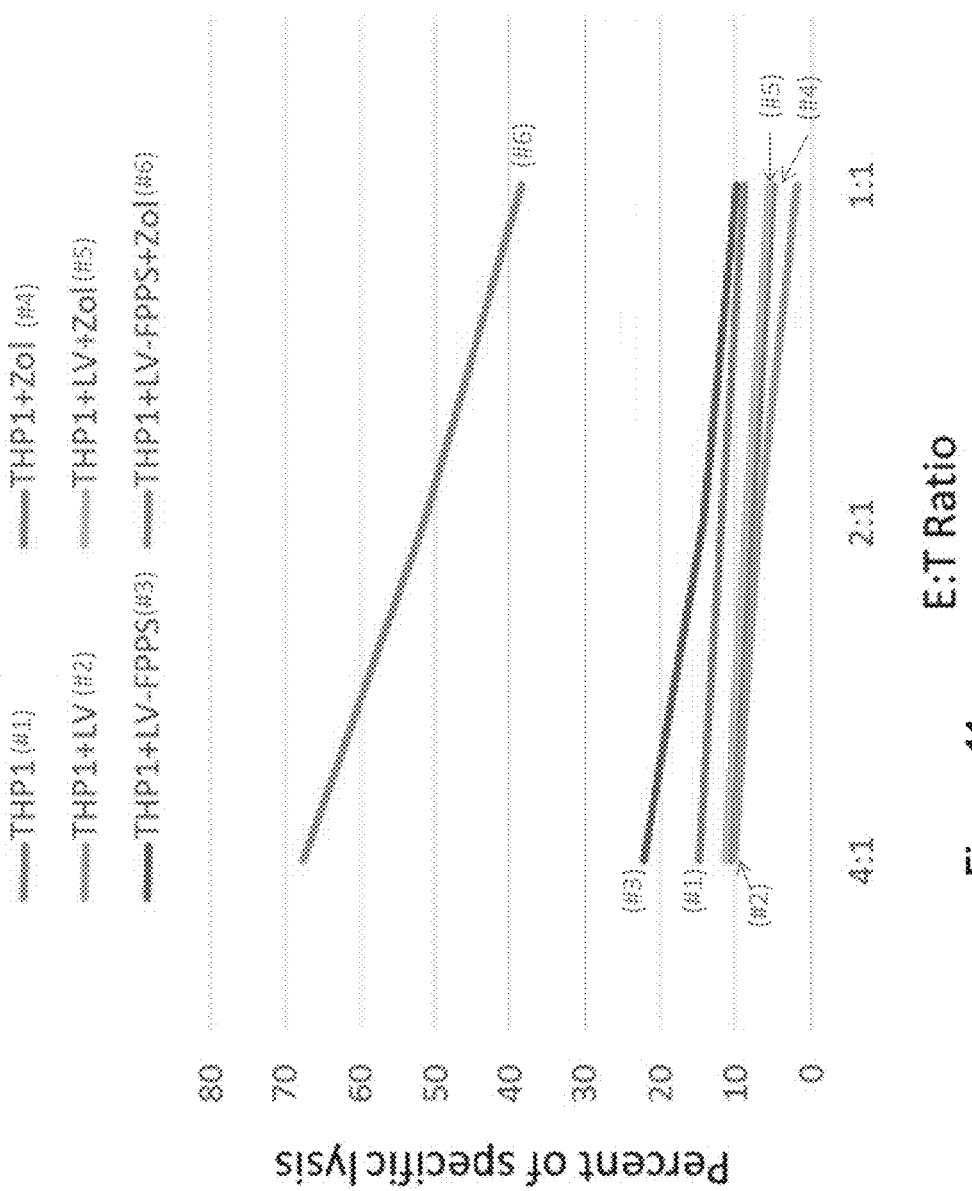
FIG. 11 depicts data demonstrating the percent of specific lysis versus an E:T ratio for a variety of experimental conditions, as described herein.

This Example demonstrates results from mixing treated THP-1 monocytoid tumor cells with cultured human GD T cells, as shown in FIG. 11.

The monocytoid cell line THP-1 was treated with control lentivirus vector (LV), LV suppressing farnesyl diphosphate synthase gene expression (LV-FDPS), zoledronic acid (Zol) or combinations. The legend, as shown in FIG. 11, was: lentiviral control vectors (LV-Control), lentiviral vectors expressing microRNA to down regulate FDPS (LV-FPPS), Zometa (Zol), Zometa plus lentiviral control (Zol+LV-Control), or Zometa plus lentiviral vectors expressing microRNA to down regulate FPPS (Zol+LV-FPPS).

Human GD T cells were cultured from an anonymous donor and added to treated THP-1 cells in 4:1. 2:1 or 1:1 ratios (GD T:THP-1) for 4 hours. Cell killing was measured by a fluorescence assay. When THP-1 cells were treated with a combination of LV-FDPS and Zol, cytotoxic T cell killing by GD T cells was increased greatly compared to either treatment alone. When LV-FDPS treatment alone was compared to Zol treatment alone, the LV-FDPS lead to greater killing but was >3-fold below tumor cell killing after combination treatment. The combined LV-FDPS plus Zol treatment caused nearly 70% tumor cell killing with 4:1 ratio; this was more than 3-fold higher than the second best treatment (LV-FDPS alone).

Figure 12:
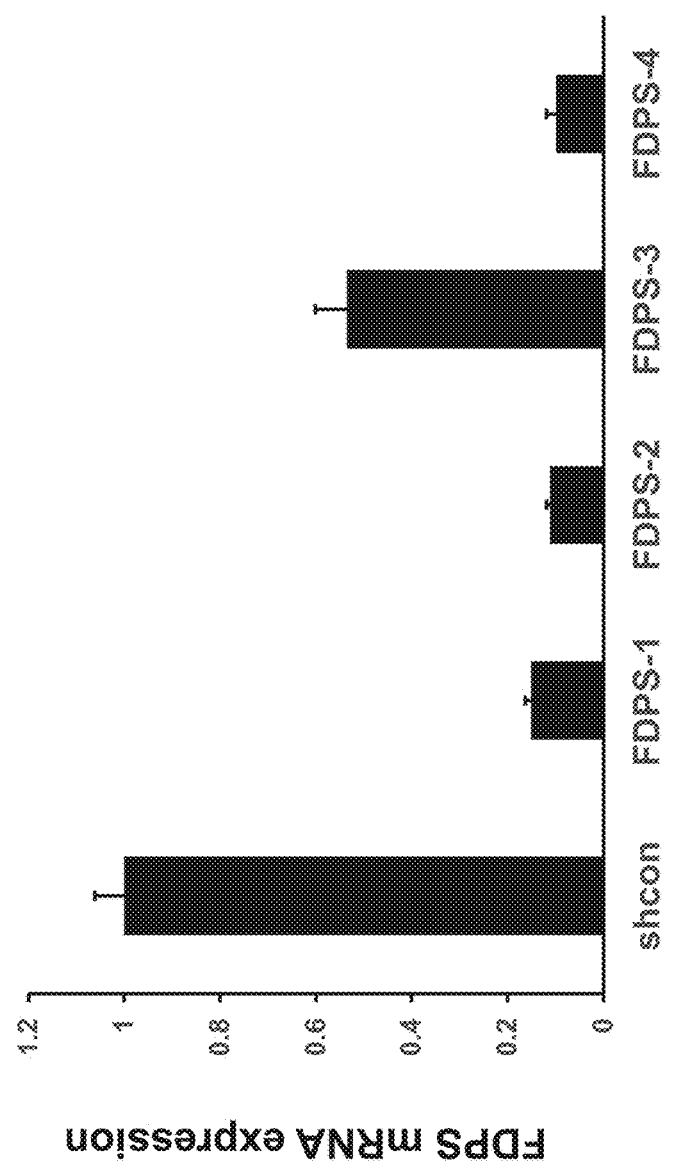
FIG. 12 depicts data demonstrating lentiviral-delivered shRNA-based RNA interference targeting the human FDPS gene.

Example 10—Lentiviral-Delivered shRNA-Based RNA Interference Targeting the Human Farnesyl Diphosphate Synthase (FDPS) Gene HepG2 human hepatocellular carcinoma cells were infected with lentiviral vectors containing the H1 promoter and either a non-targeting or four different FDPS shRNA sequences, as shown in FIG. 12. After 48 hours, RNA was extracted from the cells and converted to cDNA. Expression of FDPS cDNA was determined by quantitative PCR using SYBR Green and FDPS primers. FDPS expression was normalized to actin levels for each sample.
FDPS-targeting lentiviral vectors containing the H1 promoter and either a non-targeting sequence (5'-GCCGCTTT-GTAGGATAGAGCTCGAGCTCTATCCTACAAAGCG-GCTTTTT-3') (SEQ ID NO: 60) or one of four different FDPS shRNA sequences GTCCTGGAGTACAATGCCATTCTCGAGAATGGCAT-TGTACTCCAGGACTTTTT (FDPS shRNA sequence #1; SEQ ID NO: 1); GCAGGATTTCGTTCAGCACTTCTCGAGAAGTGCT-GAACGAAATCCTGCTTTTT (FDPS shRNA sequence #2; SEQ ID NO: 2); GCCATGTACATGGCAGGAATTCTCGAGAATTCCT-GCCATGTACATGGCTTTTT (FDPS shRNA sequence #3; SEQ ID NO: 3); and GCAGAAGGAGGCTGAGAAAGTCTCGA-GACTTTCTCAGCCTCCTTCTGCTTTTT (FDPS shRNA sequence #4; SEQ ID NO: 4) were produced in 293 T cells.

HepG2 human hepatocellular carcinoma cells were then infected with lentiviral vectors to determine the efficacy of FDPS knock-down. After 48 hours, RNA was extracted from the cells using the RNeasy RNA isolation kit (Qiagen) and converted to cDNA with the SuperScript VILO cDNA synthesis kit (Thermo Scientific). Expression of FDPS cDNA was determined by quantitative PCR on an Applied Biosystems StepOne qPCR machine using a SYBR Green PCR mix (Thermo Scientific) and FDPS primers (Forward primer: 5'-AGGAATTGATGGCGAGAAGG-3' (SEQ ID NO: 61) and Reverse primer: 5'-CCCAAAGAGGT-CAAGGTAATCA-3' (SEQ ID NO: 62)). FDPS expression was normalized to actin levels for each sample using the actin primers (Forward primer: 5'-AGCGCGGCTACAGCT-TCA-3' (SEQ ID NO: 63) and Reverse primer: 5'-GGC-GACGTAGCACAGCTTCT-3') (SEQ ID NO: 64). The relative FDPS RNA expression of the shCon sample is set at 100%. There was an 85% (FDPS sequence #1), 89% (FDPS sequence #2), 46% (FDPS sequence #3), and 98% (FDPS sequence #4) decrease in FDPS expression.

Figure 13:
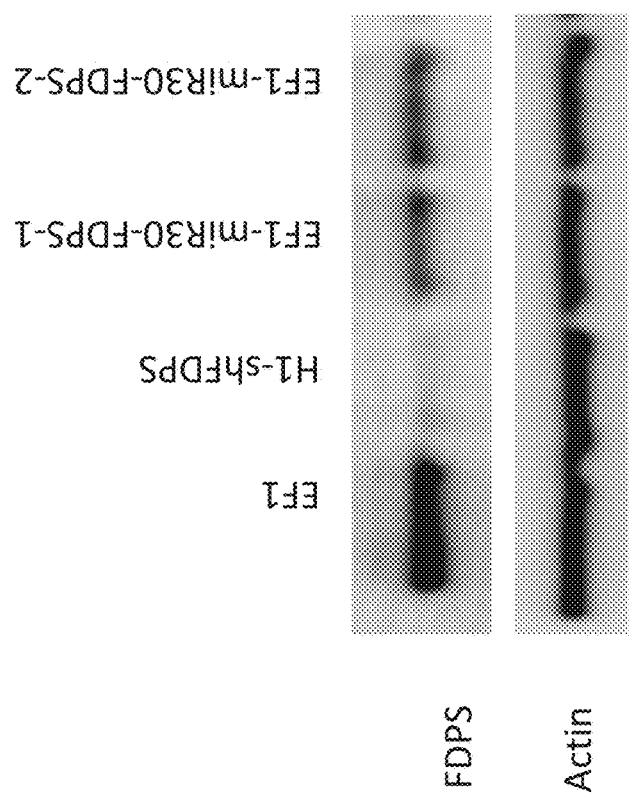
FIG. 13 depicts data demonstrating lentiviral-delivered miR-based RNA interference targeting the human FDPS gene.

Example 11—Lentiviral-Delivered miR-Based RNA Interference Targeting the Human Farnesyl Diphosphate Synthase (FDPS) Gene As shown in FIG. 13, HepG2 human hepatocellular carcinoma cells were infected with lentiviral vectors containing either the H1 promoter (SEQ ID NO: 16) the FDPS shRNA #4 (SEQ ID NO: 4) sequence or the EF-1α promoter (SEQ ID NO: 41) and miR30-based FDPS sequences. After 48 hours, cells were lysed and an immunoblot was performed using an anti-FDPS (Thermo Scientific) and an anti-actin (Sigma) antibody as a protein loading control.

More specifically, HepG2 human hepatocellular carcinoma cells were infected with lentiviral vectors containing either the H1 promoter (SEQ ID NO: 16) and the FDPS shRNA sequence GCAGAAGGAGGCTGAGAAAGTCTCGA-GACTTTCTCAGCCTCCTTCTGCTTTTT (FDPS shRNA sequence #4; SEQ ID NO: 4) or the EF-1alpha promoter (SEQ ID NO: 41) and miR30-based FDPS sequences AAGGTATATTGCTGTTGACAGTGAGCGA-CACTTTCTCAGCCTCCTTCTGCGTGAA GCCACA-GATGGCAGAAGGAGGCTGAGAAAGTGCTGC-CTACTGCCTCGGACTTCA AGGGGCT (miR30 FDPS sequence #1; SEQ ID NO: 5) and AAGGTATATTGCTGTTGACAGTGAGCGA-CACTTTCTCAGCCTCCTTCTGCGTGAA GCCACA-GATGGCAGAAGGGCTGAGAAAGTGCTGCCTACT-GCCTCGGACTTCAAG GGGCT (miR30 FDPS sequence #2; SEQ ID NO: 6).

After 48 hours, cells were lysed with NP-40 lysis buffer and protein was quantified with the Bio-Rad protein assay reagent. Protein samples at 50 micrograms were electrophoresed on 4-12% Bis-Tris gels (Thermo Scientific and transferred to PVDF membranes (EMD Millipore). An immunoblot was performed using an anti-FDPS (Thermo Scientific) and an anti-actin (Sigma) antibody as a protein loading control. Antibodies were bound with HRP-conjugated secondary antibodies and detected with a Licor c-DiGit Blot scanner using the Immobilon Western ECL reagent (EMD Millipore). The densitometry of the immunoblot bands were quantified with the NIH image software. The LV control with the EF-1 promoter was set at 100%. There was a 68% (LV-shFDPS #4), 43% (LV-miR FDPS #1), and 38% (LV-miR FDPS #3) reduction of FDPS protein expression.

Example 12—Knock-Down of FDPS for 3 Days in HepG2 Liver Carcinoma Cells by Adeno-Associated Virus (AAV)-Expressing FDPS shRNA #4

Figure 14:
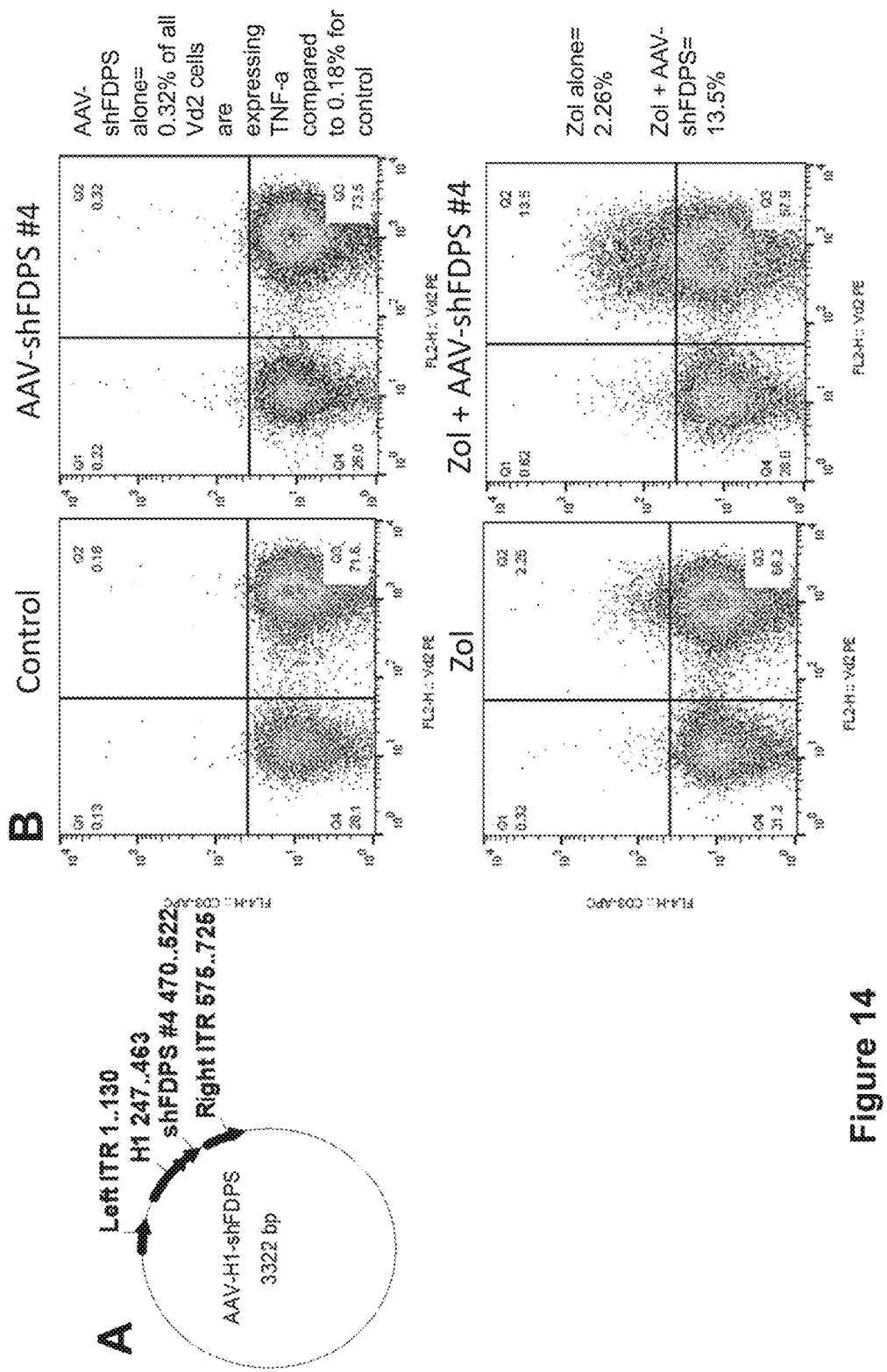
FIG. 14 depicts data demonstrating activation of Vδ2+ T cells by HepG2 carcinoma cells with an adeno-associated virus expressing FDPS shRNA #4 (SEQ ID NO: 4), as described herein.
Figure 15:
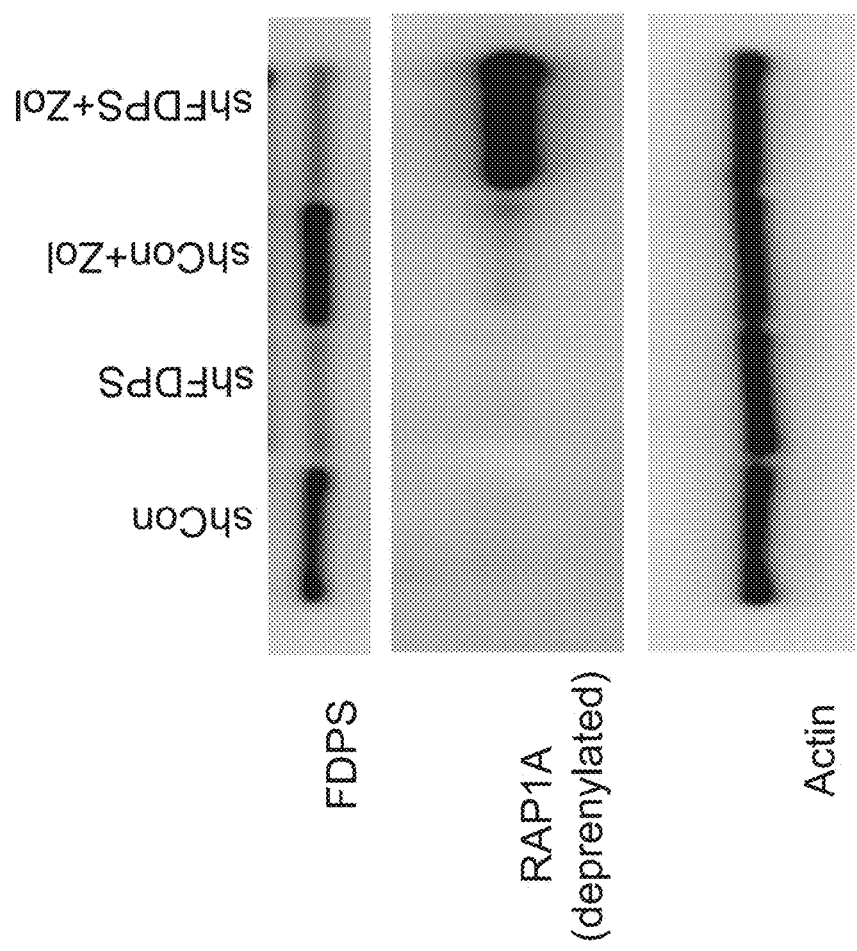
FIG. 15 depicts immunoblot data demonstrating lack of RAP1 prenylation in the cells transduced with LV-shFDPS and treated with zoledronic acid.

This Example illustrates that knock-down of FDPS for 3 days in HepG2 liver carcinoma cells by adeno-associated virus (AAV)-expressing FDPS shRNA #4 (SEQ ID NO: 4) stimulates TNF-α expression in GD T cells (FIG. 14, Panel B).

HepG2 cells were transduced with control or AAV-FDPS shRNA #4 (SEQ ID NO: 8) for 3 days. Two days after transduction, cells were treated with or without 1 uM zoledronic acid. After 24 hours, the transduced HepG2 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms (FIG. 14, Panel B).

AAV Vector Construction.

FDPS shRNA sequence #4 (SEQ ID NO: 4) was inserted into the pAAV plasmid (Cell Biolabs). FDPS oligonucleotide sequences containing BamHI and EcoRI restriction sites were synthesized by Eurofins MWG Operon. Overlapping sense and antisense oligonucleotide sequences were mixed and annealed during cooling from 70 degrees Celsius to room temperature. The pAAV was digested with the restriction enzymes BamHI and EcoRI for one hour at 37 degrees Celsius. The digested pAAV plasmid was purified by agarose gel electrophoresis and extracted from the gel using a DNA gel extraction kit from Thermo Scientific. The DNA concentrations were determined and vector to oligo (3:1 ratio) were mixed, allowed to anneal, and ligated. The ligation reaction was performed with T4 DNA ligase for 30 minutes at room temperature. 2.5 microliters of the ligation mix were added to 25 microliters of STBL3 competent bacterial cells. Transformation was achieved after heat-shock at 42 degrees Celsius. Bacterial cells were spread on agar plates containing ampicillin and drug-resistant colonies (indicating the presence of ampicillin-resistance plasmids) were recovered and expanded in LB broth. To check for insertion of the oligo sequences, plasmid DNA was extracted from harvested bacteria cultures with the Thermo Scientific DNA mini prep kit. Insertion of shRNA sequences in the pAAV plasmid was verified by DNA sequencing using a specific primer for the promoter used to regulate shRNA expression. An exemplary AAV vector with a H1 promoter (SEQ ID NO: 16), shFDPS sequence (e.g., SEQ ID NO: 4), Left Inverted Terminal Repeat (Left ITR; SEQ ID NO: 65), and Right Inverted Terminal Repeat (Right ITR; SEQ ID NO: 66) can be found in FIG. 14, Panel A).

Production of AAV Particles.

The AAV-FDPS shRNA plasmid was combined with the plasmids pAAV-RC2 (Cell Biolabs) and pHelper (Cell Biolabs). The pAAV-RC2 plasmid contains the Rep and AAV2 capsid genes and pHelper contains the adenovirus E2A, E4, and VA genes. To produce AAV particles, these plasmids were transfected in the ratio 1:1:1 (pAAV-shFDPS: pAAV-RC2: pHelper) into 293T cells. For transfection of cells in 150 mm dishes (BD Falcon), 10 micrograms of each plasmid were added together in 1 ml of DMEM. In another tube, 60 microliters of the transfection reagent PEI (1 microgram/ml) (Polysciences) was added to 1 ml of DMEM. The two tubes were mixed together and allowed to incubate for 15 minutes. Then the transfection mixture was added to cells and the cells were collected after 3 days. The cells were lysed by freeze/thaw lysis in dry ice/isopropanol. Benzonase nuclease (Sigma) was added to the cell lysate for 30 minutes at 37 degrees Celsius. Cell debris were then pelleted by centrifugation at 4 degrees Celsius for 15 minutes at 12,000 rpm. The supernatant was collected and then added to target cells.

Example 13—Decreased RAP1 Prenylation in the Cells Transduced with LV-shFDPS and Treated with Zoledronic Acid This Example illustrates that lentiviral-delivered shRNA targeting the human farnesyl diphosphate synthase (FDPS) gene and zoledronic acid synergize to inhibit farnesyl diphosphate production.

FDPS is an enzyme in the isoprenoid synthesis pathway that catalyzes the production of farnesyl diphosphate. Inhibiting the enzyme activity of FDPS by zoledronic acid or reduced protein expression by shRNA-mediated knockdown will result in reduced farnesyl diphosphate levels. Farnesylation of cellular proteins requires farnesyl diphosphate. RAP1A is a protein that is modified by farnesylation, which can be used as a biomarker for levels of cellular farnesyl diphosphate. An antibody that specifically recognizes reduced RAP1A farnesylation was used to measure FDPS activity after transduction with LV-shFDPS alone or in combination with zoledronic acid. HepG2 human hepatocellular carcinoma cells were infected with lentiviral vectors containing FDPS shRNA sequence #4. For the zoledronic acid treated cells, zoledronic acid (Sigma) was added for the last 24 hours. After 48 hours, cells were lysed with NP-40 lysis buffer and protein was quantified with the Bio-Rad protein assay reagent. Protein samples at 50 micrograms were electrophoresed on 4-12% Bis-Tris gels (Thermo Scientific and transferred to PVDF membranes (EMD Millipore). An immunoblot was performed using an anti-FDPS (Thermo Scientific), anti-RAP1A (Santa Cruz), and an anti-actin (Sigma) antibody as a protein loading control. Antibodies were bound with HRP-conjugated secondary antibodies and detected with a Licor c-DiGit Blot scanner using the Immobilon Western ECL reagent (EMD Millipore). An increase in the RAP1A band intensity correlates with reduced farnesylation. RAP1A defarnesylation occurred only in the cells transduced with LV-shFDPS and treated with zoledronic acid.

Example 14—Treatment of a Subject with Cancer

LV-FDPS is a Genetic Medicine Delivered by a Lentivirus Vector Via Local Administration to the Site of Late Stage, Non-Resectable Hepatocellular Carcinoma A Phase I clinical trial will test safety and feasibility of delivering LV-FDPS to the site of hepatocellular carcinoma (HCC) using ultrasound guided cannulation of the liver in patients without concomitant radiotherapy or chemotherapy. It is rationally predicted that this study will result in the successful treatment of HCC. The study is an open label, 4×3 dose escalation (4 dose ranges, up to 3 subjects per dose) to identify the maximum tolerable dose of LV-FDPS in patients 18 years or older with Stage III/IV non-resectable HCC.

LV-FDPS is a genetic therapy designed to reduce expression in tumor cells of the enzyme farnesyl diphosphate synthase. Experimental studies show that tumor cells modified by LV-FDPS induce the anti-tumor activity of human gamma delta T cells, including the capacity for tumor killing by cellular cytotoxicity.

Subjects with target lesions ≥1 cm in longest diameter (measured by helical CT) and ≤4.9 cm maximum diameter and meeting inclusion and exclusion criteria detailed below, are enrolled into the next available dosing category. A maximum of 3 subjects are recruited for each dosage group. The dose is number of transducing units of LV-FDPS as described in the product release criteria, delivered via intrahepatic cannulation in a single bolus with volume not to exceed 25 mL. The minimum dose is $1\times10^9$ transducing units and escalation is 10-fold to a next dose of $1\times10^{10}$ transducing units, the next dose is $1\times10^{11}$ transducing units, and a maximum dose of $1\times10^{12}$ transducing units based on reported experience with recombinant adenovirus therapy for HCC (Sangro et al., A phase I clinic trial of thymidine kinase-based gene therapy in advanced hepatocellular carcinoma, 2010, *Cancer Gene Ther.* 17:837-43). Subjects are enrolled, treated and evaluated for 3 months. All safety evaluations are completed for each group prior to enrolling and treating subjects at the next higher dose level. Enrollment and dose escalation continue until a maximum tolerable dose is achieved or the study is terminated.

Cannulation is via the left subclavian artery until tip of catheter is at the proper hepatic artery junction. Cannulation is guided by ultrasonography as described (Lin et al., Clinical effects of intra-arterial infusion chemotherapy with cisplatin, mitomycin C, leucovor and 5-Fluorouracil for unresectable advanced hepatocellular carcinoma, 2004, *J. Chin. Med. Assoc.* 67:602-10).

Primary Outcome Measures
  Safety:
    Systemic and locoregional adverse events are graded according to CTCAS and coded according to MedRA. The adverse events data for all subjects at a single dose range will be evaluated prior to dose escalation. The final safety assessment incorporates data from all dose ranges.
Secondary Outcome Measures
  Lesion distribution and retention of LV-FDPS following locoregional administration and subsequent biopsy or necropsy to obtain tissues.
  Objective response rate (ORR) in target and measurable non-local lesions (if present) by physical analysis, medical imaging or biopsy during 3 months after treatment.
  Levels of LV-FDPS in blood stream during 10 minutes, 30 minutes, 1 hour and 1 day after local injection.
  Changes in markers of hepatic function including ALP, ALT, ASAT, total bilirubin and GGT during 3 months after treatment.
  Disease free survival beyond historical control (no LV-FDPS) patients in ad hoc analysis.
Inclusion Criteria
  Greater than 18 years and including both males and females.
  Diagnosis confirmed by histology or cytology or based on currently accepted clinical standards of hepatocellular carcinoma of parenchyma cell origin that is not amenable, at the time of screening, to resection, transplant or other potentially curative therapies.
  Treating physician determines that the lesion is amenable to locoregional targeted delivery.
  Target lesion must represent measurable disease with a unidimensional longest diameter of $\geq 1.0$ cm by computed tomography; the maximum longest diameter is $\leq 5.0$ cm.
  Karnofsky performance score 60-80% of ECOG values.
  Life expectancy $\geq 12$ weeks.
  Hematopoietic function: WBC $\geq 2,500/mm^3$; ANC $\geq 1000/mm^3$; Hemoglobin $\geq 8$ g/dL; Platelet count $\geq 50,000/mm^3$; Coagulation INR $\leq 1.3$.
  AST and ALT <5 times ULN; ALPS <5 time ULN. Bilirubin $\leq 1.5$ times ULV; Creatine $\leq 1.5$ times ULN and eGFR $\geq 50$.
  Thyroid function: Total T3 or free T3, total T4 or free T4 and THC $\leq$CTCAE Grade 2 abnormality.
  Renal, cardiovascular and respiratory function adequate in the opinion of the attending physician.
  Immunological function: Circulating Vgamma9Vdelta2+ T cells $\geq 30/mm^3$; no immunodeficiency disease.
  Negative for HIV by serology and viral RNA test.
  Written informed consent.
Exclusion Criteria
  Target lesion contiguous with, encompasses or infiltrates blood vessel.
  Primary HCC amenable to resection, transplantation or other potentially curative therapies.
  Hepatic surgery or chemoembolization within the past 4 months.
  Hepatic radiation or whole body radiation therapy within past 4 months.
  Chemotherapy with 4 weeks or any use of nitrosourea, mitomycin C or cisplatin.
  Current or within past 4 weeks receipt of aminobisphosphonate therapy
  Investigational agents within 4 weeks or <5 drug half-lives.
  Impaired wound healing due to diabetes.
  Significant psychiatric illness, alcohol dependence or illicit drug use.
  Unwilling to comply with study protocols and reporting requirements.
  Aminobisphosphonate treatment within past 4 months.
  Presence of clinically significant cardiovascular, cerebrovascular (stroke), immunological (except hepatitis B or C virus infection, viral hepatitis or cirrhosis), endocrine or central nervous system disorders; current encephalopathy; variceal bleeding requiring hospitalization or transfusion within past 4 months.
  History of HIV or acquired immune deficiency syndrome.
  Current or prior treatment with antiretroviral medications.
  Pregnant, lactating or refusal to adopt barrier or chemical contraceptive use throughout trial and follow-up interval.

LV-FDPS is a Genetic Medicine Delivered by a Lentivirus Vector Via Local Administration to the Site of Late Stage, Non-Resectable Hepatocellular Carcinoma—Adjunct Administration of Aminobisphosphonate A Phase I clinical trial will test safety and feasibility of delivering LV-FDPS to the site of hepatocellular carcinoma (HCC) using ultrasound guided cannulation of the liver in patients with concomitant aminobisphosphonate chemotherapy. It is rationally predicted that this study will result in the successful treatment of HCC. The study is an open label, 4×3 dose escalation (4 dose ranges, up to 3 subjects per dose) to identify the maximum tolerable dose of LV-FDPS in patients 18 years or older with Stage III/IV non-resectable HCC.

LV-FDPS is a genetic therapy designed to reduce expression in tumor cells of the enzyme farnesyl diphosphate synthase. Experimental studies show that tumor cells modified by LV-FDPS induce the anti-tumor activity of human gamma delta T cells, including the capacity for tumor killing by cellular cytotoxicity. Prior experimental studies also showed the potential for positive interactions of LV-FDPS and specific aminobisphosphonate drugs that may be prescribed in primary or metastatic diseases. For this study, subjects will receive dose escalating amounts of LV-FDPS with continuous standard of care dosing with Aredia® (pamidronate), Zometa® (zoledronic acid) or Actonel® (risedronate) according to physician advice and subject preference.

Subjects with target lesions ≥1 cm in longest diameter (measured by helical CT) and ≤4.9 cm maximum diameter and meeting inclusion and exclusion criteria detailed below, are enrolled and started on aminobisphonate therapy. 30 days later size of the target lesion is re-evaluated to ensure subjects still meet starting criteria for LV-FDPS. Subjects without objective clinical response on aminobisphosphonate are enrolled into the next available LV-FDPS dosing category. A maximum of 3 subjects are recruited for each dosage group and all continue on aminobisphosphonate fir the study duration unless otherwise advised by the attending physician. The LV-FDPS dose is a number of transducing units of LV-FDPS as described in the product release criteria, delivered via intrahepatic cannulation in a single bolus with volume not to exceed 25 mL. The minimum dose is $1 \times 10^9$ transducing units and escalation is 10-fold to a next dose of $1 \times 10^{10}$ transducing units, the next dose is $1 \times 10^{11}$ transducing units, and a maximum dose of $1 \times 10^{12}$ transducing units based on reported experience with recombinant adenovirus therapy for HCC (Sangro, et al., A phase I clinic trial of thymidine kinase-based gene therapy in advanced hepatocellular carcinoma, 2010, *Cancer Gene Ther.* 17:837-43). Subjects are enrolled, treated and evaluated for 3 months. All safety evaluations are completed for each group prior to enrolling and treating subjects at the next higher dose level. Enrollment and dose escalation continue until a maximum tolerable dose is achieved or the study is terminated.

Cannulation is via the left subclavian artery until tip of catheter is at the proper hepatic artery junction. Cannulation is guided by ultrasonography as described (Lin et al., Clinical effects of intra-arterial infusion chemotherapy with cisplatin, mitomycin C, leucovor and 5-Fluorouracil for unresectable advanced hepatocellular carcinoma, 2004, *J. Chin. Med. Assoc.* 67:602-10).

Primary Outcome Measures

Safety: Systemic and locoregional adverse events are graded according to CTCAS and coded according to MedRA. The adverse events data for all subjects at a single dose range will be evaluated prior to dose escalation. The final safety assessment incorporates data from all dose ranges.

Secondary Outcome Measures
- Lesion distribution and retention of LV-FDPS following locoregional administration and subsequent biopsy or necropsy to obtain tissues.
- Objective response rate (ORR) in target and measurable non-local lesions (if present) by physical analysis, medical imaging or biopsy during 3 months after treatment.
- Levels of LV-FDPS in blood stream during 10 minutes, 30 minutes, 1 hour and 1 day after local injection.
- Changes in markers of hepatic function including ALP, ALT, ASAT, total bilirubin and GGT during 3 months after treatment.
- Disease free survival beyond historical control (no LV-FDPS) patients in ad hoc analysis.

Inclusion Criteria
- Greater than 18 years and including both males and females.
- Diagnosis confirmed by histology or cytology or based on currently accepted clinical standards of hepatocellular carcinoma of parenchyma cell origin that is not amenable, at the time of screening, to resection, transplant or other potentially curative therapies.
- Treating physician determines that the lesion is amenable to locoregional targeted delivery.
- Target lesion must represent measurable disease with a unidimensional longest diameter of ≥1.0 cm by computed tomography; the maximum longest diameter is ≤5.0 cm.
- Karnofsky performance score 60-80% of ECOG values.
- Life expectancy ≥12 weeks.
- Hematopoietic function: WBC ≥2,500/mm$^3$; ANC ≥1000/mm$^3$; Hemoglobin ≥8 g/dL; Platelet count ≥50,000/mm$^3$; Coagulation INR ≤1.3.
- AST and ALT <5 times ULN; ALPS <5 time ULN. Bilirubin ≤1.5 times ULV; Creatine ≤1.5 times ULN and eGFR ≥50.
- Thyroid function: Total T3 or free T3, total T4 or free T4 and THC ≤CTCAE Grade 2 abnormality.
- Renal, cardiovascular and respiratory function adequate in the opinion of the attending physician.
- Immunological function: Circulating Vgamma9Vdelta2+ T cells ≥30/mm$^3$; no immunodeficiency disease.
- Negative for HIV by serology and viral RNA test.
- Written informed consent.

Exclusion Criteria
- Intolerant to or unwilling to continue aminobisphosphonate adjunct therapy.
- Objective clinical response after aminobisphosphonate therapy.
- Target lesion contiguous with, encompasses or infiltrates blood vessel.
- Primary HCC amenable to resection, transplantation or other potentially curative therapies.
- Hepatic surgery or chemoembolization within the past 4 months.
- Hepatic radiation or whole body radiation therapy within past 4 months.
- Chemotherapy excluding aminobisphosphonate, within 4 weeks or any use of nitrosourea, mitomycin C or cisplatin.
- Investigational agents within 4 weeks or <5 drug half-lives.
- Impaired wound healing due to diabetes.
- Significant psychiatric illness, alcohol dependence or illicit drug use.
- Unwilling to comply with study protocols and reporting requirements.
- Presence of clinically significant cardiovascular, cerebrovascular (stroke), immunological (except hepatitis B or C virus infection, viral hepatitis or cirrhosis), endocrine or central nervous system disorders; current encephalopathy; variceal bleeding requiring hospitalization or transfusion within past 4 months.
- History of HIV or acquired immune deficiency syndrome.
- Current or prior treatment with antiretroviral medications.
- Pregnant, lactating or refusal to adopt barrier or chemical contraceptive use throughout trial and follow-up interval.

Example 15—Treatment of a Subject with Chronic Viral Disease(s) of the Liver

LV-FDPS is a Genetic Medicine Delivered by a Lentivirus Vector Via Local Administration to Liver for the Treatment of Hepatitis B Virus, Hepatitis C Virus, HIV or Other Viral Infection of the Liver A Phase I clinical trial will test safety and feasibility of delivering LV-FDPS to virally infected liver using ultrasound guided cannulation. It is rationally predicted that this study will result in the successful treatment of infections of the liver. The study is an open label, 4×3 dose escalation (4 dose ranges, up to 3 subjects per dose) to identify the maximum tolerable dose of LV-FDPS in patients 18 years or older with chronic viral disease of the liver that is resistant to chemotherapy.

LV-FDPS is a genetic therapy designed to reduce expression in tumor cells of the enzyme farnesyl diphosphate synthase. Experimental studies show that tumor cells modified by LV-FDPS induce human gamma delta T cells, including a capacity for cellular cytotoxicity against virally-infected cells.

Subjects with confirmed viral infection of the liver including hepatitis B virus, hepatitis C virus, HIV or other viruses are enrolled into the next available LV-FDPS dosing category. A maximum of 3 subjects are recruited for each dosage group. The LV-FDPS dose is a number of transducing units of LV-FDPS as described in the product release criteria, delivered via intrahepatic cannulation in a single bolus with volume not to exceed 25 mL. The minimum dose is $1\times10^9$ transducing units and escalation is 10-fold to a next dose of $1\times10^{10}$ transducing units, the next dose is $1\times10^{11}$ transducing units, and a maximum dose of $1\times10^{12}$ transducing units based on reported experience with recombinant adenovirus therapy for HCC (Sangro, et al., A phase I clinic trial of thymidine kinase-based gene therapy in advanced hepatocellular carcinoma, 2010, *Cancer Gene Ther.* 17:837-43). Subjects are enrolled, treated and evaluated for 3 months. All safety evaluations are completed for each group prior to enrolling and treating subjects at the next higher dose level. Enrollment and dose escalation continue until a maximum tolerable dose is achieved or the study is terminated.

Cannulation is via the left subclavian artery until tip of catheter is at the proper hepatic artery junction. Cannulation is guided by ultrasonography as described (Lin et al., Clinical effects of intra-arterial infusion chemotherapy with cisplatin, mitomycin C, leucovor and 5-Fluorouracil for unresectable advanced hepatocellular carcinoma, 2004, *J. Chin. Med. Assoc.* 67:602-10).

Primary Outcome Measures

Safety: Systemic and locoregional adverse events are graded according to CTCAS and coded according to MedRA. The adverse events data for all subjects at a single dose range will be evaluated prior to dose escalation. The final safety assessment incorporates data from all dose ranges.

Secondary Outcome Measures

Lesion distribution and retention of LV-FDPS following locoregional administration and subsequent biopsy or necropsy to obtain tissues.

Objective response rate (ORR) measured as a Sustained Viral Response (SVR) within the organ or systemically during 3 months after treatment.

Levels of LV-FDPS in blood stream during 10 minutes, 30 minutes, 1 hour and 1 day after local injection.

Changes in markers of hepatic function including ALP, ALT, ASAT, total bilirubin and GGT during 3 months after treatment.

Disease free survival beyond historical control (no LV-FDPS) patients in ad hoc analysis.

Inclusion Criteria

Greater than 18 years and including both males and females.

Diagnosis confirmed by histology or cytology or based on currently accepted clinical standards of chronic viral infection of the liver that is not amenable, at the time of screening, to resection, transplant or other potentially curative therapies.

Treating physician determines that the lesion is amenable to locoregional targeted delivery.

Karnofsky performance score 60-80% of ECOG values.

Life expectancy ≥12 weeks.

Hematopoietic function: WBC ≥2,500/mm³; ANC ≥1000/mm³; Hemoglobin ≥8 g/dL; Platelet count ≥50,000/mm³; Coagulation INR ≤1.3.

AST and ALT <5 times ULN; ALPS <5 time ULN. Bilirubin ≤1.5 times ULV; Creatine ≤1.5 times ULN and eGFR ≥50.

Thyroid function: Total T3 or free T3, total T4 or free T4 and THC ≤CTCAE Grade 2 abnormality.

Renal, cardiovascular and respiratory function adequate in the opinion of the attending physician.

Immunological function: Circulating Vgamma9Vdelta2+ T cells ≥30/mm³; no immunodeficiency disease.

Negative for HIV by serology and viral RNA test.

Written informed consent.

Exclusion Criteria

Chronic viral disease amenable to resection, transplantation or other potentially curative therapies.

Hepatic surgery or chemoembolization within the past 4 months.

Hepatic radiation or whole body radiation therapy within past 4 months.

Investigational agents within 4 weeks or <5 drug half-lives.

Current (within past 4 weeks) or ongoing receipt of aminobisphonate therapy.

Impaired wound healing due to diabetes.

Significant psychiatric illness, alcohol dependence or illicit drug use.

Unwilling to comply with study protocols and reporting requirements.

Presence of clinically significant cardiovascular, cerebrovascular (stroke), immunological (except virus infection, viral hepatitis or cirrhosis), endocrine or central nervous system disorders; current encephalopathy; variceal bleeding requiring hospitalization or transfusion within past 4 months.

Pregnant, lactating or refusal to adopt barrier or chemical contraceptive use throughout trial and follow-up interval.

LV-FDPS is a Genetic Medicine Delivered by a Lentivirus Vector Via Local Administration to Liver for the Treatment of Hepatitis B Virus, Hepatitis C Virus, HIV or Other Viral Infection of the Liver—Concomitant Adjunct Aminobisphosphonate Therapy A Phase I clinical trial will test safety and feasibility of delivering LV-FDPS to virally infected liver using ultrasound guided cannulation. It is rationally predicted that this study will result in the successful treatment of infections of the liver. The study is an open label, 4×3 dose escalation (4 dose ranges, up to 3 subjects per dose) to identify the maximum tolerable dose of LV-FDPS in patients 18 years or older with chronic viral disease of the liver that is resistant to chemotherapy.

LV-FDPS is a genetic therapy designed to reduce expression in tumor cells of the enzyme farnesyl diphosphate synthase. Experimental studies show that tumor cells modified by LV-FDPS induce human gamma delta T cells, including a capacity for cellular cytotoxicity against virally-infected cells. Prior experimental studies also showed the potential for positive interactions of LV-FDPS and specific aminobisphosphonate drugs that may be prescribed during infectious disease. For this study, subjects will receive dose escalating amounts of LV-FDPS with continuous standard of care dosing with Aredia® (pamidronate), Zometa® (zoledronic acid) or Actonel® (risedronate) according to physician advice and subject preference.

Subjects with confirmed viral infection of the liver including hepatitis B virus, hepatitis C virus, HIV or other viruses will initiate aminobisphosphonate therapy for 45 days before re-screening to meet enrollment criteria for LV-FDPS treatment of infectious disease. Eligible subjects are enrolled into the next available LV-FDPS dosing category. A maximum of 3 subjects are recruited for each dosage group. The LV-FDPS dose is a number of transducing units of LV-FDPS as described in the product release criteria, delivered via intrahepatic cannulation in a single bolus with volume not to exceed 25 mL. The minimum dose is $1 \times 10^9$ transducing units and escalation is 10-fold to a next dose of $1 \times 10^{10}$ transducing units, the next dose is $1 \times 10^{11}$ transducing units, and a maximum dose of $1 \times 10^{12}$ transducing units based on reported experience with recombinant adenovirus therapy for HCC (Sangro, et al., A phase I clinic trial of thymidine kinase-based gene therapy in advanced hepatocellular carcinoma, 2010, *Cancer Gene Ther.* 17:837-43). Subjects are enrolled, treated and evaluated for 3 months. All safety evaluations are completed for each group prior to enrolling and treating subjects at the next higher dose level. Enrollment and dose escalation continue until a maximum tolerable dose is achieved or the study is terminated.

Cannulation is via the left subclavian artery until tip of catheter is at the proper hepatic artery junction. Cannulation is guided by ultrasonography as described (Lin et al., Clinical effects of intra-arterial infusion chemotherapy with cisplatin, mitomycin C, leucovor and 5-Fluorouracil for unresectable advanced hepatocellular carcinoma, 2004, *J. Chin. Med. Assoc.* 67:602-10).

Primary Outcome Measures

Safety: Systemic and locoregional adverse events are graded according to CTCAS and coded according to MedRA. The adverse events data for all subjects at a single dose range will be evaluated prior to dose escalation. The final safety assessment incorporates data from all dose ranges.

Secondary Outcome Measures

Lesion distribution and retention of LV-FDPS following locoregional administration and subsequent biopsy or necropsy to obtain tissues.

Objective response rate (ORR) measured as a Sustained Viral Response (SVR) within the organ or systemically during 3 months after treatment.

Levels of LV-FDPS in blood stream during 10 minutes, 30 minutes, 1 hour and 1 day after local injection.

Changes in markers of hepatic function including ALP, ALT, ASAT, total bilirubin and GGT during 3 months after treatment.

Disease free survival beyond historical control (no LV-FDPS) patients in ad hoc analysis.

Inclusion Criteria

Greater than 18 years and including both males and females.

Diagnosis confirmed by histology or cytology or based on currently accepted clinical standards of chronic viral infection of the liver that is not amenable, at the time of screening, to resection, transplant or other potentially curative therapies.

Treating physician determines that the lesion is amenable to locoregional targeted delivery.

Karnofsky performance score 60-80% of ECOG values.

Life expectancy ≥12 weeks.

Hematopoietic function: WBC ≥2,500/mm³; ANC ≥1000/mm³; Hemoglobin ≥8 g/dL; Platelet count ≥50,000/mm³; Coagulation INR ≤1.3.

AST and ALT <5 times ULN; ALPS <5 time ULN. Bilirubin ≤1.5 times ULV; Creatine ≤1.5 times ULN and eGFR ≥50.

Thyroid function: Total T3 or free T3, total T4 or free T4 and THC ≤CTCAE Grade 2 abnormality.

Renal, cardiovascular and respiratory function adequate in the opinion of the attending physician.

Immunological function: Circulating Vgamma9Vdelta2+ T cells ≥30/mm³; no immunodeficiency disease.

Negative for HIV by serology and viral RNA test.

Written informed consent.

Exclusion Criteria

Chronic viral disease amenable to resection, transplantation or other potentially curative therapies.

Hepatic surgery or chemoembolization within the past 4 months.

Hepatic radiation or whole body radiation therapy within past 4 months.

Investigational agents within 4 weeks or <5 drug half-lives.

Impaired wound healing due to diabetes.

Significant psychiatric illness, alcohol dependence or illicit drug use.

Unwilling to comply with study protocols and reporting requirements.

Presence of clinically significant cardiovascular, cerebrovascular (stroke), immunological (except virus infection, viral hepatitis or cirrhosis), endocrine or central nervous system disorders; current encephalopathy; variceal bleeding requiring hospitalization or transfusion within past 4 months.

Pregnant, lactating or refusal to adopt barrier or chemical contraceptive use throughout trial and follow-up interval.

Sequences

The following sequences are referred to herein:

| SEQ ID NO: | Description | Sequence |
|---|---|---|
| 1 | FDPS shRNA sequence #1 | GTCCTGGAGTACAATGCCATTCTCGAGAATGGCATT GTACTCCAGGACTTTTT |
| 2 | FDPS shRNA sequence #2 | GCAGGATTTCGTTCAGCACTTCTCGAGAAGTGCTGA ACGAAATCCTGCTTTTT |
| 3 | FDPS shRNA sequence #3 | GCCATGTACATGGCAGGAATTCTCGAGAATTCCTGC CATGTACATGGCTTTTT |

| SEQ ID NO: | Description | Sequence |
|---|---|---|
| 4 | FDPS shRNA sequence #4 | GCAGAAGGAGGCTGAGAAAGTCTCGAGACTTTCTC AGCCTCCTTCTGCTTTTT |
| 5 | miR30 FDPS sequence #1 | AAGGTATATTGCTGTTGACAGTGAGCGACACTTTCT CAGCCTCCTTCTGCGTGAAGCCACAGATGGCAGAA GGAGGCTGAGAAAGTGCTGCCTACTGCCTCGGACTT CAAGGGGCT |
| 6 | miR30 FDPS sequence #2 | AAGGTATATTGCTGTTGACAGTGAGCGACACTTTCT CAGCCTCCTTCTGCGTGAAGCCACAGATGGCAGAA GGGCTGAGAAAGTGCTGCCTACTGCCTCGGACTTCA AGGGGCT |
| 7 | miR30 FDPS sequence #3 | TGCTGTTGACAGTGAGCGACTTTCTCAGCCTCCTTCT GCGTGAAGCCACAGATGGCAGAAGGAGGCTGAGAA AGTTGCCTACTGCCTCGGA |
| 8 | miR155 FDPS sequence #1 | CCTGGAGGCTTGCTGAAGGCTGTATGCTGACTTTCT CAGCCTCCTTCTGCTTTTGGCCACTGACTGAGCAGA AGGGCTGAGAAAGTCAGGACACAAGGCCTGTTACT AGCACTCA |
| 9 | miR21 FDPS sequence #1 | CATCTCCATGGCTGTACCACCTTGTCGGACTTTCTC AGCCTCCTTCTGCCTGTTGAATCTCATGGCAGAAGG AGGCGAGAAAGTCTGACATTTTGGTATCTTTCATCT GACCA |
| 10 | miR185 FDPS sequence #1 | GGGCCTGGCTCGAGCAGGGGCGAGGGATACTTTC TCAGCCTCCTTCTGCTGGTCCCCTCCCCGCAGAAGG AGGCTGAGAAAGTCCTTCCCTCCCAATGACCGCGTC TTCGTCG |
| 11 | Rous Sarcoma virus (RSV) promoter | GTAGTCTTATGCAATACTCTTGTAGTCTTGCAACAT GGTAACGATGAGTTAGCAACATGCCTTACAAGGAG AGAAAAAGCACCGTGCATGCCGATTGGTGGAAGTA AGGTGGTACGATCGTGCCTTATTAGGAAGGCAACA GACGGGTCTGACATGGATTGGACGAACCACTGAAT TGCCGCATTGCAGAGATATTGTATTTAAGTGCCTAG CTCGATACAATAAACG |
| 12 | 5' Long terminal repeat (LTR) | GGTCTCTCTGGTTAGACCAGATCTGAGCCTGGGAGC TCTCTGGCTAACTAGGGAACCCACTGCTTAAGCCTC AATAAAGCTTGCCTTGAGTGCTTCAAGTAGTGTGTG CCCGTCTGTTGTGTGACTCTGGTAACTAGAGATCCC TCAGACCCTTTTAGTCAGTGTGGAAAATCTCTAGCA |
| 13 | Psi Packaging signal | TACGCCAAAAATTTTGACTAGCGGAGGCTAGAAGG AGAGAG |
| 14 | Rev response element (RRE) | AGGAGCTTTGTTCCTTGGGTTCTTGGGAGCAGCAGG AAGCACTATGGGCGCAGCCTCAATGACGCTGACGG TACAGGCCAGACAATTATTGTCTGGTATAGTGCAGC AGCAGAACAATTTGCTGAGGGCTATTGAGGCGCAA CAGCATCTGTTGCAACTCACAGTCTGGGGCATCAAG CAGCTCCAGGCAAGAATCCTGGCTGTGGAAAGATA CCTAAAGGATCAACAGCTCC |
| 15 | Central polypurine tract (cPPT) | TTTTAAAAGAAAAGGGGGGATTGGGGGGTACAGTG CAGGGGAAAGAATAGTAGACATAATAGCAACAGAC ATACAAACTAAAGAATTACAAAAACAAATTACAAA ATTCAAAATTTTA |
| 16 | Polymerase III shRNA promoters; H1 promoter | GAACGCTGACGTCATCAACCCGCTCCAAGGAATCG CGGGCCCAGTGTCACTAGGCGGGAACACCCAGCGC GCGTGCGCCCTGGCAGGAAGATGGCTGTGAGGGAC AGGGGAGTGGCGCCCTGCAATATTTGCATGTCGCTA TGTGTTCTGGGAAATCACCATAAACGTGAAATGTCT TTGGATTTGGGAATCTTATAAGTTCTGTATGAGACC ACTT |
| 17 | Long WPRE sequence | AATCAACCTCTGATTACAAAATTTGTGAAAGATTGA CTGGTATTCTTAACTATGTTGCTCCTTTTACGCTATG TGGATACGCTGCTTTAATGCCTTTGTATCATGCTATT GCTTCCCGTATGGCTTTCATTTTCTCCTCCTTGTATA AATCCTGGTTGCTGTCTCTTTATGAGGAGTTGTGGC |

| SEQ ID NO: | Description | Sequence |
|---|---|---|
| | | CCGTTGTCAGGCAACGTGGCGTGGTGTGCACTGTGT TTGCTGACGCAACCCCCACTGGTTGGGGCATTGCCA CCACCTGTCAGCTCCTTTCCGGGACTTTCGCTTTCCC CCTCCCTATTGCCACGGCGGAACTCATCGCCGCCTG CCTTGCCCGCTGCTGGACAGGGGCTCGGCTGTTGGG CACTGACAATTCCGTGGTGTTGTCGGGGAAATCATC GTCCTTTCCTTGGCTGCTCGCCTGTGTTGCCACCTGG ATTCTGCGCGGGACGTCCTTCTGCTACGTCCCTTCG GCCCTCAATCCAGCGGACCTTCCTTCCCGCGGCCTG CTGCCGGCTCTGCGGCCTCTTCCGCGTCTTCGCCTTC GCCCTCAGACGAGTCGGATCTCCCTTTGGGCCGCCT CCCCGCCT |
| 18 | 3' delta LTR | TGGAAGGGCTAATTCACTCCCAACGAAGATAAGAT CTGCTTTTTGCTTGTACTGGGTCTCTCTGGTTAGACC AGATCTGAGCCTGGGAGCTCTCTGGCTAACTAGGGA ACCCACTGCTTAAGCCTCAATAAAGCTTGCCTTGAG TGCTTCAAGTAGTGTGTGCCCGTCTGTTGTGTGACT CTGGTAACTAGAGATCCCTCAGACCCTTTTAGTCAG TGTGGAAAATCTCTAGCAGTAGTAGTTCATGTCA |
| 19 | Helper/Rev; Chicken beta actin (CAG) promoter; Transcription | GCTATTACCATGGGTCGAGGTGAGCCCCACGTTCTG CTTCACTCTCCCCATCTCCCCCCCCTCCCCACCCCCA ATTTTGTATTTATTTATTTTTTAATTATTTTGTGCAGC GATGGGGGCGGGGGGGGGGGGGGCGCGCGCCAGG CGGGGCGGGGCGGGGCGAGGGGCGGGGCGGGGCG AGGCGGAGAGGTGCGGCGGCAGCCAATCAGAGCGG CGCGCTCCGAAAGTTTCCTTTTATGGCGAGGCGGCG GCGGCGGCGGCCCTATAAAAAGCGAAGCGCGCGGC GGGCG |
| 20 | Helper/Rev; HIV Gag; Viral capsid | ATGGGTGCGAGAGCGTCAGTATTAAGCGGGGGAGA ATTAGATCGATGGGAAAAAATTCGGTTAAGGCCAG GGGGAAAGAAAAAATATAAATTAAAACATATAGTA TGGGCAAGCAGGGAGCTAGAACGATTCGCAGTTAA TCCTGGCCTGTTAGAAACATCAGAAGGCTGTAGACA AATACTGGGACAGCTACAACCATCCCTTCAGACAG GATCAGAAGAACTTAGATCATTATATAATACAGTAG CAACCCTCTATTGTGTGCATCAAAGGATAGAGATAA AAGACACCAAGGAAGCTTTAGACAAGATAGAGGAA GAGCAAAACAAAAGTAAGAAAAAAGCACAGCAAG CAGCAGCTGACACAGGACACAGCAATCAGGTCAGC CAAAATTACCCTATAGTGCAGAACATCCAGGGGCA AATGGTACATCAGGCCATATCACCTAGAACTTTAAA TGCATGGGTAAAAGTAGTAGAAGAGAAGGCTTTCA GCCCAGAAGTGATACCCATGTTTTCAGCATTATCAG AAGGAGCCACCCCACAAGATTTAAACACCATGCTA AACACAGTGGGGGGACATCAAGCAGCCATGCAAAT GTTAAAAGAGACCATCAATGAGGAAGCTGCAGAAT GGGATAGAGTGCATCCAGTGCATGCAGGGCCTATT GCACCAGGCCAGATGAGAGAACCAAGGGGAAGTGA CATAGCAGGAACTACTAGTACCCTTCAGGAACAAA TAGGATGGATGACACATAATCCACCTATCCCAGTAG GAGAAATCTATAAAAGATGGATAATCCTGGGATTA AATAAAATAGTAAGAATGTATAGCCCTACCAGCATT CTGGACATAAGACAAGGACCAAAGGAACCCTTTAG AGACTATGTAGACCGATTCTATAAAACTCTAAGAGC CGAGCAAGCTTCACAAGAGGTAAAAAATTGGATGA CAGAAACCTTGTTGGTCCAAAATGCGAACCCAGATT GTAAGACTATTTTAAAAGCATTGGGACCAGGAGCG ACACTAGAAGAAATGATGACAGCATGTCAGGGAGT GGGGGGACCCGGCCATAAAGCAAGAGTTTTGGCTG AAGCAATGAGCCAAGTAACAAATCCAGCTACCATA ATGATACAGAAAGGCAATTTTAGGAACCAAAGAAA GACTGTTAAGTGTTTCAATTGTGGCAAAGAAGGGCA CATAGCCAAAAATTGCAGGGCCCCTAGGAAAAAGG GCTGTTGGAAATGTGGAAAGGAAGGACACCAAATG AAAGATTGTACTGAGAGACAGGCTAATTTTTTAGGG AAGATCTGGCCTTCCCACAAGGGAAGGCCAGGGAA TTTTCTTCAGAGCAGACCAGAGCCAACAGCCCCACC AGAAGAGAGCTTCAGGTTTGGGGAAGAGACAACAA CTCCCTCTCAGAAGCAGGAGCCGATAGACAAGGAA CTGTATCCTTTAGCTTCCCTCAGATCACTCTTTGGCA GCGACCCCTCGTCACAATAA |

| SEQ ID NO: | Description | Sequence |
|---|---|---|
| 21 | Helper/Rev; HIV Pol; Protease and reverse transcriptase | ATGAATTTGCCAGGAAGATGGAAACCAAAAATGAT AGGGGGAATTGGAGGTTTTATCAAAGTAGGACAGT ATGATCAGATACTCATAGAAATCTGCGGACATAAA GCTATAGGTACAGTATTAGTAGGACCTACACCTGTC AACATAATTGGAAGAAATCTGTTGACTCAGATTGGC TGCACTTTAAATTTTCCCATTAGTCCTATTGAGACTG TACCAGTAAAATTAAAGCCAGGAATGGATGGCCCA AAAGTTAAACAATGGCCATTGACAGAAGAAAAAT AAAAGCATTAGTAGAAATTTGTACAGAAATGGAAA AGGAAGGAAAAATTTCAAAAATTGGGCCTGAAAAT CCATACAATACTCCAGTATTTGCCATAAAGAAAAAA GACAGTACTAAATGGAGAAAATTAGTAGATTTCAG AGAACTTAATAAGAGAACTCAAGATTTCTGGGAAG TTCAATTAGGAATACCACATCCTGCAGGGTTAAAAC AGAAAAAATCAGTAACAGTACTGGATGTGGGCGAT GCATATTTTTCAGTTCCCTTAGATAAAGACTTCAGG AAGTATACTGCATTTACCATACCTAGTATAAACAAT GAGACACCAGGGATTAGATATCAGTACAATGTGCTT CCACAGGGATGGAAAGGATCACCAGCAATATTCCA GTGTAGCATGACAAAAATCTTAGAGCCTTTTAGAAA ACAAAATCCAGACATAGTCATCTATCAATACATGGA TGATTTGTATGTAGGATCTGACTTAGAAATAGGGCA GCATAGAACAAAAATAGAGGAACTGAGACAACATC TGTTGAGGTGGGGATTTACCACACCAGACAAAAAA CATCAGAAAGAACCTCCATTCCTTTGGATGGGTTAT GAACTCCATCCTGATAAATGGACAGTACAGCCTATA GTGCTGCCAGAAAAGGACAGCTGGACTGTCAATGA CATACAGAAATTAGTGGGAAAATTGAATTGGGCAA GTCAGATTTATGCAGGGATTAAAGTAAGGCAATTAT GTAAACTTCTTAGGGGAACCAAAGCACTAACAGAA GTAGTACCACTAACAGAAGAAGCAGAGCTAGAACT GGCAGAAAACAGGGAGATTCTAAAAGAACCGGTAC ATGGAGTGTATTATGACCCATCAAAAGACTTAATAG CAGAAATACAGAAGCAGGGGCAAGGCCAATGGACA TATCAAATTTATCAAGAGCCATTTAAAAATCTGAAA ACAGGAAAATATGCAAGAATGAAGGGTGCCCACAC TAATGATGTGAAACAATTAACAGAGGCAGTACAAA AAATAGCCACAGAAAGCATAGTAATATGGGGAAAG ACTCCTAAATTTAAATTACCCATACAAAAGGAAACA TGGGAAGCATGGTGGACAGAGTATTGGCAAGCCAC CTGGATTCCTGAGTGGGAGTTTGTCAATACCCCTCC CTTAGTGAAGTTATGGTACCAGTTAGAGAAAGAAC CCATAATAGGAGCAGAAACTTTCTATGTAGATGGG GCAGCCAATAGGGAAACTAAATTAGGAAAAGCAGG ATATGTAACTGACAGAGGAAGACAAAAAGTTGTCC CCCTAACGGACACAACAAATCAGAAGACTGAGTTA CAAGCAATTCATCTAGCTTTGCAGGATTCGGGATTA GAAGTAAACATAGTGACAGACTCACAATATGCATT GGGAATCATTCAAGCACAACCAGATAAGAGTGAAT CAGAGTTAGTCAGTCAAATAATAGAGCAGTTAATA AAAAAGGAAAAAGTCTACCTGGCATGGGTACCAGC ACACAAAGGAATTGGAGGAAATGAACAAGTAGATG GGTTGGTCAGTGCTGGAATCAGGAAAGTACTA |
| 22 | Helper Rev; HIV Integrase; Integration of viral RNA | TTTTTAGATGGAATAGATAAGGCCCAAGAAGAACA TGAGAAATATCACAGTAATTGGAGAGCAATGGCTA GTGATTTTAACCTACCACCTGTAGTAGCAAAAGAAA TAGTAGCCAGCTGTGATAAATGTCAGCTAAAAGGG GAAGCCATGCATGGACAAGTAGACTGTAGCCCAGG AATATGGCAGCTAGATTGTACACATTTAGAAGGAA AAGTTATCTTGGTAGCAGTTCATGTAGCCAGTGGAT ATATAGAAGCAGAAGTAATTCCAGCAGAGACAGGG CAAGAAACAGCATACTTCCTCTTAAAATTAGCAGGA AGATGGCCAGTAAAAACAGTACATACAGACAATGG CAGCAATTTCACCAGTACTACAGTTAAGGCCGCCTG TTGGTGGCGGGGATCAAGCAGGAATTTGGCATTCC CTACAATCCCCAAAGTCAAGGAGTAATAGAATCTAT GAATAAAGAATTAAAGAAAATTATAGGACAGGTAA GAGATCAGGCTGAACATCTTAAGACAGCAGTACAA ATGGCAGTATTCATCCACAATTTTAAAAGAAAAGG GGGGATTGGGGGGTACAGTGCAGGGGAAAGAATAG TAGACATAATAGCAACAGACATACAAACTAAAGAA TTACAAAAACAAATTACAAAAATTCAAAATTTTCGG GTTTATTACAGGGACAGCAGAGATCCAGTTTGGAA AGGACCAGCAAAGCTCCTCTGGAAAGGTGAAGGGG |

| SEQ ID NO: | Description | Sequence |
|---|---|---|
| | | CAGTAGTAATACAAGATAATAGTGACATAAAAGTA<br>GTGCCAAGAAGAAAAGCAAAGATCATCAGGGATTA<br>TGGAAAACAGATGGCAGGTGATGATTGTGTGGCAA<br>GTAGACAGGATGAGGATTAA |
| 23 | Helper/Rev; HIV RRE; Binds Rev element | AGGAGCTTTGTTCCTTGGGTTCTTGGGAGCAGCAGG<br>AAGCACTATGGGCGCAGCGTCAATGACGCTGACGG<br>TACAGGCCAGACAATTATTGTCTGGTATAGTGCAGC<br>AGCAGAACAATTTGCTGAGGGCTATTGAGGCGCAA<br>CAGCATCTGTTGCAACTCACAGTCTGGGGCATCAAG<br>CAGCTCCAGGCAAGAATCCTGGCTGTGGAAAGATA<br>CCTAAAGGATCAACAGCTCCT |
| 24 | Helper/Rev; HIV Rev; Nuclear export and stabilize viral mRNA | ATGGCAGGAAGAAGCGGAGACAGCGACGAAGAAC<br>TCCTCAAGGCAGTCAGACTCATCAAGTTTCTCTATC<br>AAAGCAACCCACCTCCCAATCCCGAGGGGACCCGA<br>CAGGCCCGAAGGAATAGAAGAAGAAGGTGGAGAG<br>AGAGACAGAGACAGATCCATTCGATTAGTGAACGG<br>ATCCTTAGCACTTATCTGGGACGATCTGCGGAGCCT<br>GTGCCTCTTCAGCTACCACCGCTTGAGAGACTTACT<br>CTTGATTGTAACGAGGATTGTGGAACTTCTGGGACG<br>CAGGGGGTGGGAAGCCCTCAAATATTGGTGGAATC<br>TCCTACAATATTGGAGTCAGGAGCTAAAGAATAG |
| 25 | Envelope; CMV promoter; Transcription | ACATTGATTATTGACTAGTTATTAATAGTAATCAAT<br>TACGGGGTCATTAGTTCATAGCCCATATATGGAGTT<br>CCGCGTTACATAACTTACGGTAAATGGCCCGCCTGG<br>CTGACCGCCCAACGACCCCCGCCCATTGACGTCAAT<br>AATGACGTATGTTCCCATAGTAACGCCAATAGGGAC<br>TTTCCATTGACGTCAATGGGTGGAGTATTTACGGTA<br>AACTGCCCACTTGGCAGTACATCAAGTGTATCATAT<br>GCCAAGTACGCCCCCTATTGACGTCAATGACGGTAA<br>ATGGCCCGCCTGGCATTATGCCCAGTACATGACCTT<br>ATGGGACTTTCCTACTTGGCAGTACATCTACGTATT<br>AGTCATCGCTATTACCATGGTGATGCGGTTTTGGCA<br>GTACATCAATGGGCGTGGATAGCGGTTTGACTCACG<br>GGGATTTCCAAGTCTCCACCCCATTGACGTCAATGG<br>GAGTTTGTTTTGGCACCAAAATCAACGGGACTTTCC<br>AAAATGTCGTAACAACTCCGCCCCATTGACGCAAAT<br>GGGCGGTAGGCGTGTACGGTGGGAGGTCTATATAA<br>GC |
| 26 | Envelope; VSV-G; Glycoprotein envelope-cell entry | ATGAAGTGCCTTTTGTACTTAGCCTTTTTATTCATTG<br>GGGTGAATTGCAAGTTCACCATAGTTTTTCCACACA<br>ACCAAAAAGGAAACTGGAAAAATGTTCCTTCTAATT<br>ACCATTATTGCCCGTCAAGCTCAGATTTAAATTGGC<br>ATAATGACTTAATAGGCACAGCCTTACAAGTCAAA<br>ATGCCCAAGAGTCACAAGGCTATTCAAGCAGACGG<br>TTGGATGTGTCATGCTTCCAAATGGGTCACTACTTG<br>TGATTTCCGCTGGTATGGACCGAAGTATATAACACA<br>TTCCATCCGATCCTTCACTCCATCTGTAGAACAATG<br>CAAGGAAAGCATTGAACAAACGAAACAAGGAACTT<br>GGCTGAATCCAGGCTTCCCTCCTCAAAGTTGTGGAT<br>ATGCAACTGTGACGGATGCCGAAGCAGTGATTGTCC<br>AGGTGACTCCTCACCATGTGCTGGTTGATGAATACA<br>CAGGAGAATGGGTTGATTCACAGTTCATCAACGGA<br>AAATGCAGCAATTACATATGCCCCACTGTCCATAAC<br>TCTACAACCTGGCATTCTGACTATAAGGTCAAAGGG<br>CTATGTGATTCTAACCTCATTTCCATGGACATCACCT<br>TCTTCTCAGAGGACGGAGAGCTATCATCCCTGGGAA<br>AGGAGGGCACAGGGTTCAGAAGTAACTACTTTGCTT<br>ATGAAACTGGAGGCAAGGCCTGCAAAATGCAATAC<br>TGCAAGCATTGGGGAGTCAGACTCCCATCAGGTGTC<br>TGGTTCGAGATGGCTGATAAGGATCTCTTTGCTGCA<br>GCCAGATTCCCTGAATGCCCAGAAGGGTCAAGTATC<br>TCTGCTCCATCTCAGACCTCAGTGGATGTAAGTCTA<br>ATTCAGGACGTTGAGAGGATCTTGGATTATTCCCTC<br>TGCCAAGAAACCTGGAGCAAAATCAGAGCGGGTCT<br>TCCAATCTCTCCAGTGGATCTCAGCTATCTTGCTCCT<br>AAAAACCCAGGAACCGGTCCTGCTTTCACCATAATC<br>AATGGTACCCTAAAATACTTTGAGACCAGATACATC<br>AGAGTCGATATTGCTGCTCCAATCCTCTCAAGAATG<br>GTCGGAATGATCAGTGGAACTACCACAGAAAGGGA<br>ACTGTGGGATGACTGGGCACCATATGAAGACGTGG<br>AAATTGGACCCAATGGAGTTCGTGAGGACCAGTTCA<br>GGATATAAGTTTCCTTTATACATGATTGGACATGGT |

| SEQ ID NO: | Description | Sequence |
|---|---|---|
| | | ATGTTGGACTCCGATCTTCATCTTAGCTCAAAGGCT<br>CAGGTGTTCGAACATCCTCACATTCAAGACGCTGCT<br>TCGCAACTTCCTGATGATGAGAGTTTATTTTTTGGTG<br>ATACTGGGCTATCCAAAAATCCAATCGAGCTTGTAG<br>AAGGTTGGTTCAGTAGTTGGAAAAGCTCTATTGCCT<br>CTTTTTTCTTTATCATAGGGTTAATCATTGGACTATT<br>CTTGGTTCTCCGAGTTGGTATCCATCTTTGCATTAAA<br>TTAAAGCACACCAAGAAAAGACAGATTTATACAGA<br>CATAGAGATGA |
| 27 | Helper/Rev;<br>CMV early<br>(CAG) enhancer;<br>Enhance<br>Transcription | TAGTTATTAATAGTAATCAATTACGGGGTCATTAGT<br>TCATAGCCCATATATGGAGTTCCGCGTTACATAACT<br>TACGGTAAATGGCCCGCCTGGCTGACCGCCCAACG<br>ACCCCCGCCCATTGACGTCAATAATGACGTATGTTC<br>CCATAGTAACGCCAATAGGGACTTTCCATTGACGTC<br>AATGGGTGGACTATTTACGGTAAACTGCCCACTTGG<br>CAGTACATCAAGTGTATCATATGCCAAGTACGCCCC<br>CTATTGACGTCAATGACGGTAAATGGCCCGCCTGGC<br>ATTATGCCCAGTACATGACCTTATGGGACTTTCCTA<br>CTTGGCAGTACATCTACGTATTAGTCATC |
| 28 | Helper/Rev;<br>Chicken beta<br>actin intron;<br>Enhance gene<br>expression | GGAGTCGCTGCGTTGCCTTCGCCCCGTGCCCCGCTC<br>CGCGCCGCCTCGCGCCGCCCGCCCCGGCTCTGACTG<br>ACCGCGTTACTCCCACAGGTGAGCGGGCGGGACGG<br>CCCTTCTCCTCCGGGCTGTAATTAGCGCTTGGTTTAA<br>TGACGGCTCGTTTCTTTTCTGTGGCTGCGTGAAAGC<br>CTTAAAGGGCTCCGGGAGGGCCCTTTGTGCGGGGG<br>GGAGCGGCTCGGGGGGTGCGTGCGTGTGTGTGTGC<br>GTGGGGAGCGCCGCGTGCGGCCCGCGCTGCCCGGC<br>GGCTGTGAGCGCTGCGGGCGCGGCGCGGGGCTTTG<br>TGCGCTCCGCGTGTGCGCGAGGGGAGCGCGGCCGG<br>GGGCGGTGCCCCGCGGTGCGGGGGGGCTGCGAGGG<br>GAACAAAGGCTGCGTGCGGGGTGTGTGCGTGGGGG<br>GGTGAGCAGGGGGTGTGGGCGCGGCGGTCGGGCTG<br>TAACCCCCCCTGCACCCCCCTCCCCGAGTTGCTGA<br>GCACGGCCCGGCTTCGGGTGCGGGGCTCCGTGCGG<br>GGCGTGGCGCGGGGCTCGCCGTGCCGGGCGGGGGG<br>TGGCGGCAGGTGGGGGTGCCGGGCGGGGCGGGGCC<br>GCCTCGGGCCGGGGAGGGCTCGGGGGAGGGGCGCG<br>GCGGCCCCGGAGCGCCGGCGGCTGTCGAGGCGCGG<br>CGAGCCGCAGCCATTGCCTTTTATGGTAATCGTGCG<br>AGAGGGCGCAGGGACTTCCTTTGTCCCAAATCTGGC<br>GGAGCCGAAATCTGGGAGGCGCCGCCGCACCCCCT<br>CTAGCGGGCGCGGGCGAAGCGGTGCGGCGCCGGCA<br>GGAAGGAAATGGGCGGGGAGGGCCTTCGTGCGTCG<br>CCGCGCCGCCGTCCCCTTCTCCATCTCCAGCCTCGG<br>GGCTGCCGCAGGGGGACGGCTGCCTTCGGGGGGGA<br>CGGGGCAGGGCGGGGTTCGGCTTCTGGCGTGTGAC<br>CGGCGG |
| 29 | Helper/Rev;<br>Rabbit beta<br>globin poly A;<br>RNA stability | AGATCTTTTTCCCTCTGCCAAAAATTATGGGGACAT<br>CATGAAGCCCCTTGAGCATCTGACTTCTGGCTAATA<br>AAGGAAATTTATTTTCATTGCAATAGTGTGTTGGAA<br>TTTTTTGTGTCTCTCACTCGGAAGGACATATGGGAG<br>GGCAAATCATTTAAAACATCAGAATGAGTATTTGGT<br>TTAGAGTTTGGCAACATATGCCATATGCTGGCTGCC<br>ATGAACAAAGGTGGCTATAAAGAGGTCATCAGTAT<br>ATGAAACAGCCCCCTGCTGTCCATTCCTTATTCCAT<br>AGAAAAGCCTTGACTTGAGGTTAGATTTTTTTATA<br>TTTTGTTTTGTGTTATTTTTTTCTTTAACATCCCTAAA<br>ATTTTCCTTACATGTTTTACTAGCCAGATTTTTCCTC<br>CTCTCCTGACTACTCCCAGTCATAGCTGTCCCTCTTC<br>TCTTATGAAGATC |
| 30 | Envelope; Beta<br>globin intron;<br>Enhance gene<br>expression | GTGAGTTTGGGGACCCTTGATTGTTCTTTCTTTTTCG<br>CTATTGTAAAATTCATGTTATATGGAGGGGGCAAAG<br>TTTTCAGGGTGTTGTTTAGAATGGGAAGATGTCCCT<br>TGTATCACCATGGACCCTCATGATAATTTTGTTTCTT<br>TCACTTTCTACTCTGTTGACAACCATTGTCTCCTCTT<br>ATTTTCTTTTCATTTTCTGTAACTTTTTCGTTAAACTT<br>TAGCTTGCATTTGTAACGAATTTTTAAATTCACTTTT<br>GTTTATTTGTCAGATTGTAAGTACTTTCTCTAATCAC<br>TTTTTTTTCAAGGCAATCAGGGTATATTATATTGTAC<br>TTCAGCACAGTTTTAGAGAACAATTGTTATAATTAA<br>ATGATAAGGTAGAATATTTCTGCATATAAATTCTGG<br>CTGGCGTGGAAATATTCTTATTGGTAGAAACAACTA |

| SEQ ID NO: | Description | Sequence |
|---|---|---|
| | | CACCCTGGTCATCATCCTGCCTTTCTCTTTATGGTTA<br>CAATGATATACACTGTTTGAGATGAGGATAAAATAC<br>TCTGAGTCCAAACCGGGCCCCTCTGCTAACCATGTT<br>CATGCCTTCTTCTCTTTCCTACAG |
| 31 | Envelope; Rabbit beta globin poly A; RNA stability | AGATCTTTTTCCCTCTGCCAAAAATTATGGGGACAT<br>CATGAAGCCCCTTGAGCATCTGACTTCTGGCTAATA<br>AAGGAAATTTATTTTCATTGCAATAGTGTGTTGGAA<br>TTTTTTGTGTCTCTCACTCGGAAGGACATATGGGAG<br>GGCAAATCATTTAAAACATCAGAATGAGTATTTGGT<br>TTAGAGTTTGGCAACATATGCCCATATGCTGGCTGC<br>CATGAACAAAGGTTGGCTATAAAGAGGTCATCAGT<br>ATATGAAACAGCCCCCTGCTGTCCATTCCTTATTCC<br>ATAGAAAAGCCTTGACTTGAGGTTAGATTTTTTTTA<br>TATTTTGTTTTGTGTTATTTTTTTCTTTAACATCCCTA<br>AAATTTTCCTTACATGTTTTACTAGCCAGATTTTTCC<br>TCCTCTCCTGACTACTCCCAGTCATAGCTGTCCCTCT<br>TCTCTTATGGAGATC |
| 32 | Primer | TAAGCAGAATTCATGAATTTGCCAGGAAGAT |
| 33 | Primer | CCATACAATGAATGGACACTAGGCGGCCGCACGAAT |
| 34 | Gag, Pol, Integrase fragment | GAATTCATGAATTTGCCAGGAAGATGGAAACCAAA<br>AATGATAGGGGGAATTGGAGGTTTTATCAAAGTAA<br>GACAGTATGATCAGATACTCATAGAAATCTGCGGA<br>CATAAAGCTATAGGTACAGTATTAGTAGGACCTACA<br>CCTGTCAACATAATTGGAAGAAATCTGTTGACTCAG<br>ATTGGCTGCACTTTAAATTTTCCCATTAGTCCTATTG<br>AGACTGTACCAGTAAAATTAAAGCCAGGAATGGAT<br>GGCCCAAAAGTTAAACAATGGCCATTGACAGAAGA<br>AAAAATAAAAGCATTAGTAGAAATTTGTACAGAAA<br>TGGAAAAGGAAGGAAAAATTTCAAAAATTGGGCCT<br>GAAAATCCATACAATACTCCAGTATTTGCCATAAAG<br>AAAAAAGACAGTACTAAATGGAGAAAATTAGTAGA<br>TTTCAGAGAACTTAATAAGAGAACTCAAGATTTCTG<br>GGAAGTTCAATTAGGAATACCACATCCTGCAGGGTT<br>AAAACAGAAAAAATCAGTAACAGTACTGGATGTGG<br>GCGATGCATATTTTTCAGTTCCCTTAGATAAAGACT<br>TCAGGAAGTATACTGCATTTACCATACCTAGTATAA<br>ACAATGAGACACCAGGGATTAGATATCAGTACAAT<br>GTGCTTCCACAGGGATGGAAAGGATCACCAGCAAT<br>ATTCCAGTGTAGCATGACAAAAATCTTAGAGCCTTT<br>TAGAAAACAAAATCCAGACATAGTCATCTATCAAT<br>ACATGGATGATTTGTATGTAGGATCTGACTTAGAAA<br>TAGGGCAGCATAGAACAAAAATAGAGGAACTGAGA<br>CAACATCTGTTGAGGTGGGGATTTACCACACCAGAC<br>AAAAAACATCAGAAAGAACCTCCATTCCTTTGGATG<br>GGTTATGAACTCCATCCTGATAAATGGACAGTACAG<br>CCTATAGTGCTGCCAGAAAAGGACAGCTGGACTGT<br>CAATGACATACAGAAATTAGTGGGAAAATTGAATT<br>GGGCAAGTCAGATTTATGCAGGGATTAAAGTAAGG<br>CAATTATGTAAACTTCTTAGGGGAACCAAAGCACTA<br>ACAGAAGTAGTACCACTAACAGAAGAAGCAGAGCT<br>AGAACTGGCAGAAAACAGGGAGATTCTAAAAGAAC<br>CGGTACATGGAGTGTATTATGACCCATCAAAAGACT<br>TAATAGCAGAAATACAGAAGCAGGGGCAAGGCCAA<br>TGGACATATCAAATTTATCAAGAGCCATTTAAAAAT<br>CTGAAAACAGGAAAGTATGCAAGAATGAAGGGTGC<br>CCACACTAATGATGTGAAACAATTAACAGAGGCAG<br>TACAAAAAATAGCCACAGAAAGCATAGTAATATGG<br>GGAAAGACTCCTAAATTTAAATTACCCATACAAAA<br>GGAAACATGGGAAGCATGGTGGACAGAGTATTGGC<br>AAGCCACCTGGATTCCTGAGTGGGAGTTTGTCAATA<br>CCCCTCCCTTAGTGAAGTTATGGTACCAGTTAGAGA<br>AAGAACCCATAATAGGAGCAGAAACTTTCTATGTA<br>GATGGGGCAGCCAATAGGGAAACTAAATTAGGAAA<br>AGCAGGATATGTAACTGACAGAGGAAGACAAAAAG<br>TTGTCCCCCTAACGGACACAACAAATCAGAAGACT<br>GAGTTACAAGCAATTCATCTAGCTTTGCAGGATTCG<br>GGATTAGAAGTAAACATAGTGACAGACTCACAATA<br>TGCATTGGGAATCATTCAAGCACAACCAGATAAGA<br>GTGAATCAGAGTTAGTCAGTCAAATAATAGAGCAG<br>TTAATAAAAAAGGAAAAGGTCTACCTGGCATGGGT<br>ACCAGCACACAAAGGAATTGGAGGAAATGAACAAG |

| SEQ ID NO: | Description | Sequence |
|---|---|---|
| | | TAGATAAATTGGTCAGTGCTGGAATCAGGAAAGTA<br>CTATTTTTAGATGGAATAGATAAGGCCCAAGAAGA<br>ACATGAGAAATATCACAGTAATTGGAGAGCAATGG<br>CTAGTGATTTTAACCTACCACCTGTAGTAGCAAAAG<br>AAATAGTAGCCAGCTGTGATAAATGTCAGCTAAAA<br>GGGGAAGCCATGCATGGACAAGTAGACTGTAGCCC<br>AGGAATATGGCAGCTAGATTGTACACATTTAGAAG<br>GAAAAGTTATCTTGGTAGCAGTTCATGTAGCCAGTG<br>GATATATAGAAGCAGAAGTAATTCCAGCAGAGACA<br>GGGCAAGAAACAGCATACTTCCTCTTAAAATTAGCA<br>GGAAGATGGCCAGTAAAAACAGTACATACAGACAA<br>TGGCAGCAATTTCACCAGTACTACAGTTAAGGCCGC<br>CTGTTGGTGGGCGGGGATCAAGCAGGAATTTGGCA<br>TTCCCTACAATCCCCAAAGTCAAGGAGTAATAGAAT<br>CTATGAATAAAGAATTAAAGAAAATTATAGGACAG<br>GTAAGAGATCAGGCTGAACATCTTAAGACAGCAGT<br>ACAAATGGCAGTATTCATCCACAATTTTAAAAGAAA<br>AGGGGGGATTGGGGGGTACAGTGCAGGGGAAAGA<br>ATAGTAGACATAATAGCAACAGACATACAAACTAA<br>AGAATTACAAAAACAAATTACAAAAATTCAAAATT<br>TTCGGGTTTATTACAGGGACAGCAGAGATCCAGTTT<br>GGAAAGGACCAGCAAAGCTCCTCTGGAAAGGTGAA<br>GGGGCAGTAGTAATACAAGATAATAGTGACATAAA<br>AGTAGTGCCAAGAAGAAAAGCAAAGATCATCAGGG<br>ATTATGGAAAACAGATGGCAGGTGATGATTGTGTG<br>GCAAGTAGACAGGATGAGGATTAA |
| 35 | DNA Fragment containing Rev, RRE and rabbit beta globin poly A | TCTAGAATGGCAGGAAGAAGCGGAGACAGCGACGA<br>AGAGCTCATCAGAACAGTCAGACTCATCAAGCTTCT<br>CTATCAAAGCAACCCACCTCCCAATCCCGAGGGGA<br>CCCGACAGGCCCGAAGGAATAGAAGAAGAAGGTGG<br>AGAGAGAGACAGAGACAGATCCATTCGATTAGTGA<br>ACGGATCCTTGGCACTTATCTGGGACGATCTGCGGA<br>GCCTGTGCCTCTTCAGCTACCACCGCTTGAGAGACT<br>TACTCTTGATTGTAACGAGGATTGTGGAACTTCTGG<br>GACGCAGGGGGTGGGAAGCCCTCAAATATTGGTGG<br>AATCTCCTACAATATTGGAGTCAGGAGCTAAAGAAT<br>AGAGGAGCTTTGTTCCTTGGGTTCTTGGGAGCAGCA<br>GGAAGCACTATGGGCGCAGCGTCAATGACGCTGAC<br>GGTACAGGCCAGACAATTATTGTCTGGTATAGTGCA<br>GCAGCAGAACAATTTGCTGAGGGCTATTGAGGCGC<br>AACAGCATCTGTTGCAACTCACAGTCTGGGGCATCA<br>AGCAGCTCCAGGCAAGAATCCTGGCTGTGGAAAGA<br>TACCTAAAGGATCAACAGCTCCTAGATCTTTTTCCC<br>TCTGCCAAAAATTATGGGGACATCATGAAGCCCCTT<br>GAGCATCTGACTTCTGGCTAATAAAGGAAATTTATT<br>TTCATTGCAATAGTGTGTTGGAATTTTTTGTGTCTCT<br>CACTCGGAAGGACATATGGGAGGGCAAATCATTTA<br>AAACATCAGAATGAGTATTTGGTTTAGAGTTTGGCA<br>ACATATGCCATATGCTGGCTGCCATGAACAAAGGTG<br>GCTATAAAGAGGTCATCAGTATATGAAACAGCCCC<br>CTGCTGTCCATTCCTTATTCCATAGAAAAGCCTTGA<br>CTTGAGGTTAGATTTTTTTTATATTTTGTTTTGTGTT<br>ATTTTTTTCTTTAACATCCCTAAAATTTTCCTTACAT<br>GTTTTACTAGCCAGATTTTTCCTCCTCTCCTGACTAC<br>TCCCAGTCATAGCTGTCCCTCTTCTCTTATGAAGATC<br>CCTCGACCTGCAGCCCAAGCTTGGCGTAATCATGGT<br>CATAGCTGTTTCCTGTGTGAAATTGTTATCCGCTCAC<br>AATTCCACACAACATACGAGCCGGAAGCATAAAGT<br>GTAAAGCCTGGGGTGCCTAATGAGTGAGCTAACTC<br>ACATTAATTGCGTTGCGCTCACTGCCCGCTTTCCAG<br>TCGGGAAACCTGTCGTGCCAGCGGATCCGCATCTCA<br>ATTAGTCAGCAACCATAGTCCCGCCCCTAACTCCGC<br>CCATCCCGCCCCTAACTCCGCCCAGTTCCGCCCATT<br>CTCCGCCCCATGGCTGACTAATTTTTTTTATTTATGC<br>AGAGGCCGAGGCCGCCTCGGCCTCTGAGCTATTCCA<br>GAAGTAGTGAGGAGGCTTTTTTGGAGGCCTAGGCTT<br>TTGCAAAAAGCTAACTTGTTTATTGCAGCTTATAAT<br>GGTTACAAATAAAGCAATAGCATCACAAATTTCAC<br>AAATAAAGCATTTTTTCACTGCATTCTAGTTGTGGT<br>TTGTCCAAACTCATCAATGTATCTTATCAGCGGCCG<br>CCCCGGG |
| 36 | DNA fragment containing the CAG | ACGCGTTAGTTATTAATAGTAATCAATTACGGGGTC<br>ATTAGTTCATAGCCCATATATGGAGTTCCGCGTTAC<br>ATAACTTACGGTAAATGGCCCGCCTGGCTGACCGCC |

| SEQ ID NO: | Description | Sequence |
|---|---|---|
|  | enhancer/promoter/intron sequence | CAACGACCCCCGCCCATTGACGTCAATAATGACGTA<br>TGTTCCCATAGTAACGCCAATAGGGACTTTCCATTG<br>ACGTCAATGGGTGGACTATTTACGGTAAACTGCCCA<br>CTTGGCAGTACATCAAGTGTATCATATGCCAAGTAC<br>GCCCCCTATTGACGTCAATGACGGTAAATGGCCCGC<br>CTGGCATTATGCCCAGTACATGACCTTATGGGACTT<br>TCCTACTTGGCAGTACATCTACGTATTAGTCATCGC<br>TATTACCATGGGTCGAGGTGAGCCCCACGTTCTGCT<br>TCACTCTCCCCATCTCCCCCCCCTCCCCACCCCCAAT<br>TTTGTATTTATTTATTTTTTAATTATTTTGTGCAGCG<br>ATGGGGGCGGGGGGGGGGGGGCGCGCGCCAGGC<br>GGGGCGGGGCGGGGCGAGGGGCGGGGCGGGGCGA<br>GGCGGAGAGGTGCGGCGGCAGCCAATCAGAGCGGC<br>GCGCTCCGAAAGTTTCCTTTTATGGCGAGGCGGCGG<br>CGGCGGCGGCCCTATAAAAAGCGAAGCGCGCGGCG<br>GCGGGAGTCGCTGCGTTGCCTTCGCCCCGTGCCCC<br>GCTCCGCGCCGCCTCGCGCCGCCCGCCCCGGCTCTG<br>ACTGACCGCGTTACTCCCACAGGTGAGCGGGCGGG<br>ACGGCCCTTCTCCTCCGGGCTGTAATTAGCGCTTGG<br>TTTAATGACGGCTCGTTTCTTTTCTGTGGCTGCGTGA<br>AAGCCTTAAAGGGCTCCGGGAGGGCCCTTTGTGCG<br>GGGGGGAGCGGCTCGGGGGTGCGTGCGTGTGTGT<br>GTGCGTGGGGAGCGCCGCGTGCGCCCGCGCGCTGCC<br>CGGCGGCTGTGAGCGCTGCGGGCGCGGCGCGGGC<br>TTTGTGCGCTCCGCGTGTGCGCGAGGGGAGCGCGGC<br>CGGGGGCGGTGCCCCGCGGTGCGGGGGGGCTGCGA<br>GGGGAACAAAGGCTGCGTGCGGGGTGTGTGCGTGG<br>GGGGGTGAGCAGGGGGTGTGGGCGCGGCGGTCGGG<br>CTGTAACCCCCCCCTGCACCCCCCTCCCCGAGTTGC<br>TGAGCACGGCCCGGCTTCGGGTGCGGGGCTCCGTGC<br>GGGGCGTGGCGCGGGGCTCGCCGTGCCGGGCGGGG<br>GGTGGCGGCAGGTGGGGGTGCCGGGCGGGGCGGGG<br>CCGCCTCGGGCCGGGGAGGGCTCGGGGAGGGGCG<br>CGGCGGCCCCGGAGCGCCGGCGGCTGTCGAGGCGC<br>GGCGAGCCGCAGCCATTGCCTTTTATGGTAATCGTG<br>CGAGAGGGCGCAGGGACTTCCTTTGTCCCAAATCTG<br>GCGGAGCCGAAATCTGGGAGGCGCCGCCGCACCCC<br>CTCTAGCGGGCGCGGGCGAAGCGGTGCGGCGCCGG<br>CAGGAAGGAAATGGGCGGGAGGGCCTTCGTGCGT<br>CGCCGCGCCGCCGTCCCCTTCTCCATCTCCAGCCTC<br>GGGGCTGCCGCAGGGGGACGGCTGCCTTCGGGGGG<br>GACGGGGCAGGGCGGGGTTCGGCTTCTGGCGTGTG<br>ACCGGCGGGAATTC |
| 37 | DNA fragment containing V SV-G | GAATTCATGAAGTGCCTTTTGTACTTAGCCTTTTTAT<br>TCATTGGGGTGAATTGCAAGTTCACCATAGTTTTTC<br>CACACAACCAAAAAGGAAACTGGAAAAATGTTCCT<br>TCTAATTACCATTATTGCCCGTCAAGCTCAGATTTA<br>AATTGGCATAATGACTTAATAGGCACAGCCTTACAA<br>GTCAAAATGCCCAAGAGTCACAAGGCTATTCAAGC<br>AGACGGTTGGATGTGTCATGCTTCCAAATGGGTCAC<br>TACTTGTGATTTCCGCTGGTATGGACCGAAGTATAT<br>AACACATTCCATCCGATCCTTCACTCCATCTGTAGA<br>ACAATGCAAGGAAAGCATTGAACAAACGAAACAAG<br>GAACTTGGCTGAATCCAGGCTTCCCTCCTCAAAGTT<br>GTGGATATGCAACTGTGACGGATGCCGAAGCAGTG<br>ATTGTCCAGGTGACTCCTCACCATGTGCTGGTTGAT<br>GAATACACAGGAGAATGGGTTGATTCACAGTTCATC<br>AACGGAAAATGCAGCAATTACATATGCCCCACTGTC<br>CATAACTCTACAACCTGGCATTCTGACTATAAGGTC<br>AAAGGGCTATGTGATTCTAACCTCATTTCCATGGAC<br>ATCACCTTCTTCTCAGAGGACGGAGAGCTATCATCC<br>CTGGGAAGGAGGGCACAGGGTTCAGAAGTAACTA<br>CTTTGCTTATGAAACTGGAGGCAAGGCCTGCAAAAT<br>GCAATACTGCAAGCATTGGGGAGTCAGACTCCCATC<br>AGGTGTCTGGTTCGAGATGGCTGATAAGGATCTCTT<br>TGCTGCAGCCAGATTCCCTGAATGCCAGAAGGGTC<br>AAGTATCTCTGCTCCATCTCAGACCTCAGTGGATGT<br>AAGTCTAATTCAGGACGTTGAGAGGATCTTGGATTA<br>TTCCCTCTGCCAAGAAACCTGGAGCAAAATCAGAG<br>CGGGTCTTCCAATCTCTCCAGTGGATCTCAGCTATC<br>TTGCTCCTAAAAACCCAGGAACCGGTCCTGCTTTCA<br>CCATAATCAATGGTACCCTAAAATACTTTGAGACCA<br>GATACATCAGAGTCGATATTGCTGCTCCAATCCTCT<br>CAAGAATGGTCGGAATGATCAGTGGAACTACCACA<br>GAAAGGGAACTGTGGGATGACTGGGCACCATATGA |

| SEQ ID NO: | Description | Sequence |
|---|---|---|
| | | AGACGTGGAAATTGGACCCAATGGAGTTCTGAGGA CCAGTTCAGGATATAAGTTTCCTTTATACATGATTG GACATGGTATGTTGGACTCCGATCTTCATCTTAGCT CAAAGGCTCAGGTGTTCGAACATCCTCACATTCAAG ACGCTGCTTCGCAACTTCCTGATGATGAGAGTTTAT TTTTTGGTGATACTGGGCTATCCAAAAATCCAATCG AGCTTGTAGAAGGTTGGTTCAGTAGTTGGAAAAGCT CTATTGCCTCTTTTTTCTTTATCATAGGGTTAATCAT TGGACTATTCTTGGTTCTCCGAGTTGGTATCCATCTT TGCATTAAATTAAAGCACACCAAGAAAAGACAGAT TTATACAGACATAGAGATGAGAATTC |
| 38 | Rev; RSV promoter; Transcription | ATGGCAGGAAGAAGCGGAGACAGCGACGAAGAAC TCCTCAAGGCAGTCAGACTCATCAAGTTTCTCTATC AAAGCAACCCACCTCCCAATCCCGAGGGGACCCGA CAGGCCCGAAGGAATAGAAGAAGAAGGTGGAGAG AGAGACAGAGACAGATCCATTCGATTAGTGAACGG ATCCTTAGCACTTATCTGGGACGATCTGCGGAGCCT GTGCCTCTTCAGCTACCACCGCTTGAGAGACTTACT CTTGATTGTAACGAGGATTGTGGAACTTCTGGGACG CAGGGGGTGGGAAGCCCTCAAATATTGGTGGAATC TCCTACAATATTGGAGTCAGGAGCTAAAGAATAG |
| 39 | Rev; HIV Rev; Nuclear export and stabilize viral mRNA | ATGGCAGGAAGAAGCGGAGACAGCGACGAAGAAC TCCTCAAGGCAGTCAGACTCATCAAGTTTCTCTATC AAAGCAACCCACCTCCCAATCCCGAGGGGACCCGA CAGGCCCGAAGGAATAGAAGAAGAAGGTGGAGAG AGAGACAGAGACAGATCCATTCGATTAGTGAACGG ATCCTTAGCACTTATCTGGGACGATCTGCGGAGCCT GTGCCTCTTCAGCTACCACCGCTTGAGAGACTTACT CTTGATTGTAACGAGGATTGTGGAACTTCTGGGACG CAGGGGGTGGGAAGCCCTCAAATATTGGTGGAATC TCCTACAATATTGGAGTCAGGAGCTAAAGAATAG |
| 40 | RSV promoter and HIV Rev | CAATTGCGATGTACGGGCCAGATATACGCGTATCTG AGGGGACTAGGGTGTGTTTAGGCGAAAAGCGGGGC TTCGGTTGTACGCGGTTAGGAGTCCCCTCAGGATAT AGTAGTTTCGCTTTTGCATAGGGAGGGGGAAATGTA GTCTTATGCAATACACTTGTAGTCTTGCAACATGGT AACGATGAGTTAGCAACATGCCTTACAAGGAGAGA AAAAGCACCGTGCATGCCGATTGGTGGAAGTAAGG TGGTACGATCGTGCCTTATTAGGAAGGCAACAGAC AGGTCTGACATGGATTGGACGAACCACTGAATTCCG CATTGCAGAGATAATTGTATTTAAGTGCCTAGCTCG ATACAATAAACGCCATTTGACCATTCACCACATTGG TGTGCACCTCCAAGCTCGAGCTCGTTTAGTGAACCG TCAGATCGCCTGGAGACGCCATCCACGCTGTTTTGA CCTCCATAGAAGACACCGGGACCGATCCAGCCTCCC CTCGAAGCTAGCGATTAGGCATCTCCTATGGCAGGA AGAAGCGGAGACAGCGACGAAGAACTCCTCAAGGC AGTCAGACTCATCAAGTTTCTCTATCAAAGCAACCC ACCTCCCAATCCCGAGGGGACCCGACAGGCCCGAA GGAATAGAAGAAGAAGGTGGAGAGAGAGACAGAG ACAGATCCATTCGATTAGTGAACGGATCCTTAGCAC TTATCTGGGACGATCTGCGGAGCCTGTGCCTCTTCA GCTACCACCGCTTGAGAGACTTACTCTTGATTGTAA CGAGGATTGTGGAACTTCTGGGACGCAGGGGGTGG GAAGCCCTCAAATATTGGTGGAATCTCCTACAATAT TGGAGTCAGGAGCTAAAGAATAGTCTAGA |
| 41 | Elongation Factor-1 alpha (EF1-alpha) promoter | CCGGTGCCTAGAGAAGGTGGCGCGGGGTAAACTGG GAAAGTGATGTCGTGTACTGGCTCCGCCTTTTTCCC GAGGGTGGGGGAGAACCGTATATAAGTGCAGTAGT CGCCGTGAACGTTCTTTTTCGCAACGGGTTTGCCGC CAGAACACAGGTAAGTGCCGTGTGTGGTTCCCGCG GGCCTGGCCTCTTTACGGGTTATGGCCCTTGCGTGC CTTGAATTACTTCCACGCCCCTGGCTGCAGTACGTG ATTCTTGATCCCGAGCTTCGGGTTGGAAGTGGGTGG GAGAGTTCGAGGCCTTGCGCTTAAGGAGCCCCTTCG CCTCGTGCTTGAGTTGAGGCCTGGCCTGGGCGCTGG GGCCGCCGCGTGCGAATCTGGTGGCACCTTCGCGCC TGTCTCGCTGCTTTCGATAAGTCTCTAGCCATTTAAA ATTTTTGATGACCTGCTGCGACGCTTTTTTTCTGGCA AGATAGTCTTGTAAATGCGGGCCAAGATCTGCACAC TGGTATTTCGGTTTTTGGGGCCGCGGGCGGCGACGG GGCCCGTGCGTCCCAGCGCACATGTTCGGCGAGGC |

-continued

| SEQ ID NO: | Description | Sequence |
|---|---|---|
| | | GGGGCCTGCGAGCGCGGCCACCGAGAATCGGACGG<br>GGGTAGTCTCAAGCTGGCCGGCCTGCTCTGGTGCCT<br>GGCCTCGCGCCGCCGTGTATCGCCCCGCCCTGGGCG<br>GCAAGGCTGGCCCGGTCGGCACCAGTTGCGTGAGC<br>GGAAAGATGGCCGCTTCCCGGCCCTGCTGCAGGGA<br>GCTCAAAATGGAGGACGCGGCGCTCGGGAGAGCGG<br>GCGGGTGAGTCACCCACACAAAGGAAAAGGGCCTT<br>TCCGTCCTCAGCCGTCGCTTCATGTGACTCCACGGA<br>GTACCGGGCGCCGTCCAGGCACCTCGATTAGTTCTC<br>GAGCTTTTGGAGTACGTCGTCTTTAGGTTGGGGGGA<br>GGGGTTTTATGCGATGGAGTTTCCCCACACTGAGTG<br>GGTGGAGACTGAAGTTAGGCCAGCTTGGCACTTGAT<br>GTAATTCTCCTTGGAATTTGCCCTTTTTGAGTTTGGA<br>TCTTGGTTCATTCTCAAGCCTCAGACAGTGGTTCAA<br>AGTTTTTTTCTTCCATTTCAGGTGTCGTGA |
| 42 | Promoter; PGK | GGGGTTGGGGTTGCGCCTTTTCCAAGGCAGCCCTGG<br>GTTTGCGCAGGGACGCGGCTGCTCTGGGCGTGGTTC<br>CGGGAAACGCAGCGGCGCCGACCCTGGGTCTCGCA<br>CATTCTTCACGTCCGTTCGCAGCGTCACCCGGATCT<br>TCGCCGCTACCCTTGTGGGCCCCCCGGCGACGCTTC<br>CTGCTCCGCCCCTAAGTCGGGAAGGTTCCTTGCGGT<br>TCGCGGCGTGCCGGACGTGACAAACGGAAGCCGCA<br>CGTCTCACTAGTACCCTCGCAGACGGACAGCGCCAG<br>GGAGCAATGGCAGCGCGCCGACCGCGATGGGCTGT<br>GGCCAATAGCGGCTGCTCAGCAGGGCGCGCCGAGA<br>GCAGCGGCCGGGAAGGGGCGGTGCGGGAGGCGGG<br>GTGTGGGGCGGTAGTGTGGGCCCTGTTCCTGCCCGC<br>GCGGTGTTCCGCATTCTGCAAGCCTCCGGAGCGCAC<br>GTCGGCAGTCGGCTCCCTCGTTGACCGAATCACCGA<br>CCTCTCTCCCCAG |
| 43 | Promoter; UbC | GCGCCGGGTTTTGGCGCCTCCCGCGGGCGCCCCCCT<br>CCTCACGGCGAGCGCTGCCACGTCAGACGAAGGGC<br>GCAGGAGCGTTCCTGATCCTTCCGCCCGGACGCTCA<br>GGACAGCGGCCCGCTGCTCATAAGACTCGGCCTTAG<br>AACCCCAGTATCAGCAGAAGGACATTTTAGGACGG<br>GACTTGGGTGACTCTAGGGCACTGGTTTTCTTTCCA<br>GAGAGCGGAACAGGCGAGGAAAAGTAGTCCCTTCT<br>CGGCGATTCTGCGGAGGGATCTCCGTGGGGCGGTG<br>AACGCCGATGATTATATAAGGACGCGCCGGGTGTG<br>GCACAGCTAGTTCCGTCGCAGCCGGGATTTGGGTCG<br>CGGTTCTTGTTTGTGGATCGCTGTGATCGTCACTTGG<br>TGAGTTGCGGGCTGCTGGGCTGGCCGGGGCTTTCGT<br>GGCCGCCGGGCCGCTCGGTGGGACGGAAGCGTGTG<br>GAGAGACCGCCAAGGGCTGTAGTCTGGGTCCGCGA<br>GCAAGGTTGCCCTGAACTGGGGGTTGGGGGGAGCG<br>CACAAAATGGCGGCTGTTCCCGAGTCTTGAATGGAA<br>GACGCTTGTAAGGCGGGCTGTGAGGTCGTTGAAAC<br>AAGGTGGGGGGCATGGTGGGCGGCAAGAACCCAAG<br>GTCTTGAGGCCTTCGCTAATGCGGGAAAGCTCTTAT<br>TCGGGTGAGATGGGCTGGGGCACCATCTGGGGACC<br>CTGACGTGAAGTTTGTCACTGACTGGAGAACTCGGG<br>TTTGTCGTCTGGTTGCGGGGGCGGCAGTTATGCGGT<br>GCCGTTGGGCAGTGCACCCGTACCTTTGGGAGCGCG<br>CGCCTCGTCGTGTCGTGACGTCACCCGTTCTGTTGG<br>CTTATAATGCAGGGTGGGGCCACCTGCCGGTAGGTG<br>TGCGGTAGGCTTTTCTCCGTCGCAGGACGCAGGGTT<br>CGGGCCTAGGGTAGGCTCTCCTGAATCGACAGGCG<br>CCGGACCTCTGGTGAGGGGAGGGATAAGTGAGGCG<br>TCAGTTTCTTTGGTCGGTTTTATGTACCTATCTTCTT<br>AAGTAGCTGAAGCTCCGGTTTTGAACTATGCGCTCG<br>GGGTTGGCGAGTGTGTTTTGTGAAGTTTTTTAGGCA<br>CCTTTTGAAATGTAATCATTTGGGTCAATATGTAAT<br>TTTCAGTGTTAGACTAGTAAA |
| 44 | Poly A; SV40 | GTTTATTGCAGCTTATAATGGTTACAAATAAAGCAA<br>TAGCATCACAAATTTCACAAATAAAGCATTTTTTTC<br>ACTGCATTCTAGTTGTGGTTTGTCCAAACTCATCAA<br>TGTATCTTATCA |
| 45 | Poly A; bGH | GACTGTGCCTTCTAGTTGCCAGCCATCTGTTGTTTGC<br>CCTCCCCCGTGCCTTCCTTGACCCTGGAAGGTGCC<br>ACTCCCACTGTCCTTTCCTAATAAAATGAGGAAATT<br>GCATCGCATTGTCTGAGTAGGTGTCATTCTATTCTG<br>GGGGGTGGGTGGGGCAGGACAGCAAGGGGGAGG |

| SEQ ID NO: | Description | Sequence |
|---|---|---|
| | | ATTGGGAAGACAATAGCAGGCATGCTGGGGATGCG<br>GTGGGCTCTATGG |
| 46 | Envelope;<br>RD114 | ATGAAACTCCCAACAGGAATGGTCATTTTATGTAGC<br>CTAATAATAGTTCGGGCAGGGTTTGACGACCCCCGC<br>AAGGCTATCGCATTAGTACAAAAACAACATGGTAA<br>ACCATGCGAATGCAGCGGAGGGCAGGTATCCGAGG<br>CCCCACCGAACTCCATCCAACAGGTAACTTGCCCAG<br>GCAAGACGGCCTACTTAATGACCAACCAAAAATGG<br>AAATGCAGAGTCACTCCAAAAAATCTCACCCCTAGC<br>GGGGGAGAACTCCAGAACTGCCCCTGTAACACTTTC<br>CAGGACTCGATGCACAGTTCTTGTTATACTGAATAC<br>CGGCAATGCAGGGCGAATAATAAGACATACTACAC<br>GGCCACCTTGCTTAAAATACGGTCTGGGAGCCTCAA<br>CGAGGTACAGATATTACAAAACCCCAATCAGCTCCT<br>ACAGTCCCTTGTAGGGGCTCTATAAATCAGCCCGT<br>TTGCTGGAGTGCCACAGCCCCCATCCATATCTCCGA<br>TGGTGGAGGACCCCTCGATACTAAGAGAGTGTGGA<br>CAGTCCAAAAAGGCTAGAACAAATTCATAAGGCT<br>ATGCATCCTGAACTTCAATACCACCCCTTAGCCCTG<br>CCCAAAGTCAGAGATGACCTTAGCCTTGATGCACGG<br>ACTTTTGATATCCTGAATACCACTTTTAGGTTACTCC<br>AGATGTCCAATTTTAGCCTTGCCCAAGATTGTTGGC<br>TCTGTTTAAAACTAGGTACCCCTACCCCTCTTGCGA<br>TACCCACTCCCTCTTTAACCTACTCCCTAGCAGACTC<br>CCTAGCGAATGCCTCCTGTCAGATTATACCTCCCCT<br>CTTGGTTCAACCGATGCAGTTCTCCAACTCGTCCTG<br>TTTATCTTCCCCTTTCATTAACGATACGGAACAAAT<br>AGACTTAGGTGCAGTCACCTTTACTAACTGCACCTC<br>TGTAGCCAATGTCAGTAGTCCTTTATGTGCCCTAAA<br>CGGGTCAGTCTTCCTCTGTGGAAATAACATGGCATA<br>CACCTATTTACCCCAAAACTGGACAGGACTTTGCGT<br>CCAAGCCTCCCTCCTCCCCGACATTGACATCATCCC<br>GGGGGATGAGCCAGTCCCCATTCCTGCCATTGATCA<br>TTATATACATAGACCTAAACGAGCTGTACAGTTCAT<br>CCCTTTACTAGCTGGACTGGGAATCACCGCAGCATT<br>CACCACCGGAGCTACAGGCCTAGGTGTCTCCGTCAC<br>CCAGTATACAAAATTATCCCATCAGTTAATATCTGA<br>TGTCCAAGTCTTATCCGGTACCATACAAGATTTACA<br>AGACCAGGTAGACTCGTTAGCTGAAGTAGTTCTCCA<br>AAATAGGAGGGGACTGGACCTACTAACGGCAGAAC<br>AAGGAGGAATTTGTTTAGCCTTACAAGAAAAATGCT<br>GTTTTTATGCTAACAAGTCAGGAATTGTGAGAAACA<br>AAATAAGAACCCTACAAGAAGAATTACAAAAACGC<br>AGGGAAAGCCTGGCATCCAACCCTCTCTGGACCGG<br>GCTGCAGGGCTTTCTTCCGTACCTCCTACCTCTCCTG<br>GGACCCCTACTCACCCTCCTACTCATACTAACCATT<br>GGGCCATGCGTTTTCAATCGATTGGTCCAATTTGTT<br>AAAGACAGGATCTCAGTGGTCCAGGCTCTGGTTTTG<br>ACTCAGCAATATCACCAGCTAAAACCCATAGAGTA<br>CGAGCCATGA |
| 47 | Envelope;<br>GALV | ATGCTTCTCACCTCAAGCCCGCACCACCTTCGGCAC<br>CAGATGAGTCCTGGGAGCTGGAAAAGACTGATCAT<br>CCTCTTAAGCTGCGTATTCGGAGACGGCAAAACGA<br>GTCTGCAGAATAAGAACCCCCACCAGCCTGTGACCC<br>TCACCTGGCAGGTACTGTCCCAAACTGGGGACGTTG<br>TCTGGGACAAAAAGGCAGTCCAGCCCCTTTGGACTT<br>GGTGGCCCTCTCTTACACCTGATGTATGTGCCCTGG<br>CGGCCGGTCTTGAGTCCTGGGATATCCCGGGATCCG<br>ATGTATCGTCCTCTAAAAGAGTTAGACCTCCTGATT<br>CAGACTATACTGCCGCTTATAAGCAAATCACCTGGG<br>GAGCCATAGGGTGCAGCTACCCTCGGGCTAGGACC<br>AGGATGGCAAATTCCCCCTTCTACGTGTGTCCCCGA<br>GCTGGCCGAACCCATTCAGAAGCTAGGAGGTGTGG<br>GGGGCTAGAATCCCTATACTGTAAAGAATGGAGTT<br>GTGAGACCACGGGTACCGTTTATTGGCAACCCAAGT<br>CCTCATGGGACCTCATAACTGTAAAATGGGACCAA<br>AATGTGAAATGGGAGCAAAAATTTCAAAAGTGTGA<br>ACAAACCGGCTGGTGTAACCCCCTCAAGATAGACTT<br>CACAGAAAAGGAAAACTCTCCAGAGATTGGATAA<br>CGGAAAAAACCTGGGAATTAAGGTTCTATGTATATG<br>GACACCCAGGCATACAGTTGACTATCCGCTTAGAGG<br>TCACTAACATGCCGGTTGTGGCAGTGGGCCCAGACC<br>CTGTCCTTGCGGAACAGGGACCTCCTAGCAAGCCCC<br>TCACTCTCCCTCTCTCCCCACGGAAAGCGCCGCCCA |

| SEQ ID NO: | Description | Sequence |
|---|---|---|
| | | CCCCTCTACCCCCGGCGGCTAGTGAGCAAACCCCTG<br>CGGTGCATGGAGAAACTGTTACCCTAAACTCTCCGC<br>CTCCCACCAGTGGCGACCGACTCTTTGGCCTTGTGC<br>AGGGGGCCTTCCTAACCTTGAATGCTACCAACCCAG<br>GGGCCACTAAGTCTTGCTGGCTCTGTTTGGGCATGA<br>GCCCCCCTTATTATGAAGGGATAGCCTCTTCAGGAG<br>AGGTCGCTTATACCTCCAACCATACCCGATGCCACT<br>GGGGGGCCCAAGGAAAGCTTACCCTCACTGAGGTC<br>TCCGGACTCGGGTCATGCATAGGGAAGGTGCCTCTT<br>ACCCATCAACATCTTTGCAACCAGACCTTACCCATC<br>AATTCCTCTAAAAACCATCAGTATCTGCTCCCCTCA<br>AACCATAGCTGGTGGGCCTGCAGCACTGGCCTCACC<br>CCCTGCCTCTCCACCTCAGTTTTTAATCAGTCTAAAG<br>ACTTCTGTGTCCAGGTCCAGCTGATCCCCCGCATCT<br>ATTACCATTCTGAAGAAACCTTGTTACAAGCCTATG<br>ACAAATCACCCCCCAGGTTTAAAAGAGAGCCTGCCT<br>CACTTACCCTAGCTGTCTTCCTGGGGTTAGGGATTG<br>CGGCAGGTATAGGTACTGGCTCAACCGCCCTAATTA<br>AAGGGCCCATAGACCTCCAGCAAGGCCTAACCAGC<br>CTCCAAATCGCCATTGACGCTGACCTCCGGGCCCTT<br>CAGGACTCAATCAGCAAGCTAGAGGACTCACTGAC<br>TTCCCTATCTGAGGTAGTACTCCAAAATAGGAGAGG<br>CCTTGACTTACTATTCCTTAAAGAAGGAGGCCTCTG<br>CGCGGCCCTAAAAGAAGAGTGCTGTTTTTATGTAGA<br>CCACTCAGGTGCAGTACGAGACTCCATGAAAAAAC<br>TTAAAGAAAGACTAGATAAAAGACAGTTAGAGCGC<br>CAGAAAAACCAAAACTGGTATGAAGGGTGGTTCAA<br>TAACTCCCCTTGGTTTACTACCCTACTATCAACCATC<br>GCTGGGCCCTATTGCTCCTCCTTTTGTTACTCACTC<br>TTGGGCCCTGCATCATCAATAAATTAATCCAATTCA<br>TCAATGATAGGATAAGTGCAGTCAAAATTTTAGTCC<br>TTAGACAGAAATATCAGACCCTAGATAACGAGGAA<br>AACCTTTAA |
| 48 | Envelope; FUG | ATGGTTCCGCAGGTTCTTTTGTTTGTACTCCTTCTGG<br>GTTTTTCGTTGTGTTTCGGGAAGTTCCCCATTTACAC<br>GATACCAGACGAACTTGGTCCCTGGAGCCCTATTGA<br>CATACACCATCTCAGCTGTCCAAATAACCTGGTTGT<br>GGAGGATGAAGGATGTACCAACCTGTCCGAGTTCTC<br>CTACATGGAACTCAAAGTGGGATACATCTCAGCCAT<br>CAAAGTGAACGGGTTCACTTGCACAGGTGTTGTGAC<br>AGAGGCAGAGACCTACACCAACTTTGTTGGTTATGT<br>CACAACCACATTCAAGAGAAAGCATTTCCGCCCCAC<br>CCCAGACGCATGTAGAGCCGCGTATAACTGGAAGA<br>TGGCCGGTGACCCCAGATATGAAGAGTCCCTACAC<br>AATCCATACCCCGACTACCACTGGCTTCGAACTGTA<br>AGAACCACCAAAGAGTCCCTCATTATCATATCCCCA<br>AGTGTGACAGATTTGGACCCATATGACAAATCCCTT<br>CACTCAAGGGTCTTCCCTGGCGGAAAGTGCTCAGGA<br>ATAACGGTGTCCTCTACCTACTGCTCAACTAACCAT<br>GATTACACCATTTGGATGCCCGAGAATCCGAGACCA<br>AGGACACCTTGTGACATTTTTACCAATAGCAGAGGG<br>AAGAGAGCATCCAACGGGAACAAGACTTGCGGCTT<br>TGTGGATGAAAGAGGCCTGTATAAGTCTCTAAAAG<br>GAGCATGCAGGCTCAAGTTATGTGGAGTTCTTGGAC<br>TTAGACTTATGGATGGAACATGGGTCGCGATGCAA<br>ACATCAGATGAGACCAAATGGTGCCCTCCAGATCA<br>GTTGGTGAATTTGCACGACTTTCGCTCAGACGAGAT<br>CGAGCATCTCGTTGTGGAGGAGTTAGTTAAGAAAA<br>GAGAGGAATGTCTGGATGCATTAGAGTCCATCATG<br>ACCACCAAGTCAGTAAGTTTCAGACGTCTCAGTCAC<br>CTGAGAAAACTTGTCCCAGGGTTTGGAAAAGCATAT<br>ACCATATTCAACAAAACCTTGATGGAGGCTGATGCT<br>CACTACAAGTCAGTCCGGACCTGGAATGAGATCATC<br>CCCTCAAAAGGGTGTTTGAAAGTTGGAGGAAGGTG<br>CCATCCTCATGTGAACGGGGTGTTTTTCAATGGTAT<br>AATATTAGGGCCTGACGACCATGTCCTAATCCCAGA<br>GATGCAATCATCCCTCCTCCAGCAACATATGGAGTT<br>GTTGGAATCTTCAGTTATCCCCCTGATGCACCCCCT<br>GGCAGACCCTTCTACAGTTTTCAAAGAAGGTGATGA<br>GGCTGAGGATTTTGTTGAAGTTCACCTCCCCGATGT<br>GTACAAACAGATCTCAGGGGTTGACCTGGGTCTCCC<br>GAACTGGGGAAAGTATGTATTGATGACTGCAGGGG<br>CCATGATTGGCCTGGTGTTGATATTTTCCCTAATGA<br>CATGGTGCAGAGTTGGTATCCATCTTTGCATTAAAT |

-continued

| SEQ ID NO: | Description | Sequence |
|---|---|---|
| | | TAAAGCACACCAAGAAAAGACAGATTTATACAGAC ATAGAGATGAACCGACTTGGAAAGTAA |
| 49 | Envelope; LCMV | ATGGGTCAGATTGTGACAATGTTTGAGGCTCTGCCT CACATCATCGATGAGGTGATCAACATTGTCATTATT GTGCTTATCGTGATCACGGGTATCAAGGCTGTCTAC AATTTTGCCACCTGTGGGATATTCGCATTGATCAGT TTCCTACTTCTGGCTGGCAGGTCCTGTGGCATGTAC GGTCTTAAGGGACCCGACATTTACAAAGGAGTTTAC CAATTTAAGTCAGTGGAGTTTGATATGTCACATCTG AACCTGACCATGCCCAACGCATGTTCAGCCAACAAC TCCCACCATTACATCAGTATGGGGACTTCTGGACTA GAATTGACCTTCACCAATGATTCCATCATCAGTCAC AACTTTTGCAATCTGACCTCTGCCTTCAACAAAAAG ACCTTTGACCACACACTCATGAGTATAGTTTCGAGC CTACACCTCAGTATCAGAGGGAACTCCAACTATAAG GCAGTATCCTGCGACTTCAACAATGGCATAACCATC CAATACAACTTGACATTCTCAGATCGACAAAGTGCT CAGAGCCAGTGTAGAACCTTCAGAGGTAGAGTCCT AGATATGTTTAGAACTGCCTTCGGGGGGAAATACAT GAGGAGTGGCTGGGGCTGGACAGGCTCAGATGGCA AGACCACCTGGTGTAGCCAGACGAGTTACCAATAC CTGATTATACAAAATAGAACCTGGGAAAACCACTG CACATATGCAGGTCCTTTTGGGATGTCCAGGATTCT CCTTTCCCAAGAGAAGACTAAGTTCTTCACTAGGAG ACTAGCGGGCACATTCACCTGGACTTTGTCAGACTC TTCAGGGGTGGAGAATCCAGGTGGTTATTGCCTGAC CAAATGGATGATTCTTGCTGCAGAGCTTAAGTGTTT CGGGAACACAGCAGTTGCGAAATGCAATGTAAATC ATGATGCCGAATTCTGTGACATGCTGCGACTAATTG ACTACAACAAGGCTGCTTTGAGTAAGTTCAAAGAG GACGTAGAATCTGCCTTGCACTTATTCAAAACAACA GTGAATTCTTTGATTTCAGATCAACTACTGATGAGG AACCACTTGAGAGATCTGATGGGGGTGCCATATTGC AATTACTCAAAGTTTTGGTACCTAGAACATGCAAAG ACCGGCGAAACTAGTGTCCCCAAGTGCTGGCTTGTC ACCAATGGTTCTTACTTAAATGAGACCCACTTCAGT GATCAAATCGAACAGGAAGCCGATAACATGATTAC AGAGATGTTGAGGAAGGATTACATAAAGAGGCAGG GGAGTACCCCCCTAGCATTGATGGACCTTCTGATGT TTTCCACATCTGCATATCTAGTCAGCATCTTCCTGCA CCTTGTCAAAATACCAACACACAGGCACATAAAAG GTGGCTCATGTCCAAAGCCACACCGATTAACCAACA AAGGAATTTGTAGTTGTGGTGCATTTAAGGTGCCTG GTGTAAAAACCGTCTGGAAAAGACGCTGA |
| 50 | Envelope; FPV | ATGAACACTCAAATCCTGGTTTTCGCCCTTGTGGCA GTCATCCCCACAAATGCAGACAAAATTTGTCTTGGA CATCATGCTGTATCAAATGGCACCAAAGTAAACAC ACTCACTGAGAGAGGAGTAGAAGTTGTCAATGCAA CGGAAACAGTGGAGCGGACAAACATCCCCAAATT TGCTCAAAAGGGAAAAGAACCACTGATCTTGGCCA ATGCGGACTGTTAGGGACCATTACCGGACCACCTCA ATGCGACCAATTTCTAGAATTTTCAGCTGATCTAAT AATCGAGAGACGAGAAGGAAATGATGTTTGTTACC CGGGGAAGTTTGTTAATGAAGAGGCATTGCGACAA ATCCTCAGAGGATCAGGTGGGATTGACAAAGAAAC AATGGGATTCACATATAGTGGAATAAGGACCAACG GAACAACTAGTGCATGTAGAAGATCAGGGTCTTCAT TCTATGCAGAAATGGAGTGGCTCCTGTCAAATACAG ACAATGCTGCTTTCCCACAAATGACAAAATCATACA AAAACACAAGGAGAGAATCAGCTCTGATAGTCTGG GGAATCCACCATTCAGGATCAACCACCGAACAGAC CAAACTATATGGGAGTGGAAATAAACTGATAACAG TCGGGAGTTCCAAATATCATCAATCTTTTGTGCCGA GTCCAGGAACACGACCGCAGATAAATGGCCAGTCC GGACGGATTGATTTTCATTGGTTGATCTTGGATCCC AATGATACAGTTACTTTTAGTTTCAATGGGGCTTTC ATAGCTCCAAATCGTGCCAGCTTCTTGAGGGGAAAG TCCATGGGGATCCAGAGCGATGTGCAGGTTGATGCC AATTGCGAAGGGAATGCTACCACAGTGGAGGGAC TATAACAAGCAGATTGCCTTTTCAAAACATCAATAG CAGAGCAGTTGGCAAATGCCCAAGATATGTAAAAC AGGAAAGTTTATTATTGGCAACTGGGATGAAGAAC GTTCCCGAACCTTCCAAAAAAGGAAAAAAGAGG CCTGTTTGGCGCTATAGCAGGGTTTATTGAAAATGG |

| SEQ ID NO: | Description | Sequence |
|---|---|---|
| | | TTGGGAAGGTCTGGTCGACGGGTGGTACGGTTTCAG<br>GCATCAGAATGCACAAGGAGAAGGAACTGCAGCAG<br>ACTACAAAAGCACCCAATCGGCAATTGATCAGATA<br>ACCGGAAAGTTAAATAGACTCATTGAGAAAACCAA<br>CCAGCAATTTGAGCTAATAGATAATGAATTCACTGA<br>GGTGGAAAAGCAGATTGGCAATTTAATTAACTGGA<br>CCAAAGACTCCATCACAGAAGTATGGTCTTACAATG<br>CTGAACTTCTTGTGGCAATGGAAAACCAGCACACTA<br>TTGATTTGGCTGATTCAGAGATGAACAAGCTGTATG<br>AGCGAGTGAGGAAACAATTAAGGGAAAATGCTGAA<br>GAGGATGGCACTGGTTGCTTTGAAATTTTTCATAAA<br>TGTGACGATGATTGTATGGCTAGTATAAGGAACAAT<br>ACTTATGATCACAGCAAATACAGAGAAGAAGCGAT<br>GCAAAATAGAATACAAATTGACCCAGTCAAATTGA<br>GTAGTGGCTACAAAGATGTGATACTTTGGTTTAGCT<br>TCGGGGCATCATGCTTTTTGCTTCTTGCCATTGCAAT<br>GGGCCTTGTTTTCATATGTGTGAAGAACGGAAACAT<br>GCGGTGCACTATTTGTATATAA |
| 51 | Envelope; RRV | AGTGTAACAGAGCACTTTAATGTGTATAAGGCTACT<br>AGACCATACCTAGCACATTGCGCCGATTGCGGGGA<br>CGGGTACTTCTGCTATAGCCCAGTTGCTATCGAGGA<br>GATCCGAGATGAGGCGTCTGATGGCATGCTTAAGAT<br>CCAAGTCTCCGCCCAAATAGGTCTGGACAAGGCAG<br>GCACCCACGCCCACACGAAGCTCCGATATATGGCTG<br>GTCATGATGTTCAGGAATCTAAGAGAGATTCCTTGA<br>GGGTGTACACGTCCGCAGCGTGCTCCATACATGGGA<br>CGATGGGACACTTCATCGTCGCACACTGTCCACCAG<br>GCGACTACCTCAAGGTTTCGTTCGAGGACGCAGATT<br>CGCACGTGAAGGCATGTAAGGTCCAATACAAGCAC<br>AATCCATTGCCGGTGGGTAGAGAAGTTCGTGGTT<br>AGACCACACTTTGGCGTAGAGCTGCCATGCACCTCA<br>TACCAGCTGACAACGGCTCCCACCGACGAGGAGAT<br>TGACATGCATACACCGCCAGATATACCGGATCGCAC<br>CCTGCTATCACAGACGGCGGGCAACGTCAAAATAA<br>CAGCAGGCGGCAGGACTATCAGGTACAACTGTACC<br>TGCGGCCGTGACAACGTAGGCACTACCAGTACTGA<br>CAAGACCATCAACACATGCAAGATTGACCAATGCC<br>ATGCTGCCGTCACCAGCCATGACAAATGGCAATTTA<br>CCTCTCCATTTGTTCCCAGGGCTGATCAGACAGCTA<br>GGAAAGGCAAGGTACACGTTCCGTTCCCTCTGACTA<br>ACGTCACCTGCCGAGTGCCGTTGGCTCGAGCGCCGG<br>ATGCCACCTATGGTAAGAAGGAGGTGACCCTGAGA<br>TTACACCCAGATCATCCGACGCTCTTCTCCTATAGG<br>AGTTTAGGAGCCGAACCGCACCCGTACGAGGAATG<br>GGTTGACAAGTTCTCTGAGCGCATCATCCCAGTGAC<br>GGAAGAAGGGATTGAGTACCAGTGGGGCAACAACC<br>CGCCGGTCTGCCTGTGGGCGCAACTGACGACCGAG<br>GGCAAACCCCATGGCTGGCCACATGAAATCATTCA<br>GTACTATTATGGACTATACCCCGCCGCCACTATTGC<br>CGCAGTATCCGGGGCGAGTCTGATGGCCCTCCTAAC<br>TCTGGCGGCCACATGCTGCATGCTGGCCACCGCGAG<br>GAGAAAGTGCCTAACACCGTACGCCCTGACGCCAG<br>GAGCGGTGGTACCGTTGACACTGGGGCTGCTTTGCT<br>GCGCACCGAGGGCGAATGCA |
| 52 | Envelope; MLV 10A1 | AGTGTAACAGAGCACTTTAATGTGTATAAGGCTACT<br>AGACCATACCTAGCACATTGCGCCGATTGCGGGGA<br>CGGGTACTTCTGCTATAGCCCAGTTGCTATCGAGGA<br>GATCCGAGATGAGGCGTCTGATGGCATGCTTAAGAT<br>CCAAGTCTCCGCCCAAATAGGTCTGGACAAGGCAG<br>GCACCCACGCCCACACGAAGCTCCGATATATGGCTG<br>GTCATGATGTTCAGGAATCTAAGAGAGATTCCTTGA<br>GGGTGTACACGTCCGCAGCGTGCTCCATACATGGGA<br>CGATGGGACACTTCATCGTCGCACACTGTCCACCAG<br>GCGACTACCTCAAGGTTTCGTTCGAGGACGCAGATT<br>CGCACGTGAAGGCATGTAAGGTCCAATACAAGCAC<br>AATCCATTGCCGGTGGGTAGAGAAGTTCGTGGTT<br>AGACCACACTTTGGCGTAGAGCTGCCATGCACCTCA<br>TACCAGCTGACAACGGCTCCCACCGACGAGGAGAT<br>TGACATGCATACACCGCCAGATATACCGGATCGCAC<br>CCTGCTATCACAGACGGCGGGCAACGTCAAAATAA<br>CAGCAGGCGGCAGGACTATCAGGTACAACTGTACC<br>TGCGGCCGTGACAACGTAGGCACTACCAGTACTGA<br>CAAGACCATCAACACATGCAAGATTGACCAATGCC<br>ATGCTGCCGTCACCAGCCATGACAAATGGCAATTTA |

| SEQ ID NO: | Description | Sequence |
|---|---|---|
|  |  | CCTCTCCATTTGTTCCCAGGGCTGATCAGACAGCTA GGAAAGGCAAGGTACACGTTCCGTTCCCTCTGACTA ACGTCACCTGCCGAGTGCCGTTGGCTCGAGCGCCGG ATGCCACCTATGGTAAGAAGGAGGTGACCCTGAGA TTACACCCAGATCATCCGACGCTCTTCTCCTATAGG AGTTTAGGAGCCGAACCGCACCCGTACGAGGAATG GGTTGACAAGTTCTCTGAGCGCATCATCCCAGTGAC GGAAGAAGGGATTGAGTACCAGTGGGGCAACAACC CGCCGGTCTGCCTGTGGGCGCAACTGACGACCGAG GGCAAACCCCATGGCTGGCCACATGAAATCATTCA GTACTATTATGGACTATACCCCGCCGCCACTATTGC CGCAGTATCCGGGGCGAGTCTGATGGCCCTCCTAAC TCTGGCGGCCACATGCTGCATGCTGGCCACCGCGAG GAGAAAGTGCCTAACACCGTACGCCCTGACGCCAG GAGCGGTGGTACCGTTGACACTGGGGCTGCTTTGCT GCGCACCGAGGGCGAATGCA |
| 53 | Envelope; Ebola | ATGGGTGTTACAGGAATATTGCAGTTACCTCGTGAT CGATTCAAGAGGACATCATTCTTTCTTTGGGTAATT ATCCTTTTCCAAAGAACATTTTCCATCCCACTTGGA GTCATCCACAATAGCACATTACAGGTTAGTGATGTC GACAAACTGGTTTGCCGTGACAAACTGTCATCCACA AATCAATTGAGATCAGTTGGACTGAATCTCGAAGG GAATGGAGTGGCAACTGACGTGCCATCTGCAACTA AAAGATGGGGCTTCAGGTCCGGTGTCCCACCAAAG GTGGTCAATTATGAAGCTGGTGAATGGGCTGAAAA CTGCTACAATCTTGAAATCAAAAAACCTGACGGGA GTGAGTGTCTACCAGCAGCGCCAGACGGGATTCGG GGCTTCCCCCGGTGCCGGTATGTGCACAAAGTATCA GGAACGGGACCGTGTGCCGGAGACTTTGCCTTCCAC AAAGAGGGTGCTTTCTTCCTGTATGACCGACTTGCT TCCACAGTTATCTACCGAGGAACGACTTTCGCTGAA GGTGTCGTTGCATTTCTGATACTGCCCCAAGCTAAG AAGGACTTCTTCAGCTCACACCCCTTGAGAGAGCCG GTCAATGCAACGGAGGACCCGTCTAGTGGCTACTAT TCTACCACAATTAGATATCAAGCTACCGGTTTTGGA ACCAATGAGACAGAGTATTTGTTCGAGGTTGACAAT TTGACCTACGTCCAACTTGAATCAAGATTCACACCA CAGTTTCTGCTCCAGCTGAATGAGACAATATATACA AGTGGGAAAAGGAGCAATACCACGGGAAAACTAAT TTGGAAGGTCAACCCCGAAATTGATACAACAATCG GGGAGTGGGCCTTCTGGGAAACTAAAAAAACCTCA CTAGAAAAATTCGCAGTGAAGAGTTGTCTTTCACAG CTGTATCAAACAGAGCCAAAAACATCAGTGGTCAG AGTCCGGCGCGAACTTCTTCCGACCCAGGGACCAAC ACAACAACTGAAGACCACAAAATCATGGCTTCAGA AAATTCCTCTGCAATGGTTCAAGTGCACAGTCAAGG AAGGGAAGCTGCAGTGTCGCATCTGACAACCCTTGC CACAATCTCCACGAGTCCTCAACCCCCCACAACCAA ACCAGGTCCGGACAACAGCACCCACAATACACCCG TGTATAAACTTGACATCTCTGAGGCAACTCAAGTTG AACAACATCACCGCAGAACAGACAACGACAGCACA GCCTCCGACACTCCCCCCGCCACGACCGCAGCCGGA CCCCTAAAAGCAGAGAACACCAACACGAGCAAGGG TACCGACCTCCTGGACCCCGCCACCACAACAAGTCC CCAAAACCACAGCGAGACCGCTGGCAACAACAACA CTCATCACCAAGATACCGGAGAAGAGAGTGCCAGC AGCGGGAAGCTAGGCTTAATTACCAATACTATTGCT GGAGTCGCAGGACTGATCACAGGCGGGAGGAGAGC TCGAAGAGAAGCAATTGTCAATGCTCAACCCAAAT GCAACCCTAATTTACATTACTGGACTACTCAGGATG AAGGTGCTGCAATCGGACTGGCCTGGATACCATATT TCGGGCCAGCAGCCGAGGGAATTTACATAGAGGGG CTGATGCACAATCAAGATGGTTTAATCTGTGGGTTG AGACAGCTGGCCAACGAGACGACTCAAGCTCTTCA ACTGTTCCTGAGAGCCACAACCGAGCTACGCACCTT TTCAATCCTCAACCGTAAGGCAATTGATTTCTTGCT GCAGCGATGGGGCGGCACATGCCACATTTTGGGAC CGGACTGCTGTATCGAACCACATGATTGGACCAAG AACATAACAGACAAAATTGATCAGATTATTCATGAT TTTGTTGATAAAACCCTTCCGGACCAGGGGGACAAT GACAATTGGTGGACAGGATGGAGACAATGGATACC GGCAGGTATTGGAGTTACAGGCGTTATAATTGCAGT TATCGCTTTATTCTGTATATGCAAATTTGTCTTTTAG |

| SEQ ID NO: | Description | Sequence |
|---|---|---|
| 54 | Polymerase III shRNA promoters; U6 promoter | TTTCCCATGATTCCTTCATATTTGCATATACGATACA AGGCTGTTAGAGAGATAATTGGAATTAATTTGACTG TAAACACAAAGATATTAGTACAAAATACGTGACGT AGAAAGTAATAATTTCTTGGGTAGTTTGCAGTTTTA AAATTATGTTTTAAAATGGACTATCATATGCTTACC GTAACTTGAAAGTATTTCGATTTCTTGGCTTTATATA TCTTGTGGAAAGGACGAAAC |
| 55 | Polymerase III shRNA promoters; 7SK promoter | CTGCAGTATTTAGCATGCCCCACCCATCTGCAAGGC ATTCTGGATAGTGTCAAAACAGCCGGAAATCAAGT CCGTTTATCTCAAACTTTAGCATTTTGGGAATAAAT GATATTTGCTATGCTGGTTAAATTAGATTTTAGTTA AATTTCCTGCTGAAGCTCTAGTACGATAAGCAACTT GACCTAAGTGTAAAGTTGAGATTTCCTTCAGGTTTA TATAGCTTGTGCGCCGCCTGGCTACCTC |
| 56 | FDPS target sequence #1 | GTCCTGGAGTACAATGCCATT |
| 57 | FDPS target sequence #2 | GCAGGATTTCGTTCAGCACTT |
| 58 | FDPS target sequence #3 | GCCATGTACATGGCAGGAATT |
| 59 | FDPS target sequence #4 | GCAGAAGGAGGCTGAGAAAGT |
| 60 | Non-targeting sequence | GCCGCTTTGTAGGATAGAGCTCGAGCTCTATCCTAC AAAGCGGCTTTTT |
| 61 | Forward primer | AGGAATTGATGGCGAGAAGG |
| 62 | Reverse primer | CCCAAAGAGGTCAAGGTAATCA |
| 63 | Forward primer | AGCGCGGCTACAGCTTCA |
| 64 | Reverse primer | GGCGACGTAGCACAGCTTCT |
| 65 | Left Inverted Terminal Repeat (Left ITR) | CCTGCAGGCAGCTGCGCGCTCGCTCGCTCACTGAGG CCGCCCGGGCGTCGGGCGACCTTTGGTCGCCCGGCC TCAGTGAGCGAGCGAGCGCGCAGAGAGGGAGTGGC CAACTCCATCACTAGGGGTTCCT |
| 66 | Right Inverted Terminal Repeat (Right ITR) | GAGCGGCCGCAGGAACCCCTAGTGATGGAGTTGGC CACTCCCTCTCTGCGCGCTCGCTCGCTCACTGAGGC CGGGCGACCAAAGGTCGCCCGACGCCCGGGCTTTG CCCGGGCGGCCTCAGTGAGCGAGCGAGCGCGCAGC TGCCTGCAGG |

While certain of the preferred embodiments of the present invention have been described and specifically exemplified above, it is not intended that the invention be limited to such embodiments. Various modifications may be made thereto without departing from the scope and spirit of the present invention.

What is claimed is:

1. A method of treating a cancer in a subject using an immunotherapy-based composition, the method comprising administering a therapeutically-effective amount of the immunotherapy-based composition to the subject, wherein the immunotherapy-based composition comprises a lentiviral particle, the lentiviral particle comprising:
   a. an envelope protein capable of infecting one or more cancer cells, and
   b. at least one encoded shRNA capable of inhibiting production of an enzyme of the mevalonate pathway, wherein the at least one encoded shRNA comprises a sequence having at least 80% percent identity with:
      i. GTCCTGGAGTACAATGCCATTCTCGAGAATGGCATTGTACTCCA GGACTTTTT (SEQ ID NO: 1);
      ii. GCAGGATTTCGTTCAGCACTTCTCGAGAAGTGCTGAACGAAATC CTGCTTTTT (SEQ ID NO: 2);
      iii. GCCATGTACATGGCAGGAATTCTCGAGAATTCCTGCCATGTACA TGGCTTTTT (SEQ ID NO: 3); or
      iv. GCAGAAGGAGGCTGAGAAAGTCTCGAGACTTTCTCAGCCTCCT TCTGCTTTTT (SEQ ID NO: 4);
   or
   c. at least one encoded microRNA capable of inhibiting production of an enzyme of the mevalonate pathway, wherein the at least one encoded microRNA comprises a sequence having at least 80% percent identity with:

```
                    (SEQ ID NO: 5)
i.    AAGGTATATTGCTGTTGACAGTGAGCGACACTTTCTCAGCCT

CCTTCTGCGTGAAGCCACAGATGGCAGAAGGAGGCTGAGAAA

GTGCTGCCTACTGCCTCGGACTTCAAGGGGCT;

(SEQ ID NO: 6)
ii.   AAGGTATATTGCTGTTGACAGTGAGCGACACTTTCTCAGCCT

CCTTCTGCGTGAAGCCACAGATGGCAGAAGGGCTGAGAAAGT

GCTGCCTACTGCCTCGGACTTCAAGGGGCT;

(SEQ ID NO: 7)
iii.  TGCTGTTGACAGTGAGCGACTTTCTCAGCCTCCTTCTGCGTG

AAGCCACAGATGGCAGAAGGAGGCTGAGAAAGTTGCCTACTG

CCTCGGA;
```

```
                    (SEQ ID NO: 8)
iv.   CCTGGAGGCTTGCTGAAGGCTGTATGCTGACTTTCTCAGCCT

CCTTCTGCTTTTGGCCACTGACTGAGCAGAAGGGCTGAGAAA

GTCAGGACACAAGGCCTGTTACTAGCACTCA;

(SEQ ID NO: 9)
v.    CATCTCCATGGCTGTACCACCTTGTCGGGACTTTCTCAGCCT

CCTTCTGCCTGTTGAATCTCATGGCAGAAGGAGGCGAGAAAG

TCTGACATTTTGGTATCTTTCATCTGACCA;
``` or

```
                    (SEQ ID NO: 10)
vi.   GGGCCTGGCTCGAGCAGGGGGCGAGGGATACTTTCTCAGCCT

CCTTCTGCTGGTCCCCTCCCCGCAGAAGGAGGCTGAGAAAGT

CCTTCCCTCCCAATGACCGCGTCTTCGTCG.
```

2. The method of claim 1, wherein the one or more cancer cells are present in a cancer selected from one or more of a carcinoma, a leukemia, a lymphoma, a sarcoma, a myeloma, a mesothelioma, a mixed type, or mixtures thereof.

3. The method of claim 1, wherein the one or more cancer cells are present in a hepatocellular carcinoma.

4. The method of claim 2, wherein the one or more cancer cells are present in a leukemia.

5. The method of claim 1, wherein the one or more cancer cells are capable of activating a gamma delta T cell resident in the subject following infection of the one or more cancer cells with the immunotherapy-based composition.

6. The method of claim 5, wherein activating the gamma delta T cell comprises increasing tumor necrosis factor (TNF)-α expression by the gamma delta T cell.

7. The method of claim 1, wherein the enzyme of the mevalonate pathway is farnesyl diphosphate synthase (FDPS).

8. The method of claim 1, further comprising administering an effective amount of an aminobisphosphonate drug to the subject.

9. The method of claim 8, wherein the aminobisphosphonate drug comprises zoledronic acid.

10. The method of claim 8, wherein the aminobisphosphonate drug is administered to the subject separately from the immunotherapy-based composition.

11. The method of claim 8, wherein the aminobisphosphonate drug is administered to the subject together with the immunotherapy-based composition.

* * * * *